US009567367B2

(12) United States Patent
Shirvan et al.

(10) Patent No.: US 9,567,367 B2
(45) Date of Patent: Feb. 14, 2017

(54) SYNTHETIC PEPTIDES FOR TREATMENT OF BACTERIAL INFECTIONS

(71) Applicant: ATOX BIO LTD., Ness Ziona (IL)

(72) Inventors: Anat Shirvan, Herzliya (IL); Dan Teleman, Ramat Efal (IL); Gila Arad, Jerusalem (IL); Raymond Kaempfer, Jerusalem (IL)

(73) Assignee: ATOX BIO LTD., Ness Ziona (IL)

( * ) Notice: Subject to any disclaimer, the term of this patent is extended or adjusted under 35 U.S.C. 154(b) by 0 days.

(21) Appl. No.: 14/372,629

(22) PCT Filed: Jan. 16, 2013

(86) PCT No.: PCT/IB2013/050401
§ 371 (c)(1),
(2) Date: Jul. 16, 2014

(87) PCT Pub. No.: WO2013/108193
PCT Pub. Date: Jul. 25, 2013

(65) Prior Publication Data
US 2014/0336359 A1 Nov. 13, 2014

Related U.S. Application Data

(60) Provisional application No. 61/586,971, filed on Jan. 16, 2012, provisional application No. 61/683,964, filed on Aug. 16, 2012.

(51) Int. Cl.
*C07K 7/06* (2006.01)
*A61K 38/08* (2006.01)
*A61K 45/06* (2006.01)
*A61K 38/17* (2006.01)

(52) U.S. Cl.
CPC ............... *C07K 7/06* (2013.01); *A61K 38/08* (2013.01); *A61K 38/1774* (2013.01); *A61K 45/06* (2013.01)

(58) Field of Classification Search
CPC .... A61K 38/08; A61K 38/1774; A61K 45/06; C07K 7/06
See application file for complete search history.

(56) References Cited

U.S. PATENT DOCUMENTS 7,060,277 B2   6/2006   Kaempfer
2005/0191296 A1* 9/2005 Kaempfer et al. ......... 424/144.1

FOREIGN PATENT DOCUMENTS

DE   102012008730 A1 * 6/2013 ........... A61K 31/201
WO   2004087196 A2   10/2004

OTHER PUBLICATIONS

Cawley MJ, Intravenous immunoglobulin as adjunctive treatment for streptococcal toxic shock syndrome associated with necrotizing fasciitis: case report and review, Pharmacotherapy. Sep. 1999;19(9):1094-8.*

Steven Opal, Clinical Gram-positive sepsis: Does it fundamentally differ from Gram-negative bacterial sepsis?, Critical Care Medicine Issue: vol. 27(8), Aug. 1999, pp. 1608-1616.*
DE102012008730A1, Google English Translation, Description and Claims, accessed Mar. 29, 2016.*
Human Body weight, Wikipedia, pp. 1-5, accessed on Mar. 29, 2016.*
R. Phillip Dellinger et al "Surviving Sepsis Campaign: International guidelines for management of severe sepsis and septic shock: 2008" Crit Care Med, 36:1:296-327 (2008).
Shiranee Sriskandan et al. "Streptococcal Pyrogenic Exotoxin A Release, Distribution, and Role in a Murine Model of Fasciitis and Multiorgan Failure Due to *Streptococcus pyogenes*" J Infect Dis, 173:1399-1407 (Jun. 1996).
Meera Unnikrishnan et al "The Bacterial Superantigen Streptococcal Mitogenic Exotoxin Z is the Major Immunoactibe Agent of *Streptococcus pyogenes*1" The Journal of Immunology, 169:2561-2569 (2002).
Meera Unnikrishnan et al. "Complementation of a speA negative *Streptococcus pyogenes* with speA: effects on virulence and production of streptococcal pyrogenic exotoxin A" Microbial Pathogenesis, 31:109-114 (Apr. 2001).
Gila Arad et al. "Superantigen antagonist protects against lethal shock and defines a new domain for T-cell activation" Nature Medicine, 6:4:414-421 (Apr. 2000).
Nicola N. Lynskey et al. "New understandings in *Streptococcus pyogenes*" Current Opinion in Infectious Diseases, 24: 196-202 (2011).
Martin Llewelyn et al. "Superantigens: microbial agents that corrupt immunity" The Lancet Infectious Diseases, 2: 156-162 (Mar. 2002).
Anna Nolan et al. "CD40 and CD80/86 Act Synergistically to Regulate Inflammation and Mortality in Polymicrobial Sepsis" American Journal Respiratory and Critical Care Medicine, 177:301-308 (2008).
Gila Arad et al. "Binding of Superantigen Toxins into the CD28 Homodimer Interface is Essential for Induction of Cytokine Genes That Mediate Lethal Shock" PLoS Biology, 9 : 9 : e1001149 : 1-14 (Sep. 2011).
Chun-Shiang Chung et al. "SOCS-1 is a central mediator of steroid-increased thymocyte apoptosis and decrease survival following sepsis" Apoptosis, 12:1143-1153 (Mar. 2007).
Chun-Shiang Chung et al."Deficiency of BID Protein Reduces Sepsis-Induced Apoptosis, Inflammation and Improves Septic Survival" Shock, 34 : 2 : 150-161 (Aug. 2010).
Prathiba Kurupati et al. "Chemokine-cleaving *Streptococcus pyogenes* protease SpyCEP is necessary and sufficient for bacterial dissemination within soft tissues and the respiratory tract" Molecular Microbiology, 76 : 6 :1387-1397 (Feb. 2010).
Madeleine W. Cunningham "Pathogenesis of Group A Streptococcal Infections" Clinical Microbiology Reviews, 13 : 2 : 470-511 (Jul. 2000).

(Continued)

*Primary Examiner* — James H Alstrum Acevedo
*Assistant Examiner* — Erinne Dabkowski
(74) *Attorney, Agent, or Firm* — Browdy and Neimark, PLLC

(57) ABSTRACT

Disclosed are peptides and methods for the treatment of bacterial infections and associated inflammation. Effective doses and treatment protocols are disclosed.

16 Claims, 34 Drawing Sheets

(56) References Cited

OTHER PUBLICATIONS

Tomas Bremell et al. "Experimental *Staphylococcus aureus* Arthritis in Mice" Infection and Immunity. 59 : 8 : 2615-2623 (Aug. 1991).
Zai-Qing Liu et al. "Staphylococcal peptidoglycans induce arthritis" Arthritis Research. 3:375-380 (2001).
International Search Report. Dated Jun. 6, 2013. Application No. PCT/IB2013/050401.
Arad et al. "Superantigen antagonist blocks Th1 cytokine gene induction and lethal shock" J. Leukoc. Biol. 69:921-927 (2001).

* cited by examiner

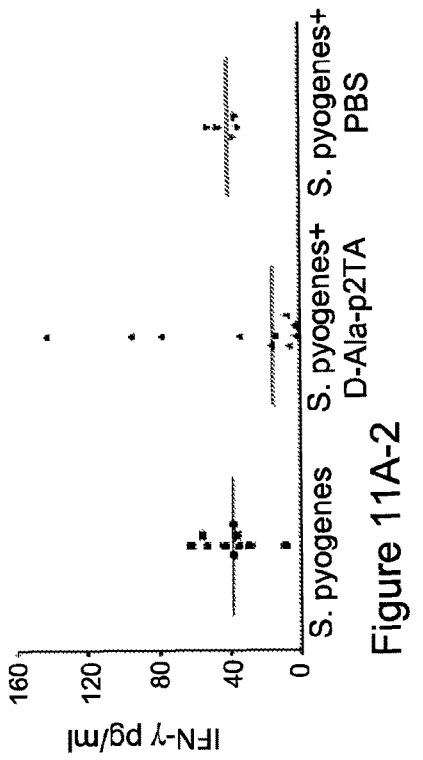
Figure 11A-1
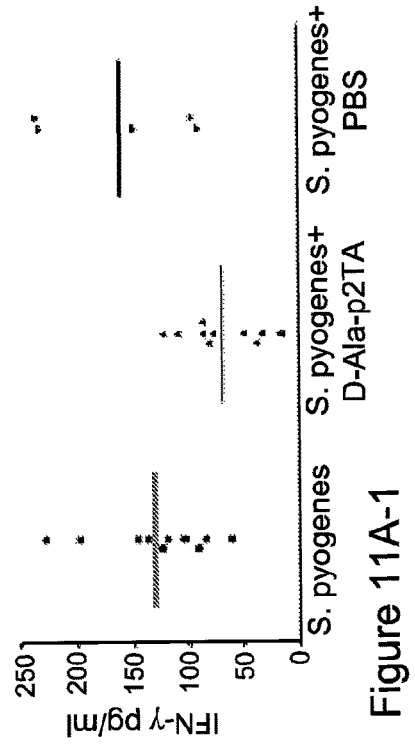
Figure 11A-3
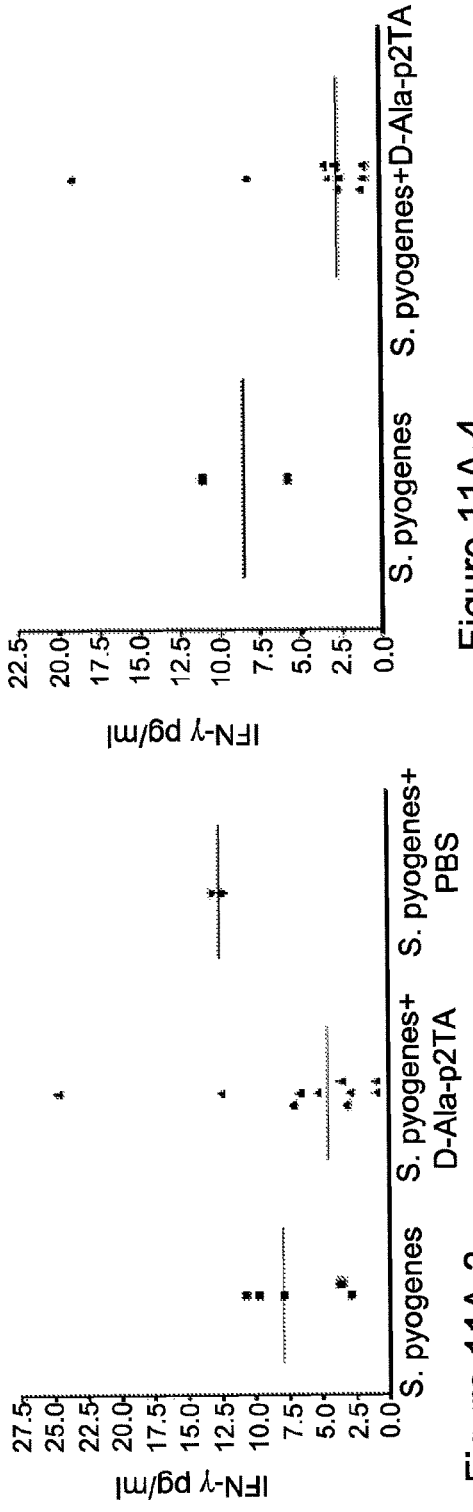
Figure 11A-2
Figure 11A-4

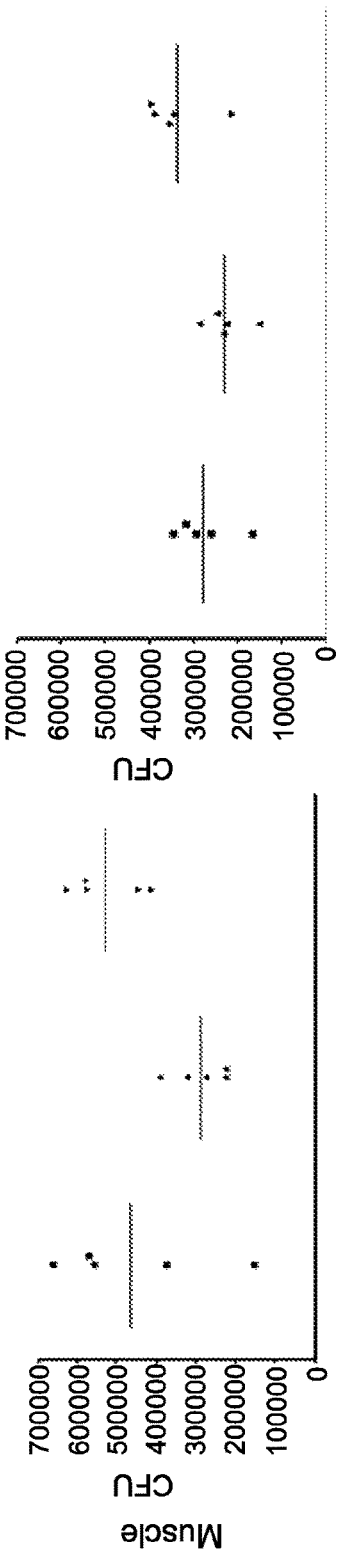
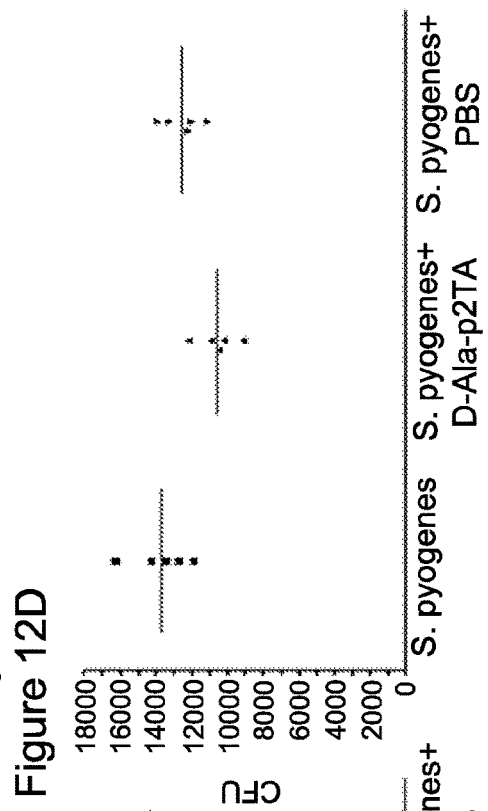
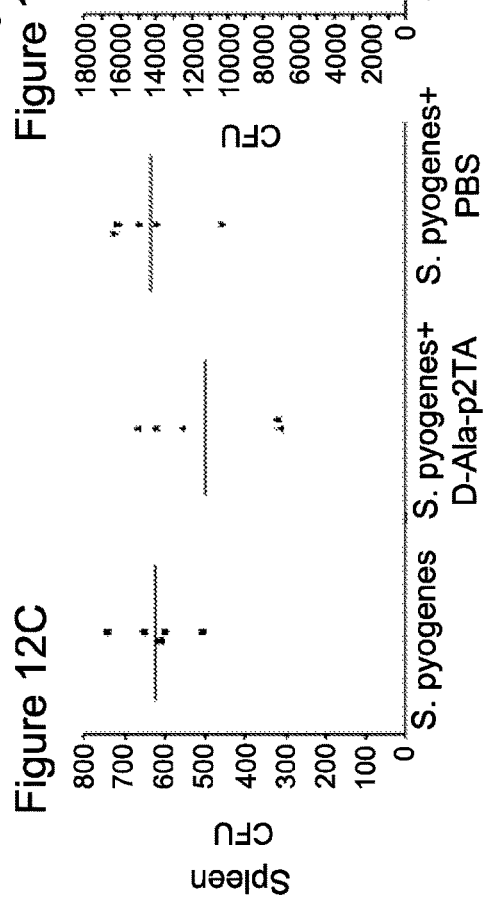
Figure 12A
Figure 12B
Figure 12C
Figure 12D

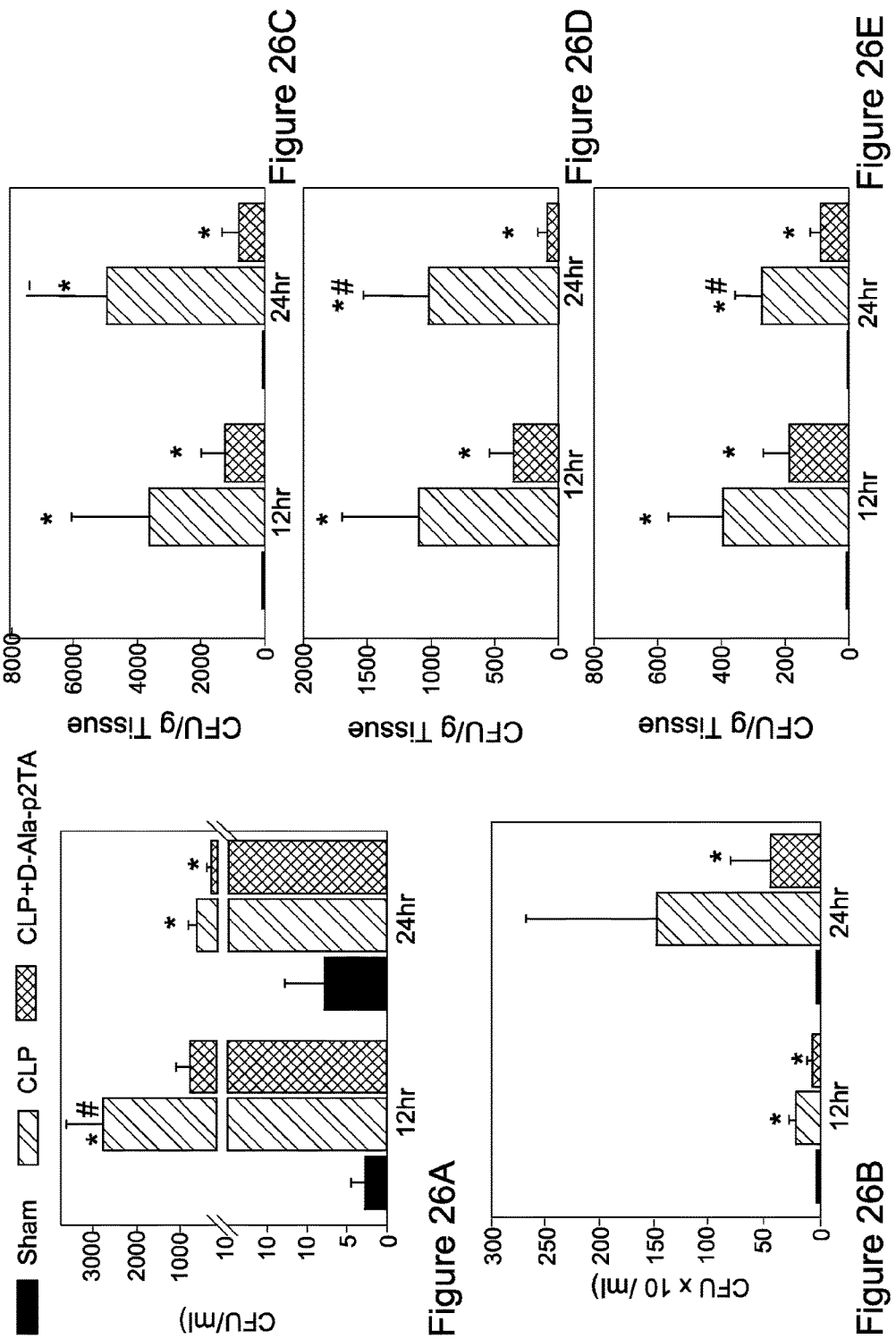

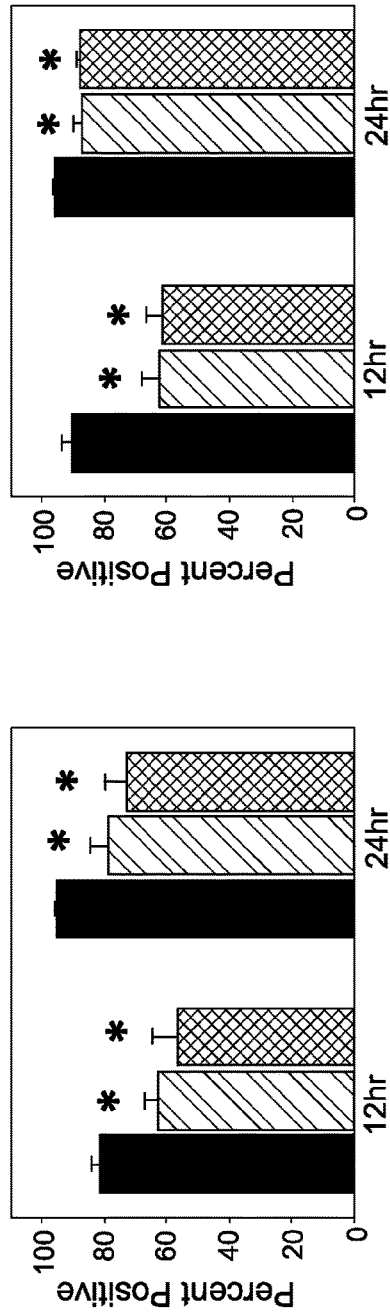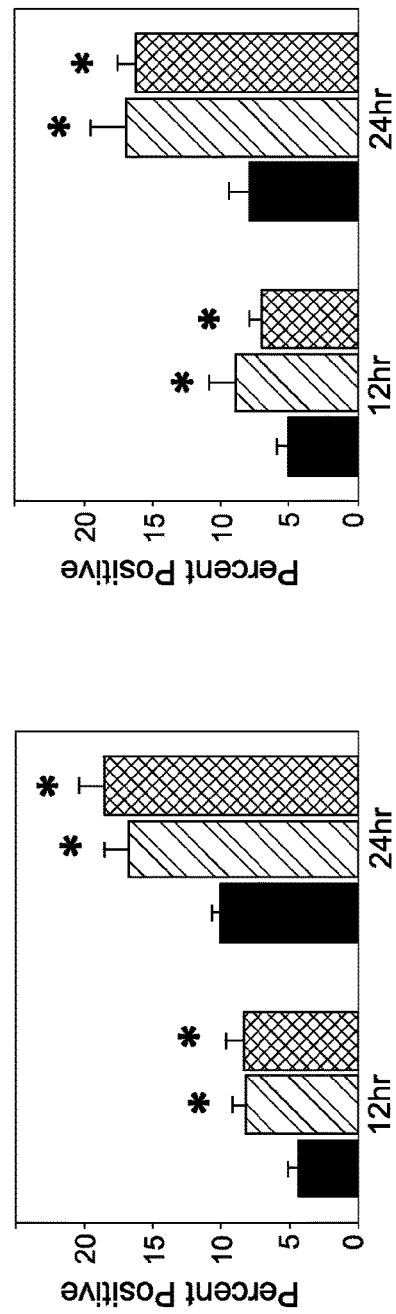
Figure 29A
Figure 29B
Figure 29C
Figure 29D

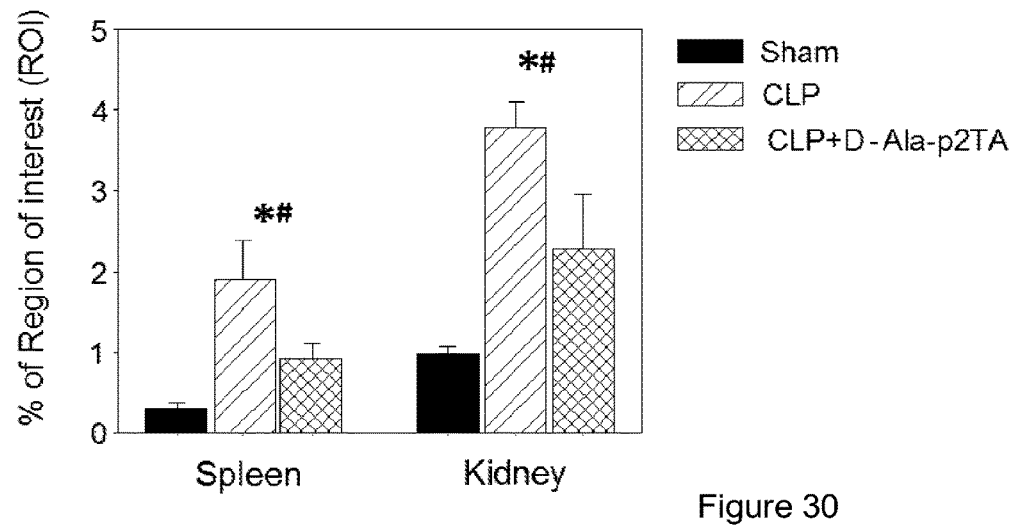
Figure 30
Figure 31A
Figure 31B
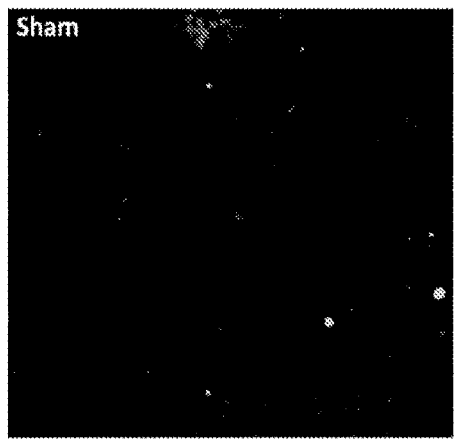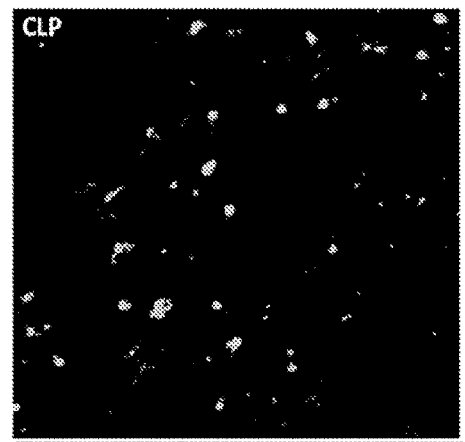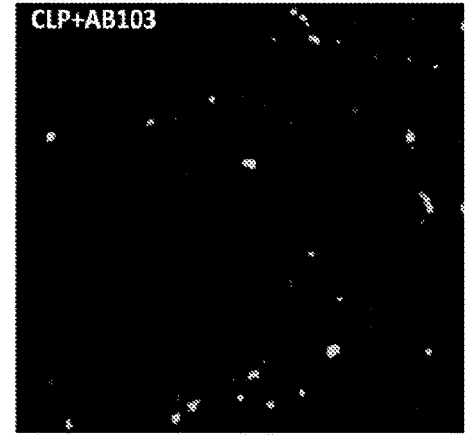
Figure 31C

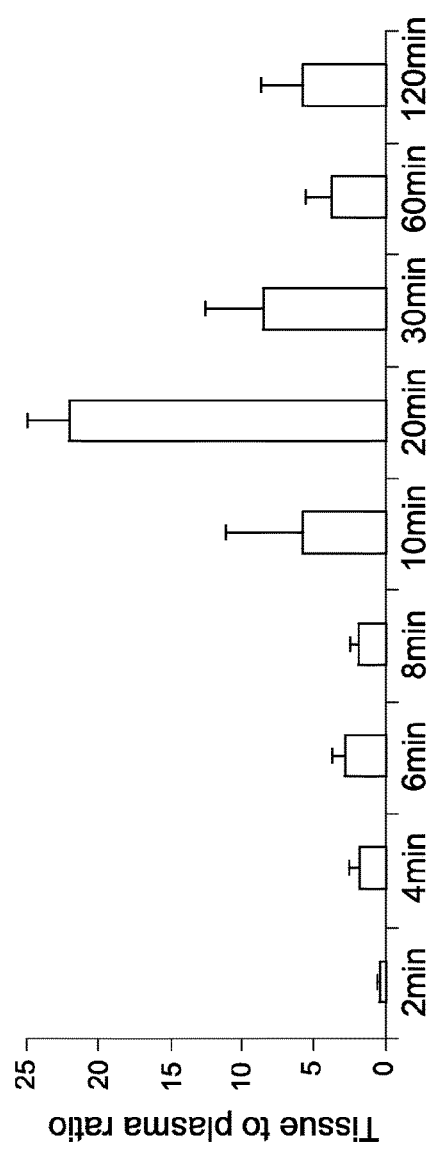
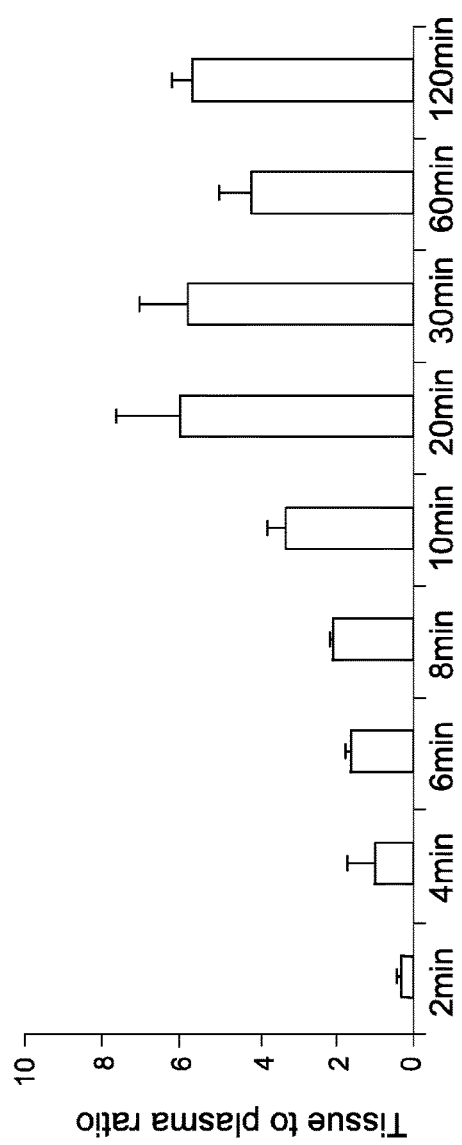
Figure 35A
Figure 35B

SYNTHETIC PEPTIDES FOR TREATMENT OF BACTERIAL INFECTIONS

FIELD OF THE INVENTION

Disclosed herein are peptides and methods for treating bacterial infections.

BACKGROUND OF THE INVENTION

Throughout this application, various publications are referenced by Arabic numerals within parentheses. Full citations for these publications may be found in the Prior Art section of the specification.

Severe bacterial infections caused by Gram negative or Gram positive bacteria, or by a mixture thereof, including sepsis, are a major cause of morbidity and mortality worldwide, despite the availability of potent antimicrobial agents and advances in supportive care [1].

Localized infections caused by Gram-positive bacteria, such as *Streptococcus pyogenes* (*S. pyogenes*) and *Staphylococcus aureus* (*S. aureus*) are often complicated by manifestations of systemic toxicity, including fever and hypotension, which may progress to sepsis and lethal septic/toxic shock. These types of bacteria may secrete exotoxin proteins, or superantigens (SAgs), which include staphylococcal enterotoxins SEA-SEE, toxic shock syndrome toxin 1 (TSST-1) and the streptococcal pyrogenic exotoxins SPEA and SPEC [2-7], which may trigger an excessive cellular immune response.

For example, Necrotizing Soft Tissue Infection (NSTI) is an acute, rapidly progressive severe skin infection that involves both the superficial fascia and subcutaneous fat and is characterized by pain at the infected site and systemic toxicity, including multi-organ injury. The infection may occur either spontaneously or following trauma. Since infections of this type respond to antibiotics poorly, aggressive surgical intervention to remove necrotic tissue is mandatory. Notwithstanding treatment, the mortality rate is currently approximately 10-20%. While there is no common bacterial etiology, several bacterial species, including *S. aureus*, Clostridia species, enterobacteriaciae and non-clostridial anaerobes are those most frequently identified, sometimes as a mixed or multi-pathogenic infection. Currently, there are no available approved drug products for this indication and therefore, there is a significant unmet medical need for effective therapies.

Consequently, there have been concerted efforts to develop adjunctive therapies that could ameliorate the effects of severe infections and reduce mortality. The availability of agents that can either neutralize bacterial virulent factors and/or enhance host defense may, particularly in conjunction with antibiotic therapy, improve the therapy of these infections.

Inflammation-induced lymphocyte apoptosis or pyroptosis by bacterial toxins has been shown to be a major cause of immunodepression and lethality in experimental infection models and in endotoxin- and superantigen-induced toxic shock models. Recent evidence indicates that blockade of co-stimulatory signals including CD40 and/or CD 80/86 might reduce mortality in experimental intra-abdominal sepsis [8].

The peptide p2TA disclosed herein was previously reported to block superantigen-mediated induction of inflammatory cytokines in human peripheral blood mononuclear cells and to block superantigen-mediated lethality in mice [9, 10].

PRIOR ART

References considered to be relevant as background to the presently disclosed subject matter are listed below:

[1] Dellinger, R. P., et al. (2008) Crit Care Med, 36(1):296-327.
[2] Sriskandan, S., et al. (1996) J Infect Dis, 173:1399-1407.
[3] Unnikrishnan, M., et al. (2002) J Immunol, 169:2561-2569.
[4] Unnikrishnan, M., et al. (2001) Microb Pathog, 31:109-114.
[5] Arad G. et al. (2000) Nat Med, 6:414-421.
[6] Lynskey, N. N., et al. (2011) Curr Opin Infect Dis, 24: 196-202.
[7] Llewelyn, M., et al. (2002) Lancet Infect Dis, 2: 156-162.
[8] Nolan, A., et al. (2008) Am J Respir Crit Care Med, 177:301-308.
[9] WO 2004/087196.
[10] Arad, G. et al. (2011) *PLoS Biol*, September; 9(9): e1001149.
[11] Chung, C. S., et al. (2007) Apoptosis, 12:1143-1153.
[12] Chung, C. S., et al. (2010) Shock, 34(2): 150-161.
[13] Kurupati P. et al. (2010) *Mol Microbiol,* 76(01387-1397.
[14] Cunningham, M. W. (2000) *Clin Microbiol Rev,* 13(2): 470-511.
[15] Bremell, T. et al. (1991) Infect. Immun. 59:2615-2623.
[16] Liu, Z-Q. et al. (2001) Arthritis Res. 3:375-380.

Acknowledgement of the above references herein is not to be inferred as meaning that these are in any way relevant to the patentability of the presently disclosed subject matter.

SUMMARY OF THE INVENTION

Provided herein is a peptide consisting of the amino acid sequence SPMLVAYD as denoted by SEQ ID NO:1, also denoted as p2TA, or any functional derivative, fragment, salt or ester thereof, for use in a method for the treatment of at least one of infection and acute inflammation associated therewith in a human subject in need of such treatment, wherein said peptide is administered to said subject in an amount of from about 0.025 mg to about 1.0 mg peptide/kg body weight of said subject. Additionally or alternatively, said peptide is administered to said subject in an amount of from about 0.1 mg to about 0.75 mg peptide/kg body weight of said subject. Additionally or alternatively, said peptide is administered to said subject in an amount of from about 0.25 mg to about 0.5 mg peptide/kg body weight of said subject.

In the above and other embodiments of the disclosed subject matter, said said derivative can be a peptide consisting of the amino acid sequence (D-A)SPMLVAYD(D-A) as denoted by SEQ ID NO:2, also denoted as D-Ala-p2TA.

In a second aspect of the present disclosure there is provided a peptide consisting of the amino acid sequence SPMLVAYD as denoted by SEQ ID NO:1, also denoted as p2TA, or any functional derivative, fragment, salt or ester thereof, for use in a method for at least one of preventing worsening, arresting and ameliorating damage emanating from or associated with at least one of infection and acute inflammation associated therewith, induced by at least one of Gram-positive bacteria, Gram-negative bacteria, polymicrobial infection and bacterial toxins, in a human subject in need thereof, wherein said peptide is administered to said subject in an amount of from about 0.025 mg to about 1.0 mg peptide/kg body weight of said subject. Additionally or alternatively, said peptide is administered to said subject in an amount of from about 0.1 mg to about 0.75 mg peptide/kg body weight of said subject. Additionally or alternatively, said peptide is administered to said subject in an amount of from about 0.25 mg to about 0.5 mg peptide/kg body weight of said subject.

In the above of other embodiments of said second aspect of the disclosed subject matter said derivative can be a peptide consisting of the amino acid sequence (D-A)SPM-LVAYD(D-A) as denoted by SEQ ID NO:2, also denoted as D-Ala-p2TA.

In the above and all other aspects and embodiments of the disclosed subject matter, said at least one of infection and acute inflammation associated therewith can be induced by at least one of Gram-positive bacteria, Gram-negative bacteria, polymicrobial infection, bacterial toxins and other toxic bacterial components.

In the above and all other aspects and embodiments of the disclosed subject matter said Gram-negative bacteria can be any one of proteobacteria, *Escherichia coli*, *Salmonella*, *Shigella*, Entero-bacteriaceae, *Pseudomonas*, *Moraxella*, *Helicobacter*, *Bdellovibrio*, *Stenotrophomonas*, acetic acid bacteria, *Legionella*, alpha-proteobacteria, *Wolbachia*, Gram-negative *cocci*, *Neisseria* species, *neisseria gonorrhoeae*, *neisseria*, *meningitidis*, *Moraxella catarrhalis*, Gram-negative *bacilli*, *Hemophilus influenzae*, *Klebsiella pneumoniae*, *Legionella pneumophila*, *Pseudomonas aeruginosa*, *Proteus mirabilis*, *Enterobacter cloacae*, *Serratia marcescens*, *Helicobacter pylori*, *Salmonella enteritidis*, *Salmonella typhi*, *Acinetobacter baumannii*, *Francisella tularemia*, *Vibrio*, *vulnificus*, *cholerae*, *fluvialis*, *parahemolyticus*, *alginolyticus*, *Photobacter damsela*, *Aeromonas hydrophila*, *Clostridium perfringens*, *Clostridium histolyticum*, *Porphyromonas/prevotella* sp. *Prevotella Intermedia*, *Prevotella Buccae*, *Prevotella* sp., *Bacteroides uniformis* and NDM-1 bacterial strains, said Gram-positive bacteria can be any one of Group A *streptococcus*, *S. pyogenes*, *S. pneumonia*, Group B strep, *Enterococcus faecalis*, Group D *streptococcus*, Group G *streptococcus*, *Streptococcus viridans*, *Streptococcus milleri*, *Propionibacterium* sp., *Enterococcus faecium*, *Peptostreptococcus* sp., *Streptococcus Microaerophilic*, *Lactobacillus* sp., *Staphylococcus Epidermis* and *Staphylococcus aureus*, said polymicrobial infection can be induced by Gram-positive bacteria, Gram-negative bacteria, or a combination thereof, and said toxic bacterial components can be any one of exotoxins, endotoxins, superantigen toxins, pathogen associated molecular patterns (PAMPs), Damage Associated Molecular Pattern molecules (DAMPs), lipopolysaccharides, peptidoglycans or toxic components thereof, molecules that are associated with groups of pathogens that are recognized by cells of the innate immune system and molecules that are associated with groups of pathogens that are recognized by Toll-like receptors (TLRs).

In the above and all other embodiments and aspects of the presently disclosed subject matter, said damage can be systemic damage or damage at the infection site, and can exhibited by any one of Necrotizing Soft tissue Infection (NSTI), polymicrobial intra-abdominal infection and burns, but is not limited thereto, and said damage can result in at least one of multi-organ failure, sepsis, severe sepsis, septic arthritis and septic shock.

In the above and all other aspects and embodiments of the disclosed subject matter, said administration can be, but is not limited to, any one of oral administration, intravenous, intramuscular, intraperitoneal, intratechal or subcutaneous injection, intrarectal administration, intranasal administration, ocular administration and topical administration.

In the above and all other aspects and embodiments of the disclosed subject matter, said peptide can be administered at any suitable time post onset of said at least one of infection and acute inflammation associated therewith, for example, but not limited to immediately following, or within from about 30 minutes to about 72 hours following, or within from about 30 minutes to about 7 days following said onset of said infection or acute inflammation associated therewith.

In the above and all other aspects and embodiments of the disclosed subject matter, said methods can further comprise administering to said subject a therapeutically effective amount of at least one additional therapeutically active agent and/or supportive standard of care treatment. Said at least one additional therapeutically active agent can be any one of antibacterial agents, antiviral agents, antifungal agents, antibiotic agents, bacteriostatic and bacteriocidal agents, steroids and antimicrobial agents, administered at suitable dose, which can be a suboptimal dose or a therapeutic dose. Said supportive standard of care treatment is at least one of ventilation, surgery, wound care, hyperbaric oxygen, IVIG (intravenous immunoglobulins), cortico-steroids, plasmapheresis, negative pressure wound therapy (vac dressings) and activated protein C. The said peptide and said additional therapeutically effective agent can be administered simultaneously.

Alternatively and additionally, said peptide and said at least one additional therapeutically effective agent can be administered at different time points, at different intervals between administrations, for different durations of time, and/or in a different order. The said interval between administration of said peptide and said additional therapeutically effective agent can be between 0 to 72 hours.

In the above and all other aspects and embodiments of the disclosed subject matter, said peptide can be comprised in a pharmaceutical composition, said composition comprising at least one of physiologically compatible additives, carriers, diluents and excipients.

In the above aspects and embodiments of the disclosed subject matter, the peptide can be administered by a single administration.

In a third aspect, the present disclosure provides for a peptide consisting of the amino acid sequence SPMLVAYD as denoted by SEQ ID NO:1, also denoted as p2TA, or any functional derivative, fragment, salt or ester thereof, for use in a method for the treatment of at least one of infection and acute inflammation associated therewith in a human subject in need of such treatment, wherein said method comprises a single administration to said subject of a therapeutically effective amount of said peptide. The said derivative can be but is not limited to a peptide consisting of the amino acid sequence (D-A)SPMLVAYD(D-A) as denoted by SEQ ID NO:2, also denoted as D-Ala-p2TA.

In a fourth aspect, the present disclosure provides for a peptide consisting of the amino acid sequence SPMLVAYD as denoted by SEQ ID NO:1, also denoted as p2TA, or any functional derivative, fragment, salt or ester thereof, for use in a method for at least one of preventing worsening, arresting and ameliorating damage emanating from or associated with infection or acute inflammation associated therewith induced by at least one of Gram-positive bacteria, Gram-negative bacteria, polymicrobial infection and bacterial toxins in a human subject in need thereof, said method comprising a single administration to said subject of a therapeutically effective amount of said peptide or any functional derivative, functional fragment, salt or ester thereof. The said derivative can be but is not limited to a peptide consisting of the amino acid sequence (D-A)SPM-LVAYD(D-A) as denoted by SEQ ID NO:2, also denoted as D-Ala-p2TA.

In all embodiments of the said third and fourth aspects as well as other aspects and embodiments of the disclosed subject matter, the said therapeutically effective amount can be from about 0.025 mg to about 1.0 mg peptide/kg body weight, for example from about 0.1 mg to about 0.75 mg peptide/kg body weight, such as from about 0.25 mg to about 0.5 mg peptide/kg body weight of said subject.

Other aspects and embodiments of the disclosed subject matter will become apparent as the description proceeds.

BRIEF DESCRIPTION OF THE DRAWINGS

In order to understand the disclosed subject matter and to realize how it may be carried out in practice, embodiments will now be described, by way of non-limiting example only, with reference to the accompanying drawings, in which:

FIG. 10 includes graphs demonstrating cytokine levels in mice infected with S. pyogenes and treated with D-Ala-p2TA.

FIG. 10A-1 is a graph demonstrating the effect on IFN-γ; FIG. 10A-2 is a graph demonstrating the effect on IL-17A; FIG. 10A-3 is a graph demonstrating the effect on TNF-α; and FIG. 10A-4 is a graph demonstrating the effect on IL-1β.

FIG. 10B-1 is a graph demonstrating the effect on KC, which is the mouse ortholog of IL-8; FIG. 10B-2 is a graph demonstrating the effect on IL-6; FIG. 10B-3 is a graph demonstrating the effect on RANTES; and FIG. 10B-4 is a graph demonstrating the effect on MCP-1.

FIG. 11 is a graphical representation of serum cytokine levels in mice infected with S. pyogenes.

FIG. 11A includes graphs representing serum level of interferon-gamma (IFN-γ) in mice infected intramuscularly with S. pyogenes in the absence of any further treatment or where the mice where treated with the peptide D-Ala-p2TA at 12 (FIG. 11A-1), 24 (FIG. 11A-2), 48 (FIG. 11A-3) and 72 (FIG. 11A-4) hours post-infection.

FIG. 11D-1 is a graph demonstrating the level of cytokines at 48 h post infection; and FIG. 11D-2 is a graph demonstrating the level of cytokines at 72 h post infection.

FIG. 12 includes graphs representing bacterial counts in muscle (FIG. 12A and FIG. 12B) and spleen (FIG. 12C and FIG. 12D), of mice infected with S. pyogenes and treated with D-Ala-p2TA, at 24 (Fig. A, Fig. C) and 48 (Fig. B, Fig. D) hours post infection.

FIG. 14 includes micrographs of mouse stained muscle sections at 48 hours (FIG. 14A and FIG. 14B) and 72 hours (FIG. 14C; FIG. 14B and FIG. 14D are micrographs of mouse stained muscle sections post S. pyogenes infection which were not treated.

FIG. 15 Graphical representations of serum antibody titers against SPE A, B and C. Antibody titers against streptococcal pyrogenic exotoxins A, B, and C were measured at 5 (A-C, n=5) and 14 (D-F, n=20) days after intramuscular infection with S. pyogenes. None of the infected, untreated mice survived over 5 days.

FIG. 25 includes graphs demonstrating the effect of D-Ala-p2TA (administered without antibiotics at 2 hours post CLP) on cytokine levels in the plasma (Blood—Left panels A-C) and peritoneal fluid (Right panels D-F) at 12 and 24 hours post CLP.

FIG. 26 includes graphs demonstrating that D-Ala-p2TA (administered without antibiotics at 2 hours post CLP) facilitates removal of bacteria, measured by CFU, from tissues and organs of CLP animals. FIG. 26A is a graph demonstrating CFU per milliliter measure in blood at 12 and 24 hours post CLP; FIG. 26B is a graph demonstrating CFU ($\times 10^4$) per milliliter measure in peritoneal fluid at 12 and 24 hours post CLP; FIG. 26C is a graph demonstrating CFU per gram tissue, measure in spleen at 12 and 24 hours post CLP; FIG. 26D CFU per gram tissue, measure in liver at 12 and 24 hours post CLP and FIG. 26E is a graph demonstrating CFU per gram tissue, measure in kidney at 12 and 24 hours post CLP.

FIG. 27 includes graphs demonstrating reduced polymorph nuclear cells (PMN) infiltration into key organs post CLP, measured by MPO activity at 12 and 24 hours post CLP. D-Ala-p2TA was administered without antibiotics at 2 hours post CLP.

FIG. 29 includes graphs demonstrating the effect of D-Ala-p2TA on CD28 expression after CLP. Surface expression of CD28 as assessed by flow cytometry showed significant reduction of levels on splenic (FIG. 29A) and blood (FIG. 29C) CD3+T lymphocytes at 12 and 24 hours post CLP, with and without treatment by the D-Ala-p2TA peptide. While splenic (FIG. 29B) and blood (FIG. 29D) Gr1+ myeloid cells showed increased expression following CLP, no effect was observed by the D-Ala-p2TA peptide treatment. *P<0.05, versus sham; Mean±SEM; n=5-8 mice/group.

FIG. 30 is a graph demonstrating reduced apoptosis levels in kidney and spleen at 24 hours post CLP, following treatment with D-Ala-p2TA (administered without antibiotics at 2 hours post CLP). *P<0.05, versus sham; #, P<0.05, versus C57BL/6 CLP. *P<0.05, versus sham; # P<0.05, versus D-Ala-p2TA peptide-treated CLP group. Mean±SEM; n=4-6 mice/group.

FIG. 31 is a micrograph demonstrating (by TUNEL staining) the reduced apoptosis in spleen at 24 hours post CLP. D-Ala-p2TA was administered without antibiotics at 2 hours post CLP. FIG. 31A is a micrograph demonstrating staining in Sham; FIG. 31B is a micrograph demonstrating staining in untreated CLP; and FIG. 31C is a micrograph demonstrating staining in D-Ala-p2TA treated post CLP.

FIG. 35 includes graphs showing the tissue-to-plasma ratio (Mean±SD) after a single IV administration of the peptide D-Ala-p2TA, in which the valine residue is replaced by [valine-$^{14}$C] (5 mg/kg), to male Balb/c mice. FIG. 35A: lymph nodes to plasma ratio over the first 2 hours post systemic administration. FIG. 35B: spleen-to-plasma ratio over the first 2 hours post systemic administration.

DETAILED DESCRIPTION OF THE INVENTION

Definitions

Figure 1B:
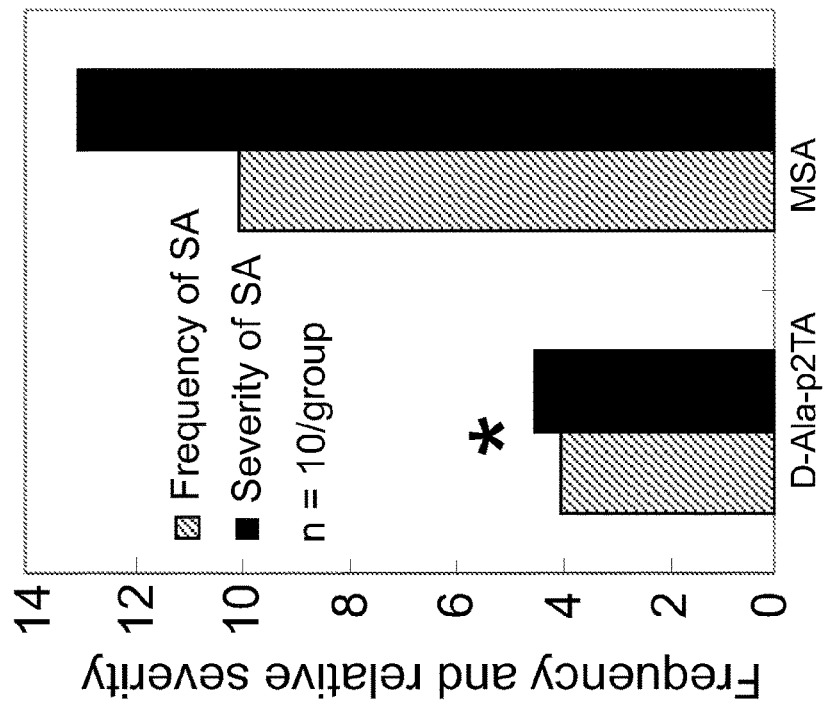
FIG. 1 includes graphs demonstrating that D-Ala-p2TA treatment can protect mice from septic arthritis resulting from live S. aureus infection (FIG. 1A) or from exposure to staphylococcal peptidoglycans (FIG. 1B). Abbreviations: SA denotes septic arthritis and MSA denotes mouse serum albumin.

The term "infection" as used herein is to be taken to mean the colonization of a host organism by bacterial pathogens, which may be at least one of Gram-positive bacteria, Gram-negative bacteria or a mixture of both Gram-positive and Gram-negative bacteria, as well as toxic components thereof.

The term "polymicrobial infection" as used herein is to be taken to mean an infection consisting of/induced by several species of bacteria. The bacterial infection may be caused by a mixture of Gram-positive bacteria, by a mixture of Gram-negative bacteria or by a mixture of both Gram-positive and Gram-negative bacteria. A polymicrobial infection can also be caused by a mixture of aerobic bacteria, anaerobic bacteria or both.

In some embodiments the infection or acute inflammation state is induced by Gram-negative bacteria. Infections can be induced not only by bacteria, but also by toxic bacterial components. Gram-negative bacteria include but are not limited to *E. coli*, and other *Helicobacter, Stenotrophomonas*, Bdellovibrio, *Legionella* and alpha-proteobacteria. More specifically, Gram-negative bacteria which are of special medical relevance include, but are not limited to cocci, such as *Neisseria* species such as *Neisseria gonorrhoeae* (which causes sexually transmitted disease) and *Neisseria, meningitidis* (which causes meningitis), and also *Moraxella catarrhalis* which causes respiratory symptoms. Gram-negative include species which primarily cause respiratory problems (*Hemophilus influenzae, Klebsiella pneumoniae, Legionella pneumophila, Pseudomonas aeruginosa*), urinary problems (*E. coli, Proteus mirabilis, Enterobacter cloacae, Serratia marcescens*), and gastrointestinal problems (*Helicobacter pylori, Salmonella enteritidis, Salmonella typhi*). Gram-negative bacteria associated with nosocomial infections include *Acinetobacter baumannii*, which cause bacteremia, secondary meningitis, and ventilator-associated pneumonia in intensive-care units of hospital establishments. Other bacteria include *Francisella tularemia* that can cause lethal respiratory infection, *Vibrio* species including *vulnificus, cholerae, fluvialis, parahemolyticus, alginolyticus* and *damsel*, (*Photobacter damsela*), *Aeromonas hydrophila, Clostridium perfringens*, or any of the highly antibiotic resistant NDM-1 bacterial strains. This group also includes *Porphyromonas/prevotella* sp. *Clostridium histolyticum, Prevotella Intermedia, Prevotella Buccae, Prevotella* sp. and *Bacteroides uniformis*, In some embodiments, the infection or acute inflammation state is induced by Gram-negative bacteria selected from the group consisting of proteobacteria, *Escherichia coli, Salmonella, Shigella*, Enterobacteriaceae, *Pseudomonas, Moraxella, Helicobacter, Bdellovibrio, Stenotrophomonas*, acetic acid bacteria, *Legionella*, alpha-proteobacteria, *Wolbachia*, Gram-negative *cocci, Neisseria* species, *neisseria gonorrhoeae, neisseria, meningitidis, Moraxella catarrhalis*, Gram-negative *bacilli, Hemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi, Acinetobacter baumannii, Francisella tularemia, Vibrio, vulnificus, cholerae, fluvialis, parahemolyticus, alginolyticus, Photobacter damsela, Aeromonas hydrophila, Clostridium perfringens, Clostridium histolyticum, Porphyromonas/prevotella* sp. *Prevotella Intermedia, Prevotella Buccae, Prevotella* sp., *Bacteroides uniformis* and NDM-1 bacterial strains.

Bacterial pathogens also include Gram-positive bacteria, such as, but not limited to Group A *streptococcus* (such as *S. pyogenes*), *S. pneumonia*, Group B *streptococcus, Enterococcus faecalis* (Group D strep), Group G strep, *Streptococcus viridans, Streptococcus milleri Propionibacterium* sp. *Enterococcus faecium, Peptostreptococcus* sp. *Streptococcus Microaerophilic, Lactobacillus* sp. *Staphylococcus Epidermis* and *Staphylococcus aureus*.

Bacterial infections may also involve several species of bacterial pathogens rather than a single bacterial species. These infections are also known as complex, complicated, mixed, dual, secondary, synergistic, concurrent, polymicrobial, co-infections (some examples of which are presented herein in the model of intra-abdominal infection).

Toxic bacterial components include bacterial toxins, such as exotoxins and endotoxins. Examples of bacterial exotoxins, usually associates with Gram-positive bacteria are proteins like Staphylococcal enterotoxin B (SEB), Staphylococcal enterotoxin A (SEA), Toxic shock syndrome toxin 1 (TSST-1), to name but few. Other toxic components belong to Pathogen Associated Molecular Patterns (PAMPs), molecules that are associated with groups of pathogens that are recognized by cells of the innate immune system, particularly by Toll-like receptors (TLRs). Examples of PAMPs are endotoxins, associated with Gram-negative bacteria, such as LPSs (lipopolysaccharides) or the toxic component/s thereof, such as Lipid A. Other toxic components may be Damage Associated Molecular Pattern molecules (DAMPs), which are molecules that can initiate and perpetuate immune response in the noninfectious inflammatory response. Examples of DAMPS are peptidoglycans, associated with Gram-positive bacteria, heat shock proteins and their fragments, hyaluronan fragments, purine metabolites, etc.

In some embodiments, the toxic bacterial components are selected from the group consisting of exotoxins, endotoxins, superantigen toxins, pathogen associated molecular patterns (PAMPs), Damage Associated Molecular Pattern molecules (DAMPs), peptidoglycans, lipopolysaccharides or toxic components thereof, molecules that are associated with groups of pathogens that are recognized by cells of the innate immune system and molecules that are associated with groups of pathogens that are recognized by Toll-like receptors (TLRs).

Infection conditions include, but are not limited to *S. aureus* infection causing septic arthritis, as presented herein. Bacterial arthritis (or septic arthritis) is a rapidly progressive and highly destructive joint disease in humans. Clinical symptoms of septic arthritis include red, swollen, warm, painful and dysfunctional joints [15, 16]. Septic arthritis develops when bacteria spread through the bloodstream to a joint and it may also occur when the joint is directly infected with a microorganism from an injury or during surgery. The most common sites for this type of infection are the knee and hip. A relevant experimental model for such infection is the *S. aureus* knee joint infection in mice.

Other infection conditions include, but are not limited to Necrotizing Soft Tissue Infection (NSTI). It is to be understood that NSTI is a descriptive term, which includes a variety of distinctive clinical diagnoses representing the most severe types of infections involving the skin, skin structures and soft tissue. Necrotizing fasciitis due to group A streptococcal infection or non group A infection, bacterial synergistic gangrene, Clostridial gas gangrene, Fournier's gangrene, and hemolytic streptococcal gangrene are non-limiting examples of the distinct clinical entities which share clinical features, including severe local tissue necrosis, systemic toxemia and bacteremia and have a high mortality rate, due to multi-organ failure. A non-limiting example is *S. pyogenes* infection, presented herein. A relevant experimental model for such infection is the *S. pyogenes* thigh infection in mice.

Surgery, diabetes, obesity, intravenous drug use, peripheral vascular disease and immunosuppression are often cited as risk factors for NSTI, however, a large proportion of cases have no predisposing reason for their infection. The key clinical feature is the presence of necrosis confined to the subcutaneous fascial tissues and often also in the deep fascial layers, fat, nerves, arteries and veins and while this may not always be apparent by physical examination or imaging studies, it identifies the patient who needs immediate surgical exploration and debridement.

Without being bound by theory, the pathogenesis of NSTI is thought to be related to the excessive local release of bacterial toxins and inflammatory cytokines. The excessive local inflammatory response spreads into the systemic circulation causing systemic inflammatory response syndrome (SIRS), which can lead to refractory shock and multi-organ failure.

Infection conditions may also include respiratory (lung) infection (for example by *S. pneumonia*) and intraperitoneal (or severe intra-abdominal infections (as, for example, presented in the following examples in both the Cecal Ligation and Puncture (CLP) model and *E. coli* peritonitis model).

The term "acute inflammation associated therewith" as used herein means part of the complex acute biological response of the organism to harmful stimuli, such as infection by bacterial pathogens and/or components thereof according to the present disclosure.

Additional conditions encompassed by the present invention are associated with activation of the innate immune response, are trauma or traumatic injury (that are not initially associated with infection) and its associated tissue damage that are recognized at the cell level via receptor-mediated detection of intracellular proteins released by the dead cells. These components are termed Damage associated molecular pattern molecules (DAMPs) that can initiate and perpetuate immune response in the noninfectious inflammatory response. They serve as the "Signal 0" similar to Pathogen-Associated Molecular Pattern molecules (PAMPs) that drive initiation and perpetuation of the inflammatory response. Examples of DAMPs include nuclear or cytosolic proteins with defined intracellular function that, when released outside the cell or exposed on the surface of the cell following tissue injury, move from a reducing to an oxidizing milieu resulting in their functional denaturation.

In a particular embodiment, the bacterial-induced condition is sepsis, a serious condition that is characterized by a whole-body inflammatory state (also referred to as SIRS) and the presence of a known or suspected infection. The body may develop this inflammatory response by the immune system to bacteria presence in the blood, urine, lungs, skin, or other tissues. Sepsis is commonly known as blood poisoning or septicemia. Severe sepsis is the systemic inflammatory response, plus infection, plus the presence of at least one organ dysfunction. Septicemia (also sometimes referred to as bacteremia) refers to the presence of pathogenic organisms in the bloodstream, leading to sepsis.

Infection conditions also include conditions induced by or involving flesh-eating bacteria such as group A streptococci, and complications involved, for example incapacitation (vomiting, nausea) or gangrene, by *S. aureus* leading to septic arthritis (joint inflammation and destruction), as well as many others.

The term "single administration" as used herein refers to an administration of a drug that is provided as a one dose given once, at a certain time point.

The term "therapeutically active agent" encompasses, but is not limited to antibacterial agents, antiviral agents, antifungal agents, antibiotic agents, bacteriostatic and bactericidal agents, steroids and antimicrobial agents.

The term "antibiotic agent" is to be taken to mean any therapeutic agent that is effective against bacterial infections, including antibiotic, antibacterial, bacteriostatic, bactericidal, antimicrobial agents, which may be product of nature, semi-synthetic or synthetic. Exemplary and non-limiting antibiotic agents are moxifloxacin or ceftriaxone.

An embodiment of the presently disclosed subject matter is based on the finding that administration of a therapeutically effective amount of the peptide p2TA as herein defined or a functional derivative thereof, was effective in the treatment of an infection and/or an acute inflammation associated therewith in a human subject in need thereof, whether given as a stand-alone therapy or in combination with least one additional therapeutic agent and/or standard of care treatment.

The peptide herein designated p2TA, consists of the amino acid sequence SPMLVAYD, as denoted by SEQ ID NO:1. Functional derivatives of said peptide are also encompassed within the present disclosure.

As a non-limiting example, a derivative of this peptide is the peptide p2TA, which comprises the amino acid sequence SPMLVAYD, abutted at both termini with D-alanine residues. The resulting derivative is a peptide consisting of the amino acid sequence (D-A)SPMLVAYD(D-A), as denoted by SEQ ID NO:2 that is also referred to herein as "D-Ala-p2TA".

Without wishing to be bound by theory, the addition of D-alanine residues at both termini improves the protease resistance of the peptide. Other derivatives of p2TA are contemplated within the scope of the present invention, as detailed below. Therefore, the term p2TA as used herein encompasses the peptide of SEQ ID NO:1, as well as its derivatives, for example, but not limited to the derivative D-Ala-p2TA denoted by SEQ ID NO:2.

Thus, presently disclosed is a peptide consisting of the amino acid sequence SPMLVAYD as denoted by SEQ ID NO:1, also denoted as p2TA, or any functional derivative, fragment, salt or ester thereof, for use in a method for the treatment of at least one of infection and acute inflammation associated therewith in a human subject in need of such treatment, wherein said peptide is administered to said subject in an amount of from about 0.025 mg to about 1.0 mg peptide/kg body weight of said subject.

The term "peptide" is to be taken to mean also its fragments, derivatives and functional derivatives. Thus, for example, derivatives, e.g. the D-Ala-p2TA peptide, may be referred to as "the peptide".

The terms "fragments", "derivatives" and "functional derivatives" as used herein mean peptides comprising the amino acid sequence of any one of SEQ ID NO:1 or 2, with any insertions, deletions, substitutions and modifications to the peptide that do not interfere with their ability to therapeutically affect bacterial and other infections, as well as inflammations associated therewith, as described herein. A derivative should maintain a minimal homology to said SEQ ID NO:1, e.g. 95%, 90%, 80%, 70%, 60% and so forth.

By the term "insertions", as used herein is meant any addition of at least one amino acid residues to the peptides of the invention and up to 20 amino acid residues, for example between 20 to 1 amino acid residues, more specifically between 1 to 10 amino acid residues, for example 1, 2, 3, 4 or 5 amino acid residues.

The presently disclosed peptides can be coupled through their N-terminus to a lauryl-cysteine (LC) residue and/or through their C-terminus to a cysteine (C) residue.

The peptides may all be positively charged, negatively charged or neutral. In addition, they may be in the form of a dimer, a multimer or in a constrained conformation, which can be attained by internal bridges, short-range cyclizations, extension or other chemical modifications.

Further, the peptides may be extended at the N- and/or C-terminus thereof with various identical or different amino acid residues. As an example for such extension, the peptide may be extended at the N-terminus and/or C-terminus thereof with identical or different hydrophobic amino acid residue/s which may be naturally occurring or synthetic amino acid residue/s. A specific synthetic amino acid residue is D-alanine. An additional example for such an extension may be provided by peptides extended both at the N- and/or C-terminus thereof with a cysteine residue. Naturally, such an extension may lead to a constrained conformation due to Cys-Cys cyclization resulting from the formation of a disulfide bond. Another example may be the incorporation of an N-terminal lysyl-palmitoyl tail, the lysine serving as linker and the palmitic acid as a hydrophobic anchor. In addition, the peptides may be extended by aromatic amino acid residue/s, which may be naturally occurring or synthetic amino acid residue/s, for example a specific aromatic amino acid residue may be tryptophan. The peptides may be extended at the N- and/or C-terminus thereof with various identical or different organic moieties which are not naturally occurring or synthetic amino acids. As an example for such extension, the peptide may be extended at the N- and/or C-terminus thereof with an N-acetyl group. For every single peptide sequence used by the invention and disclosed herein, this invention includes the corresponding retro-inverse sequence wherein the direction of the peptide chain has been inverted and wherein all the amino acids belong to the D-series. Longer peptides, in which the basic epitope sequence, which comprises part or all of the amino acid sequence as denoted by SEQ ID NO:1, or abutted with D-Ala residues at both termini (SEQ ID NO:2, also termed D-Ala-p2TA) or other derivatives, are also contemplated within the scope of the presently disclosed subject matter.

In some embodiments, presently disclosed is a peptide consisting of the amino acid sequence (D-A)SPMLVAYD (D-A), as denoted by SEQ ID NO:2, also denoted as D-Ala-p2TA for use in a method for the treatment of at least one of infection and acute inflammation associated therewith in a human subject in need of such treatment, wherein said peptide is administered to said subject in an amount of from about 0.025 mg to about 1.0 mg peptide/kg body weight of said subject.

The therapeutically effective amount (or amounts) of the peptide for purposes herein defined is determined by such considerations as are known in the art in order to cure or at least arrest or at least alleviate the medical condition. According to the present disclosure, the peptide according to the invention is administered to said subject in an amount of from about 0.025 mg to about 1.0 mg peptide/kg body weight of said subject.

The peptide according to the invention may administered in an amount from 0.025 mg to 1.0 mg peptide/kg body weight of said subject, such as 0.05-1.0, 0.1-1.0, 0.2-1.0, 0.3-1.0, 0.4-1.0, 0.5-1.0, 0.6-1.0, 0.7-1.0, 0.8-1.0, 0.9-1.0, 0.05-0.7, 0.1-0.7, 0.2-0.7, 0.3-0.7, 0.4-0.7, 0.5-0.7, 0.6-0.7, 0.05-0.4, 0.05-0.3, 0.05-0.2. Specifically, the therapeutically effective amount may be any one of 0.025, 0.05, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975 or 1.0 mg peptide/kg body weight.

In the above and other embodiments of the disclosed subject matter, the peptide according to the present disclosure is administered to said human subject in an amount of from about 0.1 mg to about 0.75 mg peptide/kg body weight of said subject.

In the above and other embodiments of the disclosed subject matter, the peptide according to the present disclosure is administered to said human subject in an amount of from about 0.25 mg to about 0.5 mg peptide/kg body weight of said subject.

It is to be noted that the amount of the peptide to be administered may vary by about 5-25%, in consideration of the molecular weight and other features of a specific peptide.

In the above and other embodiments of the disclosed subject matter, said at least one of infection and acute inflammation associated therewith is induced by at least one of Gram-positive bacteria, Gram-negative bacteria, polymicrobial infection, bacterial toxins and other toxic bacterial components.

In the above and other embodiments of the disclosed subject matter, the Gram-negative bacteria are selected from the group consisting of proteobacteria, *Escherichia coli*, *Salmonella*, *Shigella*, Enterobacteriaceae, *Pseudomonas*, *Moraxella*, *Helicobacter*, *Bdellovibrio*, *Stenotrophomonas*, acetic acid bacteria, *Legionella*, alpha-proteobacteria, *Wolbachia*, Gram-negative *cocci*, *Neisseria* species, *neisseria gonorrhoeae, neisseria, meningitidis, Moraxella catarrhalis*, Gram-negative *bacilli, Hemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi, Acinetobacter baumannii, Francisella* tularemia, *Vibrio, vulnificus, cholerae, fluvialis, parahemolyticus, alginolyticus, Photobacter damsela, Aeromonas hydrophila, Clostridium perfringens, Clostridium histolyticum, Porphyromonas/prevotella* sp. *Prevotella Intermedia, Prevotella Buccae, Prevotella* sp., *Bacteroides uniformis* and NDM-1 bacterial strains, wherein said Gram-positive bacteria are selected from the group consisting of Group A *streptococcus, S. pyogenes, S. pneumonia*, Group B strep, *Enterococcus faecalis*, Group D *streptococcus*, Group G *streptococcus, Streptococcus viridans, Streptococcus milleri, Propionibacterium* sp., *Enterococcus faecium, Peptostreptococcus* sp., *Streptococcus Microaerophilic, Lactobacillus* sp., *Staphylococcus Epidermis* and *Staphylococcus aureus*, wherein said polymicrobial infection is induced by Gram-positive bacteria, Gram-negative bacteria, or a combination thereof, and wherein said toxic bacterial components are selected from the group consisting of exotoxins, endotoxins, superantigen toxins, pathogen associated molecular patterns (PAMPs), Damage Associated Molecular Pattern molecules (DAMPs), lipopolysaccharides or toxic components thereof, molecules that are associated with groups of pathogens that are recognized by cells of the innate immune system and molecules that are associated with groups of pathogens that are recognized by Toll-like receptors (TLRs).

In another of its aspects, the present disclosure provides a peptide consisting of the amino acid sequence SPMLVAYD as denoted by SEQ ID NO:1, also denoted as p2TA, or any functional derivative, fragment, salt or ester thereof, for use in a method for at least one of preventing worsening, arresting and ameliorating damage emanating from or associated with at least one of infection and acute inflammation associated therewith, induced by at least one of Gram-positive bacteria, Gram-negative bacteria, polymicrobial infection and bacterial toxins, in a human subject in need thereof, wherein said peptide is administered to said subject in an amount of from about 0.025 mg to about 1.0 mg peptide/kg body weight of said subject.

In the above and other embodiments of the disclosed subject matter, the peptide for use in a method for at least one of preventing worsening, arresting and ameliorating damage emanating from or associated with at least one of infection and acute inflammation associated therewith, induced by at least one of Gram-positive bacteria, Gram-negative bacteria, polymicrobial infection and bacterial toxins, in a human subject in need thereof, a peptide consisting of the amino acid sequence (D-A)SPMLVAYD(D-A) as denoted by SEQ ID NO:2, also denoted as D-Ala-p2TA.

In the above and other embodiments of the disclosed subject matter, said damage is systemic damage or damage at the infection site. In the above and other embodiments of the disclosed subject matter, the said damage is exhibited by Necrotizing Soft tissue Infection (NSTI), by polymicrobial intra-abdominal infection, or by burns, and wherein said damage may result in at least one of multi-organ failure, sepsis, severe sepsis, septic arthritis and septic shock.

As used herein, the term "human subject in need" is to be taken to mean a human suffering from at least one of infection and acute inflammation associated therewith as herein defined.

The term "treat" or forms thereof as herein defined means to prevent worsening or arrest or alleviate or cure the patient's disease or condition.

In the above and other embodiments of the disclosed subject matter, administration may be performed by any of the following routes: oral administration, intravenous, intramuscular, intraperitoneal, intratechal or subcutaneous injection; intrarectal administration; intranasal administration, ocular administration or topical administration. Intravenous administration may be continuous administration, specifically over a period of from about 10 to about 30 minutes. Intravenous administration may alternatively be push administration.

In the above and other embodiments of the disclosed subject matter, the peptide for use according to the present disclosure may be administered at a suitable time post onset of said at least one of infection and acute inflammation associated therewith. Alternatively or additionally, the peptide for use according to the present disclosure may be administered immediately following the onset of said infection or acute inflammation associated therewith. Still alternatively or additionally, the peptide for use according to the present disclosure may be administered within from about 30 minutes to about 72 hours following said onset of said infection or acute inflammation associated therewith. Still alternatively or additionally, the peptide for use according to the present disclosure may be administered within from about 30 minutes to about 7 days following said onset of said infection or acute inflammation associated therewith.

The term "onset" refers to any time point between the time of infection of said human subject or the time of beginning of its clinical manifestation or the manifestation of acute inflammation associated with or resulting from said infection and the time of diagnosis of any of the infection and inflammation by a skilled member of attending medical staff, and any time therebetween or thereafter, in which treatment in accordance with the present disclosure is professionally assigned to said subject.

In the above and other embodiments of the disclosed subject matter, said other therapeutically active agent can be any one of antibacterial agent, antiviral agent, antifungal agent, antibiotic agent, bacteriostatic and bacteriocidal agent, steroid and antimicrobial agent, which can be administered at either a suboptimal dose or a therapeutic dose.

In the above and other embodiments of the disclosed subject matter, said standard of care treatment can include, but is not limited to, at least one of ventilation, surgery, wound care, hyperbaric oxygen, IVIG (intravenous immunoglobulins), corticosteroids, plasmapheresis, negative pressure wound therapy (vac dressings) and activated protein C.

In the above and other embodiments of the disclosed subject matter, said peptide and said additional other therapeutically effective agent are administered simultaneously. Alternatively or additionally, said peptide and said additional other therapeutically effective agent are administered at different time points, at different intervals between administrations, for different durations of time, or in a different order. Said interval between the administration of said peptide and said additional other therapeutically effective agent may be between 0-72 hours.

For example, treatment may commence with administration of both the peptide and the additional agent, and administration of the additional agent may be ceased before or after the administration of the peptide.

In the above and other embodiments of the disclosed subject matter, the peptide of the presently disclosed subject matter is comprised in a pharmaceutical composition, said composition comprising at least one of physiologically compatible additives, carriers, diluents and excipients.

The pharmaceutical compositions of the presently disclosed subject matter generally comprise a buffering agent, an agent which adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The carrier, additive, excipient and/or diluent do not interfere with the activity of the peptide.

The term "salts" as herein defined refers to a pharmaceutically acceptable salt, e.g., non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the active compounds used herein with a suitable organic or inorganic acid.

The term "ester" as herein defined refers to a pharmaceutically acceptable ester, e.g. esters which retain, upon hydrolysis of the ester bond, the biological effectiveness and properties of the carboxylic acid or alcohol and are not biologically or otherwise undesirable. Generally, ester formation can be accomplished via conventional synthetic techniques.

In specific embodiments, said pharmaceutical composition can be in a sustained- or controlled-release form, or in a combined sustained/controlled-release and immediate release forms.

In the above and other embodiments of the disclosed subject matter, the peptide may be comprised in a pharmaceutical unit dosage form, said dosage form optionally further comprising at least one of physiologically compatible additives, carriers, peptide stabilizers, diluents and excipients. For example, said dosage form may optionally further comprise protease inhibitors.

The peptide p2TA, as well as derivatives thereof, for example but not limited to D-Ala-p2TA, have been shown to have a very short half-life in the plasma of experimental animals, such as mice and pigs, as well as in humans, as shown in a Phase 1 study performed in healthy volunteers. The documented half-life in all these species was in the range of 1-2.6 minutes. Notwithstanding this short half-life, the peptide exhibited a remarkable and lasting effect, by only a single administration of an effective dose thereof.

In a further aspect of the present disclosure, disclosed is a peptide consisting of the amino acid sequence SPMLVAYD as denoted by SEQ ID NO:1, also denoted as p2TA, or any functional derivative, fragment, salt or ester thereof, for use in a method for the treatment of at least one of infection and acute inflammation associated therewith in a human subject in need of such treatment, wherein said method comprises a single administration to said subject of a therapeutically effective amount of said peptide.

The term "single administration" as used herein refers to an administration of a drug that is provided as one dose, given once, at a certain time point.

In the above and other embodiments of the presently disclosed subject matter, said derivative can be a peptide comprising the amino acid sequence SPMLVAYD (SEQ ID NO:1), abutted at both its termini with D-alanine residues, thus a peptide consisting of the amino acid sequence (D-A) SPMLVAYD(D-A), as denoted by SEQ ID NO:2, also denoted as D-Ala-p2TA.

In yet a further aspect of the disclosure, disclosed herein is a peptide consisting of the amino acid sequence SPMLVAYD as denoted by SEQ ID NO:1, also denoted as p2TA, or any functional derivative, fragment, salt or ester thereof, including, but not limited to the derivative D-Ala-p2TA as denoted by SEQ ID NO:2, for use in a method for at least one of preventing worsening, arresting and ameliorating damage emanating from or associated with infection or acute inflammation associated therewith induced by at least one of Gram-positive bacteria, Gram-negative bacteria, polymicrobial infection and bacterial toxins in a human subject in need thereof, said method comprising a single administration to said subject of a therapeutically effective amount of said peptide or any functional derivative, functional fragment, salt or ester thereof.

Also in these aspects of the presently disclosed subject matter, wherein treatment comprises a single administration of said peptide or functional fragments and derivatives thereof, as in the above and other embodiments, the said therapeutically effective amount can be from about 0.025 mg to about 1.0 mg peptide/kg body weight of said subject. Thus, the amount can be from 0.025 mg to 1.0 mg peptide/kg body weight of said subject, such as 0.05-1.0, 0.1-1.0, 0.2-1.0, 0.3-1.0, 0.4-1.0, 0.5-1.0, 0.6-1.0, 0.7-1.0, 0.8-1.0, 0.9-1.0, 0.05-0.7, 0.1-0.7, 0.2-0.7, 0.3-0.7, 0.4-0.7, 0.5-0.7, 0.6-0.7, 0.05-0.4, 0.05-0.3, 0.05-0.2. Specifically, the therapeutically effective amount may be any one of 0.025, 0.05, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975 or 1.0 mg peptide/kg body weight. Alternatively or additionally the peptide according to the present disclosure is administered to said human subject in an amount of from about 0.1 mg to about 0.75 mg peptide/kg body weight of said subject or in an amount of from about 0.25 mg to about 0.5 mg peptide/kg body weight of said subject. As will be shown in the following Examples, the inventors have found that treatment with the peptide D-Ala-p2TA, given at yet a narrower range of doses, was optimal under a wide range of conditions.

Also in these aspects of the presently disclosed subject matter, wherein treatment comprises a single administration of said peptide or functional fragments and derivatives thereof, as in the above and other embodiments, the at least one of infection and acute inflammation associated therewith is induced by at least one of Gram-positive bacteria, Gram-negative bacteria, polymicrobial infection, bacterial toxins and other toxic bacterial components, all, mutatis mutandis as defined above.

Also in these aspects of the presently disclosed subject matter, wherein treatment comprises a single administration of said peptide or functional fragments and derivatives thereof, as in the above and other embodiments, said damage is mutatis mutandis systemic damage or damage at the infection site. The said damage can be exhibited by Necrotizing Soft tissue Infection (NSTI), by polymicrobial intra-abdominal infection, or by burns, and wherein said damage may result in multi-organ failure, severe sepsis, septic arthritis or septic shock.

Also in these aspects of the presently disclosed subject matter, wherein treatment comprises a single administration of said peptide or functional fragments and derivatives thereof, as in the above and other embodiments, said administration is, mutatis mutandis by any of the routes selected from the group consisting of oral administration, intravenous, intramuscular, intraperitoneal, intratechal or subcutaneous injection, intrarectal administration, intranasal administration, ocular administration and topical administration. The time of administration can be as defined for the above and other embodiments of the disclosed subject matter.

Also in these aspects of the presently disclosed subject matter, wherein treatment comprises a single administration of said peptide or functional fragments and derivatives thereof, as in the above and other embodiments, said method can mutatis mutandis further comprise administering to said subject at least one of a therapeutically effective amount of at least one additional therapeutically active agent and supportive standard of care treatment, as detailed above.

Thus, said at least one additional therapeutically active agent is selected from the group consisting of antibacterial agents, antiviral agents, antifungal agents, antibiotic agents, bacteriostatic and bacteriocidal agents, steroids and antimicrobial agents, administered at either a suboptimal dose or a therapeutic dose, and said supportive standard of care treatment is selected from ventilation, surgery, wound care, hyperbaric oxygen, IVIG (intravenous immunoglobulins), corticosteroids, plasmapheresis, negative pressure wound therapy (vac dressings) and activated protein C. The disclosed peptide and said additional therapeutically effective agent are administered simultaneously, or at different time points, at a different interval between administrations, for different durations of time, or in a different order. The said interval between administrations of said peptide and said additional therapeutically effective agent is between 0 to 72 hours.

Also disclosed herein is a method for the treatment of at least one of infection and acute inflammation associated therewith in a human subject in need of such treatment, said method comprising the administration to said subject of a therapeutically effective amount of a peptide consisting of the amino acid sequence SPMLVAYD as denoted by SEQ ID NO:1, also denoted as p2TA, or any functional derivative, fragment, salt or ester thereof, wherein said therapeutically effective amount is from about 0.025 mg to about 1.0 mg peptide/kg body weight of said subject. The said derivatives can be but is not limited to peptide consisting of the amino acid sequence (D-A)SPMLVAYD(D-A) as denoted by SEQ ID NO:2, also denoted as D-Ala-p2TA.

In addition, disclosed herein is a method for at least one of preventing worsening, arresting and ameliorating damage emanating from or associated with at least one of infection and acute inflammation associated therewith, induced by at least one of Gram-positive bacteria, Gram-negative bacteria, polymicrobial infection and bacterial toxins, in a human subject in need thereof, said method comprises administering a therapeutically effective amount of a peptide consisting of the amino acid sequence SPMLVAYD as denoted by SEQ ID NO:1, also denoted as p2TA, or any functional derivative, fragment, salt or ester thereof, wherein said therapeutically effective amount is from about 0.025 mg to about 1.0 mg peptide/kg body weight of said subject. The said derivative can be but is not limited to a peptide consisting of the amino acid sequence (D-A)SPMLVAYD(D-A) as denoted by SEQ ID NO:2, also denoted as D-Ala-p2TA.

Also disclosed herein is a method for the treatment of at least one of infection and acute inflammation associated therewith in a human subject in need of such treatment, comprising the administration of a peptide consisting of the amino acid sequence SPMLVAYD as denoted by SEQ ID NO:1, also denoted as p2TA, or any functional derivative, fragment, salt or ester thereof, wherein said method comprises a single administration to said subject of a therapeutically effective amount of said peptide. The said derivative can be but is not limited to a peptide consisting of the amino acid sequence (D-A)SPMLVAYD(D-A) as denoted by SEQ ID NO:2, also denoted D-Ala-p2TA.

Further disclosed herein is a method for at least one of preventing worsening, arresting and ameliorating damage emanating from or associated with infection or acute inflammation associated therewith induced by at least one of Gram-positive bacteria, Gram-negative bacteria, polymicrobial infection and bacterial toxins in a human subject in need thereof, said method comprising a single administration to said subject of a therapeutically effective amount of a peptide consisting of the amino acid sequence SPMLVAYD as denoted by SEQ ID NO:1, also denoted as p2TA, or any functional derivative, fragment, salt or ester thereof. The said derivative can be but is not limited to a peptide consisting of the amino acid sequence (D-A)SPMLVAYD(D-A) as denoted by SEQ ID NO:2, also denoted D-Ala-p2TA.

As mentioned, the said damage can be systemic damage or damage at the infection site. As will be shown in the following Examples, the peptide D-Ala-p2TA exhibited accumulation in lymphatic organs such as the lymph nodes and thymus (organs containing T cells), already at early time points post-administration, which may indicate, without being bound by theory, its compartmentalization and retention at its target sites.

The description of the above and other embodiments applies, mutatis mutandis, also to the presently disclosed methods of treatment.

The following examples are representative of techniques employed in carrying out aspects of the presently disclosed subject matter. It should be appreciated that while these techniques are exemplary of disclosed embodiments, those of skill in the art, in light of the present disclosure, will recognize that numerous modifications can be made without departing from the intended scope of the disclosure.

EXAMPLES

Experimental Procedures

Reagents

Unless otherwise stated, all chemical reagents were obtained from Sigma (St. Louis, Mo.). All superantigens and toxins were purchased from Toxin Technology, Sarasota, Fla.

Bacteria

The *E. coli* Lipopolysaccharide (LPS) 0111:B4 was obtained from List Biological Laboratories (Campbell, Calif.).

The *E. coli* strain O18:K1:H7, a clinically relevant Gram-negative bacterial isolate, was used for the peritonitis studies.

Staphylococcal peptidoglycans [16] were highly purified by Dr. Andrzej Tarkowski (University of Gothenburg, Sweden) and the *Staphylococcus aureus* strain LS-1 group, a Gram-positive bacterial isolate [15], was from Dr. Andrzej Tarkowski (University of Gothenburg, Sweden).

The Group A *Streptococcus* (GAS) *Streptococcus pyogenes* (*S. pyogenes*) strain (Scarlet fever serotype M1T1), is a clinical isolate, donated by Dr. Jonathan Cohen (Hammersmith Hospital, London, UK). This strain was previously shown to produce multiple superantigen exotoxins. The strain was cultured in Todd-Hewitt broth (Becton Dickinson) at 37° C. under aerobic conditions. The culture was allowed to grow until mid-log phase. The culture was centrifuged and washed twice with PBS. The desired number of bacteria was then resuspended in PBS for further use.

Animals

Specific pathogen-free female BALB/c mice (8-12 weeks) and CD1 outbred mice (6-8 week) were obtained from Charles River Laboratories (Wilmington, Mass.). All animal studies were approved by the Brown University and the University of Maryland Institutional Animal Care and Use Committees (IACUC) before experiments were initiated. The animals were housed in an IACUC-approved facility under BSL-2 safety conditions and were monitored by Brown University and University of Maryland veterinary staff.

In Example 1, male BALB/c mice (8 weeks) were obtained from ALAB (Stockholm, Sweden). All animal studies were approved by the Gothenburg University IACUC before experiments were initiated. The animals were housed in an IACUC-approved facility under BSL-2 safety conditions and were monitored by Gothenburg University veterinary staff.

Bacterial Counts in Organs

After euthanizing the infected mice, the local infection site (thigh muscle tissue), spleen and liver were harvested from each mouse. The weights of the organs were measured and the organs were then placed in tubes containing sterile PBS. The tissue samples were homogenized using Omni TH homogenizer and were then serially diluted in PBS. The different dilutions were plated on 5% sheep blood agar plates and the CFU/mg was determined for each tissue, in each testing group.

Antibodies Against Superantigens

To determine levels of immunoglobulin antibody against various superantigens, D-Ala-p2TA peptide-treated mice that had survived GAS challenge were euthanized. Cardiac blood was obtained, and serum was separated. Recombinant streptococcal pyrogenic exotoxin A (SPEA), streptococcal pyrogenic exotoxin B (SPEB), a protease and streptococcal virulence factor, or streptococcal pyrogenic exotoxin C (SPEC) dissolved in carbonate-bicarbonate buffer, pH 9.6, at a concentration of 10 µg/ml, were used to coat 96-well enzyme-linked immunosorbent assay microtiter plates. Nonspecific binding sites were blocked with 50% fetal calf serum (FCS) in PBS. Plates were washed with 0.05% Tween20 (Fisher Scientific, Pittsburgh, Mass.) in 0.5% FCS. Serum, diluted 1:100 in 1% FCS, was applied to the wells. Alkaline phosphatase-conjugated sheep IgG antibody against mouse or goat IgM antibody against mouse (Sigma) diluted 1:10,000 in 1% FCS was applied before addition of the substrate, p-nitrophenyl phosphate and determination of absorbance at 405 nm.

Immunohistochemistry

Muscle samples were sectioned, embedded and fixed at 5 µm, placed in 10 mM citrate buffer of pH 6.0, and heated for 10 min. Sections were incubated for 15 min in 3% hydrogen peroxide (Sigma-Aldrich) in methanol, washed with distilled water and PBS for 5 min each, permeabilized in 0.3% Triton (Sigma-Aldrich) for 15 min and in 0.1% Tween20 for 5 min, blocked in 10% normal goat serum in PBS for 1 hr at room temperature (RT), and then incubated with primary antibody-cleaved caspase-3 (Asp175) (Cell Signaling, Boston, Mass.) overnight at 4° C. After washing, sections were incubated with conjugated goat anti-rabbit IgG (Vector Laboratories, Burlingame, Calif.) for 1 hr at RT, then permeabilized by treatment twice with 0.1% Tween20 for 5 min, washed, and incubated for 1 hr at RT with R.T.U. Vectastain Elite ABC Reagent (Vector Laboratories), according to the manufacturer's protocol. After washing, the section was developed with diaminobenzidine substrate Ki, 3,3'-diaminobenzidine (Vector Laboratories), to give a brown to gray/black color. Slides were dehydrated in serial ethanol and xylene solution and permanently mounted. Images were digitally captured at ×100 magnification using an Olympus BX51 microscope. Quantification of cleaved caspase-3 staining was performed in a blinded manner by counting positive cells in multiple random microscope fields per tissue section.

Assessment of Phenotype and Apoptosis

Flow Cytometric Analysis was performed as follows: Splenocytes were stained with Allophycocyanin (APC)-labeled anti-CD3 (clone: 145-2C11, BioLegend, San Diego, Calif.), -F4/80 (clone: BM8, BioLegend), -CD4 (clone: GK1.5, e-Bioscience, Inc., San Diego, Calif.), -CD8 (clone: 53-6.7, e-Bioscience, Inc.), -B220 (clone: RA3-6B2, e-Bioscience, Inc.) or -Gr-1 (clone: RB6-8C5, e-Bioscience, Inc.) in combination with PE-labeled anti-CD28 (clone: 37.51, e-Bioscience, Inc.) for phenotype or Annexin V (BD Biosciences, San Diego, Calif.) for apoptosis. Blood cells were stained with anti-CD3 or -Gr-1 in combination with anti-CD28 for phenotype or Annexin V for apoptosis, and analyzed by BD FACSArray Bioanalyzer [11].

Peptide Synthesis

The peptide p2TA has the sequence SPMLVAYD, which is denoted by SEQ ID NO:1. The peptide D-Ala-p2TA has D-alanine residues added to both its N- and C-termini, to increase its stability and protease resistance (D-Ala-p2TA is also denoted by SEQ ID NO:2). The peptide was synthesized using fluoronyl-methoxycarbonyl chemistry [10]. A control scrambled peptide (D-Ala-Ala-Ser-Met-Asp-Tyr-Pro-Val-Leu-D-Ala, as also denoted by SEQ ID NO:3) was prepared as above.

Fresh stock solutions of 1 mg peptide/ml in phosphate-buffered saline (PBS) was prepared, and further diluted with PBS to desired working concentrations. Once dissolved, the peptides were used immediately.

Serum Chemistry

Serum from uninfected or infected mice treated with either PBS or the peptide D-Ala-p2TA, 5 days post-infection were analyzed for blood chemistry using creatinine, BUN, ALT, AST, alkaline $PO_4$ and bilirubin. The serum samples were analyzed by ANTECH diagnostics (Rockville, Md.).

Allogeneic Mixed Lymphocyte Reaction

Monocytes from healthy individuals were purified from PBMC using commercially available negative selection kits (Stemcell Technologies), and cultured in cRPMI supplemented with 50 ng/ml GM-CSF and 25 ng/ml IL-4 (both from R & D Systems) for 3 days to generate immature monocyte-derived dendritic cells (moDCs). moDCs were harvested from cultures, washed twice in cRPMI, and plated in triplicate wells of 96-well U-bottom culture plates (Denville Scientific, Inc.) at $2 \times 10^4$, $2 \times 10^3$, and $2 \times 10^2$ cells per well. Allogeneic responder PBMCs were added to each well at $2 \times 10^5$ cell/well in the absence and presence of 0.1, 1, or 10 µg/ml of the peptide D-Ala-p2TA in a final volume of 200 µl. The cells were incubated for 3 days at 37° C. in 5% $CO_2$, pulsed with 1.0 µCi tritiated thymidine (Perkin Elmer, Boston, Mass.) for 16 hours (also denoted hrs or hr), and harvested using an automated multiwell harvester (Tomtec, Orange, Conn.). The amount of tritiated thymidine incorporated into the responder cells was measured using the MicroBeta TriLux liquid scintillation counter (Wallac, Turku, Finland).

Murine Model of Septic Arthritis

The murine model of septic arthritis [15, 16] was used to assess the effect of the peptide D-Ala-p2TA on mice infected by live *S. aureus*. Mice received a single intra-articular injection of live *S. aureus* LS-1 (800 colony-forming units/knee joint). After 6, 12, and 24 hours, the mice were injected i.p. with either D-Ala-p2TA (200 ng/mouse) or mouse serum albumin (MSA) (200 ng/mouse). Alternatively, mice received a single intra-articular injection of purified staphylococcal peptidoglycans (25 micrograms/knee joint) together with D-Ala-p2TA (200 ng/knee joint) or MSA (200 ng/knee joint); after 6, 12, and 24 hours, the mice were injected i.p. with either D-Ala-p2TA (200 ng/mouse) or MSA (200 ng/mouse). All the mice were killed 72 hours after start of the experiment (i.e. intra-articular injections). All the joint sections were assessed blinded for severity of arthritis and joint destruction.

Lymphocyte Proliferation Assays

Isolated splenocytes were tested ex vivo taken from sham mice or CLP mice treated by the peptide D-Ala-p2TA or not-treated in lymphocyte proliferation assays. Splenocytes were stimulated with anti-CD3 alone or anti-CD3+anti-CD28 antibodies and cultured for 72 hours. Cell proliferation was then assessed using the CyQuant assay. The proliferation index was calculated as: absorbance of anti-CD3+anti-CD28 stimulation/Absorbance of anti-CD3 stimulation alone.

Cytokine Analysis

Mouse cytokine levels were measured in plasma and peritoneal fluid using a 16-multiplex immunoassay (Quansys Biosciences, Logan Utah). KC, Rantes (both were from R&D Systems, Minneapolis, Minn.), IL-3 (BD biosciences) and IL-17A (Biolegend) levels were measured in plasma, peritoneal fluid or tissue homogenates by the "sandwich enzyme-linked immunosorbent assay (ELISA)" technique using monoclonal antibody pairs and the mouse cytokine standards as described previously [12].

Statistics

All values are expressed as mean±standard deviation. Differences between groups were analyzed using Student's t-test by GraphPad Prism (Version 4.03 for Windows, GraphPad Software, San Diego, Calif.). Differences are considered significant at P<0.05.

Example 1

Figure 1A:
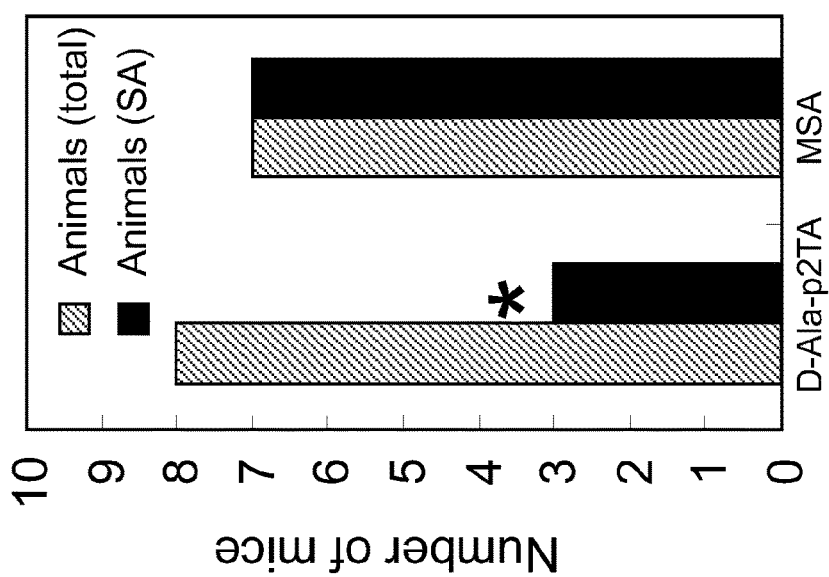

Murine Model of Septic Arthritis 1.1 the Peptide D-Ala-p2TA Reduces Septic Arthritis Induced by S. aureus Infection The peptide D-Ala-p2TA has been studied extensively in a model of S. aureus knee joint infection, considered a representative model of Gram-positive septic arthritis [15]. This model is used to study pathogenesis of S. aureus infection. Live bacteria, S. aureus LS-1 group, were injected intra-articularly into the knee joint and D-Ala-p2TA was injected i.p. 6, 12 and 24 hours later. At 72 hours after the intra-articular injections, all the joint sections were assessed blinded for severity of arthritis and joint destruction. As shown in FIG. 1A, in the control group, all the mice (7/7) that were treated with mouse serum albumin showed clear signs of septic arthritis. By contrast, of the 8 mice that were treated with D-Ala-p2TA, only 3 (38%) showed signs of septic arthritis (*, p<0.05).

1.2 the Peptide D-Ala-p2TA Reduces Septic Arthritis Induced by Staphylococcal Peptidoglycans The peptide D-Ala-p2TA has been studied extensively in a model of knee joint infection induced by highly purified staphylococcal peptidoglycans, considered a representative model of Gram-positive septic arthritis [16]. Staphylococcal peptidoglycans were injected intra-articularly into the knee joint together with D-Ala-p2TA or MSA; D-Ala-p2TA or mouse serum albumin (MSA) was injected 6, 12 and 24 hours later i.p. At 72 hours after the intra-articular injections, all the joint sections were assessed blinded for severity of arthritis and joint destruction. As shown in FIG. 1B, in the control group, all mice (10/10) that were treated i.p. with MSA showed clear signs of septic arthritis, with a severity index of 13 for this group. In contrast, out of the 10 mice that were treated with D-Ala-p2TA, only 4 (40%) showed signs of septic arthritis, and the cumulative severity score of joint destruction was reduced from 13 to 4.5 (35%) (*, p<0.05).

Example 2

Model of Soft Tissue Infection

The peptide D-Ala-p2TA has been studied extensively in a model of Gram-positive soft tissue infection, considered a representative model of Necrotizing Soft tissue infection (NSTI) [13, 14]. This is a model of a thigh infection with S. pyogenes, which is widely used to study its pathogenesis. S. pyogenes has an ability to spread rapidly at the site of infection and to disseminate systemically, and causes a range of invasive infections including necrotizing fasciitis. Many of the systemic features of profound shock that commonly accompany necrotizing fasciitis stem from bacterial release of exotoxins, including superantigens.

The ability of the peptide D-Ala-p2TA to increase overall survival in the presence of an invasive Gram-positive lethal bacterial infection (S. pyogenes) was evaluated when administered alone, at a single dose. Frozen S. pyogenes were plated onto Trypticase Soy agar supplemented with 5% sheep blood and incubated overnight at 37° C. under 5% $CO_2$. The overnight plates were carefully washed with Todd Hewitt broth supplemented with 0.5% yeast extract (THYE) to suspend the plate growth. The re-suspension was adjusted to a concentration of approximately $10^9$ CFU/ml ($A_{600\ nm}$=1.0) in THYE. The infecting inoculum was generated by diluting 1 mL overnight suspension into 9 mL THYE, creating a 10-fold dilution (approximately $1.0 \times 10^8$ CFU/ml) before administration to mice. BALB/c mice (6-8 weeks) were injected i.m., into the right thigh muscle of one hind leg with $1\text{-}1.5 \times 10^7$ CFU of S. pyogenes, in a volume of 0.1 ml.

2.1. Protection from Bacterial Infection Upon Delayed Treatment

Figure 2:
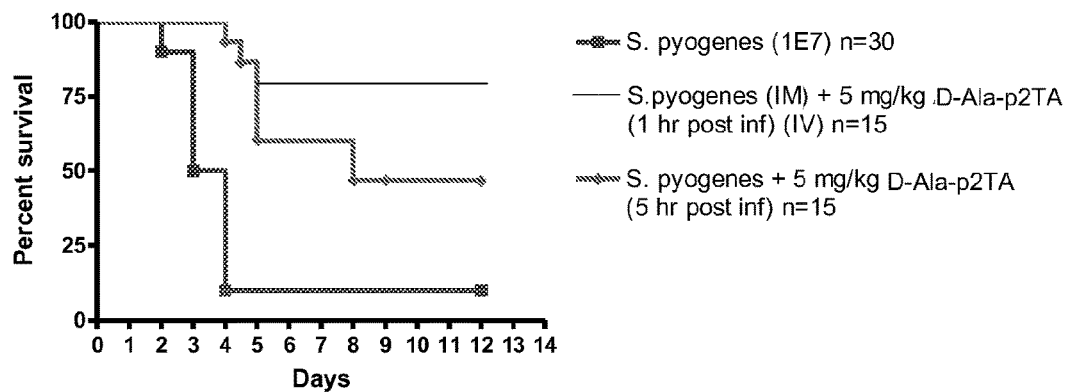
FIG. 2 is a Kaplan-Meier survival plot demonstrating that D-Ala-p2TA treatment can protect mice from established S. pyogenes infection at a delayed time points of one and five hours post infection.

To initially assess the effect of the peptide D-Ala-p2TA on established acute bacterial infection, the peptide D-Ala-p2TA was administered as a single intravenous dose of 5 mg/kg to groups of 15 infected mice at 1 hour or 5 hours post infection. As shown in FIG. 2, these administrations provided 80% and 50% survival rate, respectively. Statistical analysis indicated that for each of the treatment groups, p<0.05 as compared to the control non-treated group. These results indicate that after bacterial infection there is a time frame of at least 5 hours, during which a single administration of the peptide D-Ala-p2TA, without any additional antibiotic treatment may be beneficial. Importantly, the same dose of 5 mg/kg was an efficacious dose, whether given at the time of infection or as a delayed treatment, at 1 or 5 hours post infection.

2.2. Dose Response Under Delayed Treatment Conditions

Figure 3:
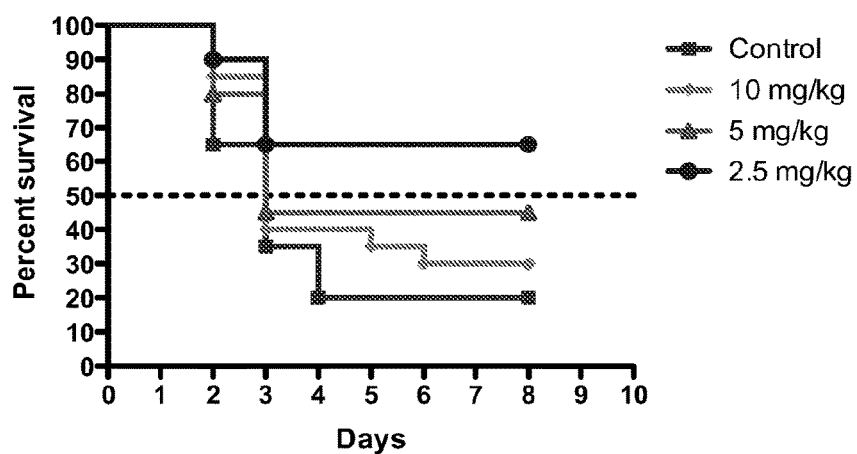
FIG. 3 is a Kaplan-Meier survival plot of S. pyogenes soft tissue infection of mice, a dose response, when D-Ala-p2TA is administered at the delayed time point of one hour post infection.

To assess the efficacy of different doses in protecting mice from lethal S. pyogenes infection, when administered as a delayed treatment, groups of 20 mice were treated with a single administration of the peptide D-Ala-p2TA given intravenously, at doses ranging from 2.5-10 mg/kg, given at 1 hour post infection. Survival was followed for 8 days following the infection, as shown in FIG. 3.

Survival curve analysis was carried out in GraphPad Prism (version 5) with Log rank test for trends to determine a difference between survival times. When a difference in trend was detected, Log rank tests were performed against control and treatments, to determine which treatments were different from their cohorts. A p value of <0.05 was the threshold for a significant result.

In the absence of any treatment, mortality occurred from day 2-4, culminating in final survival rate of 20%. Administration of 2.5 mg/kg was most efficacious, significantly increasing the survival rate by 3.25 fold as compared to control non-treated animals, and conferring 65% overall survival, with p<0.005 vs. control. The median survival times for this regimen were >8 days at 2.5 mg/kg and 3 days for the infection control, 5 mg/kg and 10 mg/kg. Doses of 5 and 10 mg/kg were less efficacious, increasing survival rates to 45% and 30%, respectively (with p<0.05 vs. 2.5 mg/kg), suggesting that under delayed treatment conditions, treatment with a dose of 2.5 mg/kg is optimal.

Figure 4:
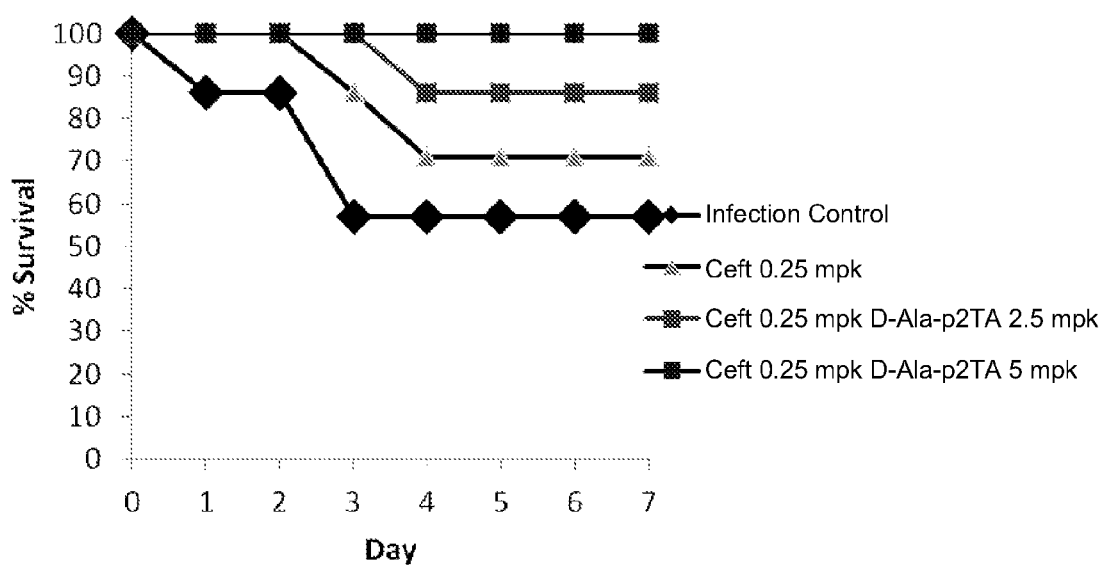
FIG. 4 is a Kaplan-Meier survival plot of BALB/c mice, demonstrating synergistic effect of D-Ala-p2TA and antibiotics at 36 hours post infection.

2.3. The Peptide D-Ala-p2TA Extends the Therapeutic Window of Antibiotics for Treating Established *S. pyogenes* Infection BALB/c mice (in groups of 10) were infected with *S. pyogenes*, under conditions where mortality started to occur already after one day and culminated in 57% overall survival after 7 days. As exemplified in FIG. 4, when this established infection was treated with antibiotics alone (ceftriaxone, 0.25 mg/kg) at a late time point post infection (36 hours), mortality is delayed and starts at day 3, and such treatment can provide partial protection, culminating in 70% survival. However, when both antibiotics and the peptide D-Ala-p2TA were given concomitantly at 36 hours post infection, survival proportions increased. A combined treatment of antibiotic and 2.5 mg/kg of peptide D-Ala-p2TA augmented survival to 86%, and a combined treatment of antibiotic and 5 mg/kg provided 100% protection, where none of the mice died. These results indicate that addition of a single dose of peptide D-Ala-p2TA to a standard antibiotic treatment can extend the existing therapeutic window of antibiotics, and confer full protection from lethal infection. Such a trait can be potentially important in clinical settings, where the antibiotic treatment is often given to established infections.

2.4 Improvement of Infection Signs at the Local Site of Infection

Figure 5:
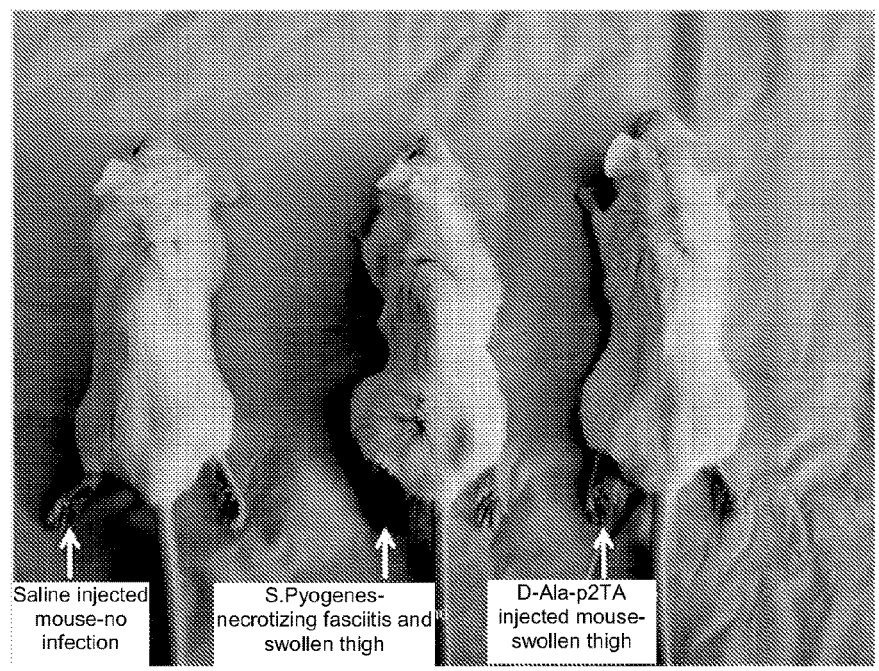
FIG. 5 is a picture documenting the Effect of D-Ala-p2TA on the local site of infection at 24 hours post S. pyogenes infection.

The major characteristic of soft tissue infection is a rapid progression of inflammation and necrosis at the infection site, resulting from bacterial virulent factors such as toxins and enzymes, as well as from release of cytokines. To evaluate whether treatment with the peptide D-Ala-p2TA has a direct effect on the local site of infection, the infection site was monitored at an early time point after infection. Balb/c mice were infected at the thigh of their left hind leg with *S. pyogenes*, and the peptide D-Ala-p2TA was administered as a delayed treatment at one hour post infection. As can be seen in FIG. 5, at 24 hours post infection, a substantial necrotic lesion can be detected that spread also to the foot pad of infected mice, which was not treated with peptide D-Ala-p2TA (see the mouse in the middle). However, mouse treated with peptide D-Ala-p2TA, showed no signs of inflammation and necrosis, and their footpad appears clean (see right mouse), similar to a foot pad of a control healthy mice injected with saline (left mouse).

These results indicate that the peptide D-Ala-p2TA can improve disease symptoms both locally at the site of infection as well as systemically, culminating in increased survival. Thus, D-Ala-p2TA not only blocks toxic shock caused by challenge with a single lethal dose of superantigen [4, 5], but also protects mice against live, replicating *S. pyogenes* that produce a variety of superantigens.

2.5. Dosing Regimen

To elucidate the optimal dosing regimen of the peptide D-Ala-p2TA when given as a single therapy that will provide the most favorable treatment effect, experiments were performed to follow the number of doses required for most advantageous treatment, the interval between doses, as well as the option to perform fractionation of each dose into smaller doses. These regimens were investigated in BALB/c mice infected with *S. pyogenes*, and treated at delayed time point post infection.

One Dose Versus Multiple Doses

Figure 6:
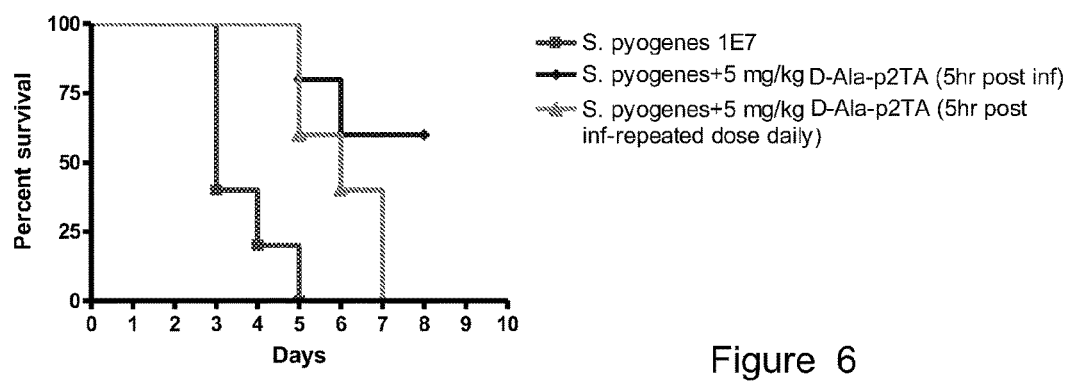
FIG. 6 is a Kaplan-Meier survival plot of BALB/c mice, demonstrating the efficacy of one vs. two doses of D-Ala-p2TA (at 5 mg/kg), given 5 hours post S. pyogenes infection.

The effect of one dose as compared to two doses was examined when treatment of mice (n=5) by the peptide D-Ala-p2TA at a dose of 5 mg/kg (given intravenously) was initiated at 5 hours after infection. A second dose, when applicable, was given 24 hours following the infection. Results are shown in FIG. 6 and indicate that without any treatment, mice started dying at day 3, and by day 5, 100% mortality was evident. Treatment with one dose of peptide D-Ala-p2TA provided 60% survival rate, while treatment with 2 daily doses had a substantial reduced effect as compared to a single dose, culminating in death of all animals at day 7, a rate that was slower than the death rate of infected animals that were not treated (with P<0.05 values between either of the treatment arms and the control).

Figure 7:
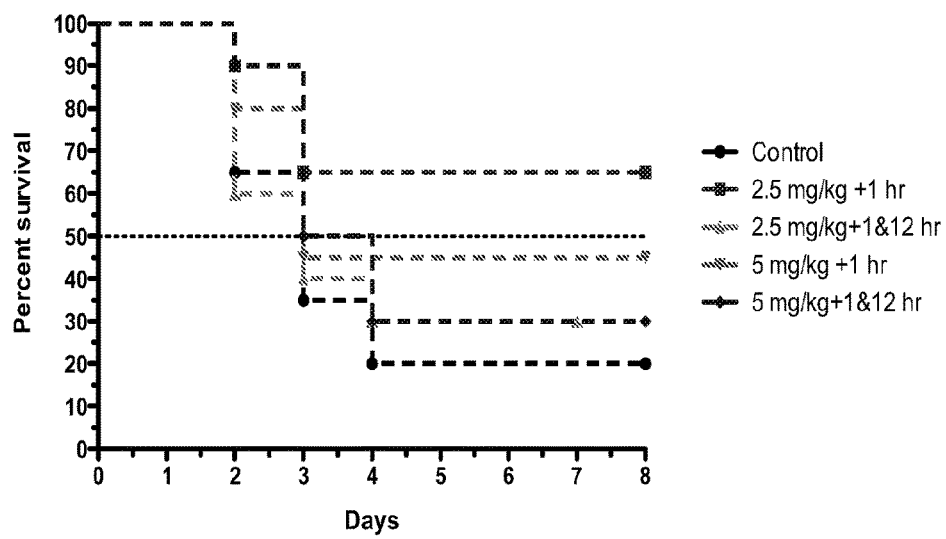
FIG. 7 is a Kaplan-Meier survival plot of BALB/c mice, demonstrating the efficacy of one vs. two doses of D-Ala-p2TA (2.5 mg/kg), given post S. pyogenes infection.

The effect of a single dose as compared to two doses was examined also under conditions where the first dose of treatment was initiated at 1 hour post infection, and the interval between the doses was 12 hours, as shown in FIG. 7. Two different doses were evaluated, 2.5 and 5 mg/kg. Control non-treated mice (n=20) exhibited 20% survival. Treatment with a single dose of 2.5 mg/kg (in groups of n=20) provided 60% survival, and was determined to be of optimal efficacy under the experimental conditions tested, since two doses of 2.5 mg/kg gave only 30% survival (p<0.005 was calculated, using log rank test, between the treated and control groups).

A similar effect was observed for a dose of 5 mg/kg, given to groups of n=10 animals, as a single dose, where 45% survival was detected, while two doses provided only 30% protection. Addition of more than two doses (3 or 4 doses), did not improve the outcome of 2 doses, and was less efficacious than one dose.

Interval Between Doses

Figure 8A:
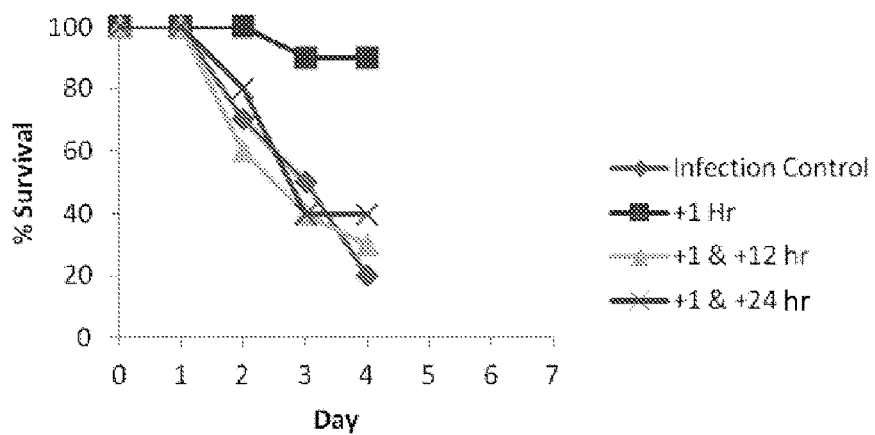
FIG. 8A is a Kaplan-Meier survival plot of BALB/c mice, demonstrating the efficacy of single vs. two doses of D-Ala-p2TA, at different interval between doses (12 hours and 24 hours).
Figure 8B:
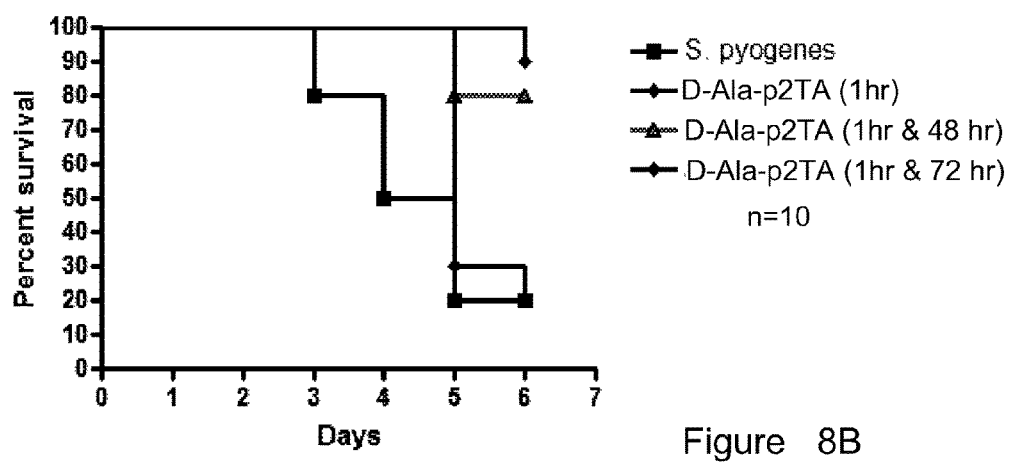
FIG. 8B is a Kaplan-Meier survival plot of BALB/c mice, demonstrating the efficacy of single vs. two doses of D-Ala-p2TA, at different, higher, interval between doses up to 48 hours and 72 hours.

The effect of two doses as compared to a single dose (first dose given at 1 hour post infection) was also measured as a function of the time interval between the doses, using various dose strengths, of either 2.5, or 5 or 10 mg/kg. As shown in FIG. 8A, one dose was superior as compared to two doses, whether these doses were given at a 12 or 24 hours interval, or as shown in FIG. 8B, where one dose was superior as compared to two doses, also when these doses were given at a 48 or 72 hours interval. These data were consisted across all doses tested (2.5, 5 and 10 mg/kg). Of all doses tested, the 2.5 mg/kg had the highest treatment benefit, providing 90% survival when given as a single dose (p=0.0043 vs. control and 0.0057 vs. 2 doses).

Further support for the superiority of a single dose of 2.5 mg/kg may be found from calculating the median survival time, which was found to be 3 days for all the above treated groups, as well as the control non-treated group, except for the group which received a single dose of 2.5 mg/kg (which had a median survival time of >8 days). These results are summarized in Table 1 below.

TABLE 1

Median survival time of mice treated with different regimens/doses of the peptide D-Ala-p2TA

| Treatment regimen | Dose | Median Survival |
|---|---|---|
| Infectious control | NA | 3 days |
| D-Ala-p2TA, single dose | 2.5 mg/kg | >8 days |
| D-Ala-p2TA, 2 doses (1 + 12 hours) | 2.5 mg/kg | 3 days |
| D-Ala-p2TA, 2 doses (1 + 24 hours) | 2.5 mg/kg | 3 days |
| D-Ala-p2TA, single dose | 5 mg/kg | 3 days |
| D-Ala-p2TA, 2 doses (1 + 12 hours) | 5 mg/kg | 3 days |
| D-Ala-p2TA, 2 doses (1 + 24 hours) | 5 mg/kg | 3 days |

Figure 9:
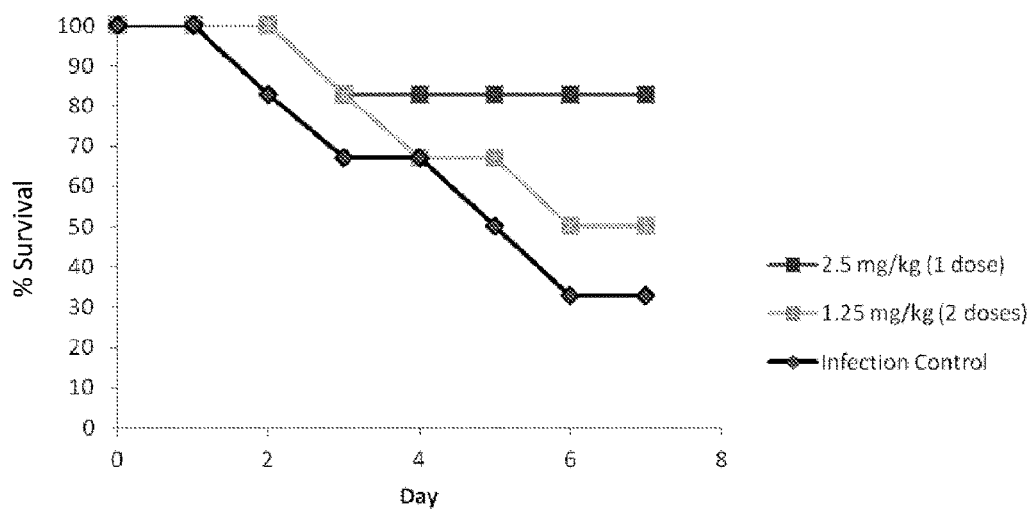
FIG. 9 is a Kaplan-Meier survival plot of BALB/c mice, demonstrating the effect of dose fractionation of D-Ala-p2TA on survival of mice infected with S. pyogenes.

Dose Fractionation:

Administration of the efficacious total dose of 2.5 mg of the peptide D-Ala-p2TA per kg body weight was examined in *S. pyogenes* infection (n=10) when given as a single dose, and when fractionated into 2 doses of 1.25 mg/kg each, that were given at an interval of 5 minutes between the doses. As can be seen in FIG. 9, administration of a single dose provided 85% survival, and provided higher efficacy as compared to a fractionated cumulative identical dose that gave only 50% survival. Similar results were obtained when the interval between the fractionated doses was longer (4-12 hours). These data may suggest that initial exposure of mice to the effective dose may be important to convey protection and that dividing the effective dose into smaller fractions is reducing the efficacy.

2.6 Effect of the D-Ala-p2TA Peptide on Cytokine Production

The effects of the peptide D-Ala-p2TA under conditions of Gram-positive infection by *S. pyogenes*, on cytokine production were explored.

Balb/c mice (10 treated and 10 controls) were infected with *S. pyogenes*, and the peptide D-Ala-p2TA (at 5 mg/kg) was administered at 1 hour post-infection. Infected non-treated mice were injected with PBS and served as control. At 12 hours after the infection, mice were euthanized, and blood was collected for determination of cytokines and chemokines in plasma, using a multiplex immunoassay.

Overall, nine cytokines and chemokines were evaluated, and included Th1 cytokines (IFN-γ, TNF-α, IL-1β, IL-17A) Th2 cytokines (IL-10) and inflammatory cytokines/chemokines (IL-6, KC (Mouse IL-8), RANTES, MCP-1). The results are presented in FIG. 10A and in FIG. 10B. Reduction in cytokine levels was observed for all tested cytokines/chemokines, namely IFN-γ, IL-17A, TNF-α and IL-1β, as shown in FIG. 10A-1, FIG. 10A-2, FIG. 10A-3 and FIG. 10A-4, respectively and IL-8, IL-6, RANTES and MCP-1, as shown in FIG. 10B-1, FIG. 10B-2, FIG. 10B-3 and FIG. 10B-4, respectively, indicating that already at an early time point post-infection, the level of multiple cytokines is decreased, which is consistent with the in-vitro results obtained and with the expected mechanism of action. The effect of decline in multiple cytokines is synergistic, and therefore the impact of each cytokine level will be amplified in terms of synergy, which is reduction of the inflammatory response to a greater extent.

Figures 1, 10A:
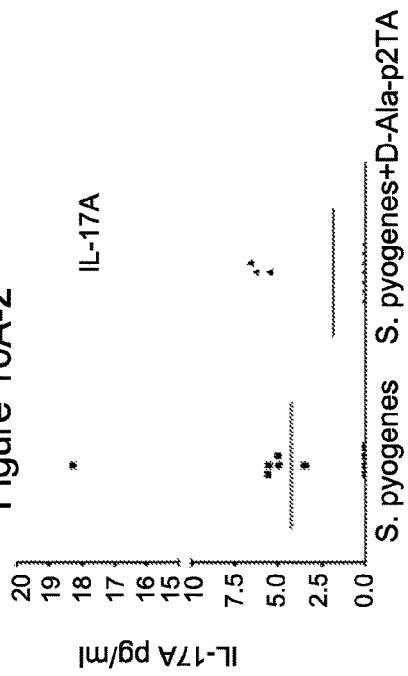
FIG. 10A includes graphs demonstrating the effect on plasma Th1 cytokines, at 12 hours post infection.
Figures 2, 10A:
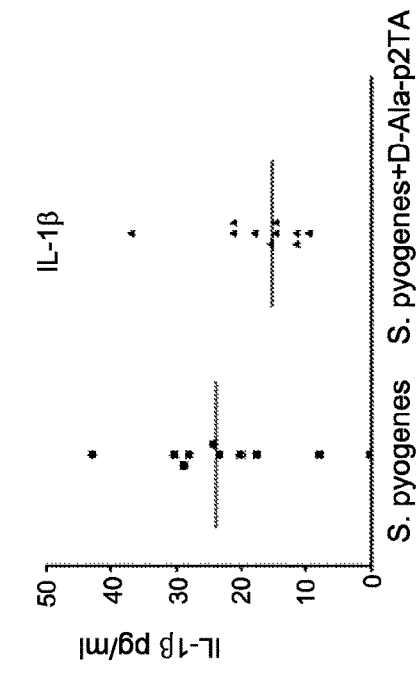
Figures 3, 10A:
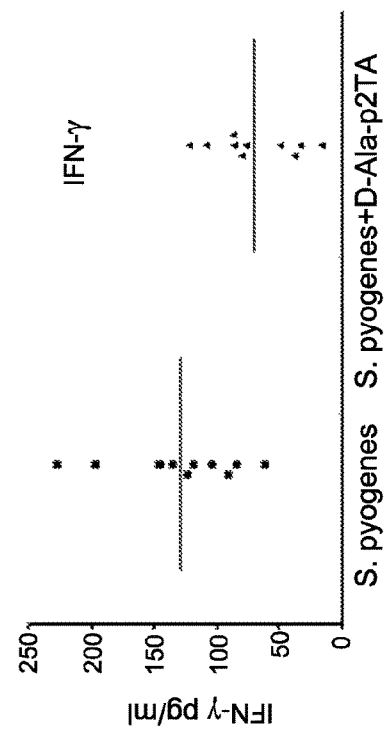
Figures 4, 10A:
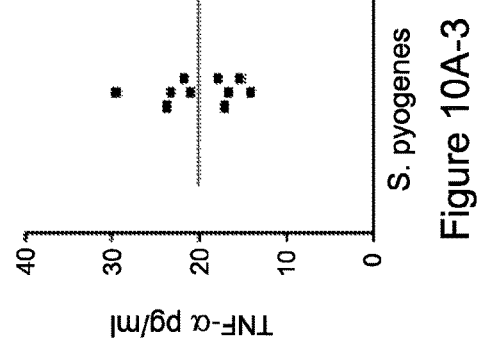
Figures 1, 10B:
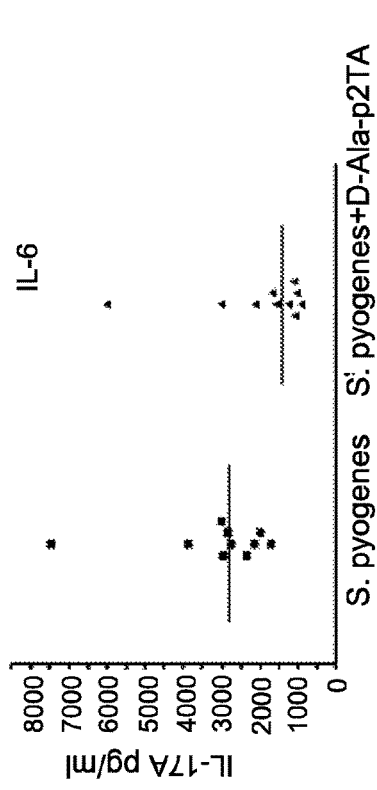
FIG. 10B includes graphs demonstrating the effect on plasma inflammatory cytokines, at 12 hours post infection.
Figures 2, 10B:
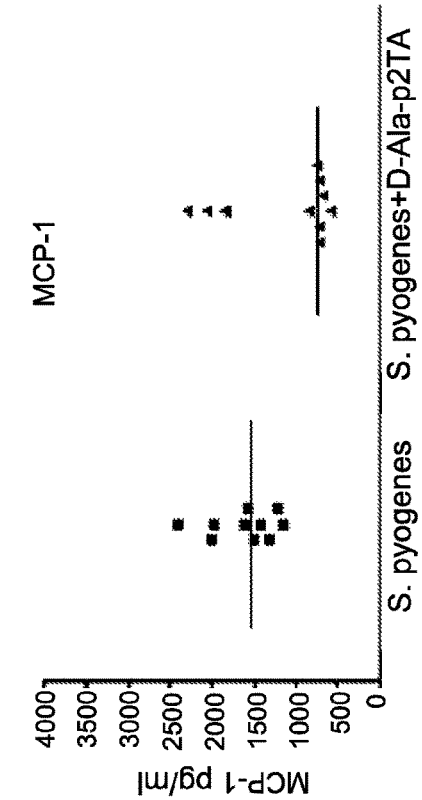
Figures 3, 10B:
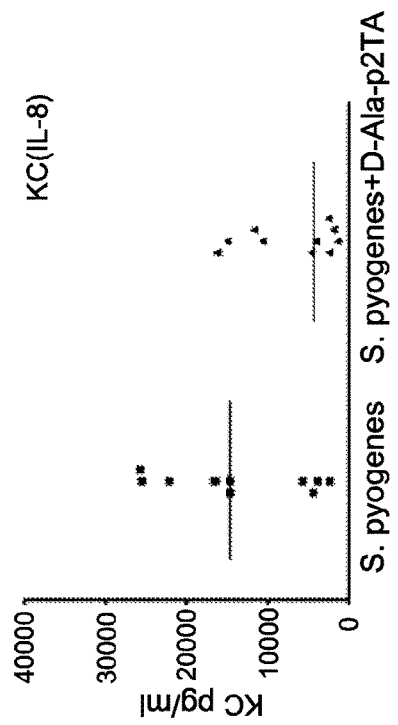
Figures 4, 10B:
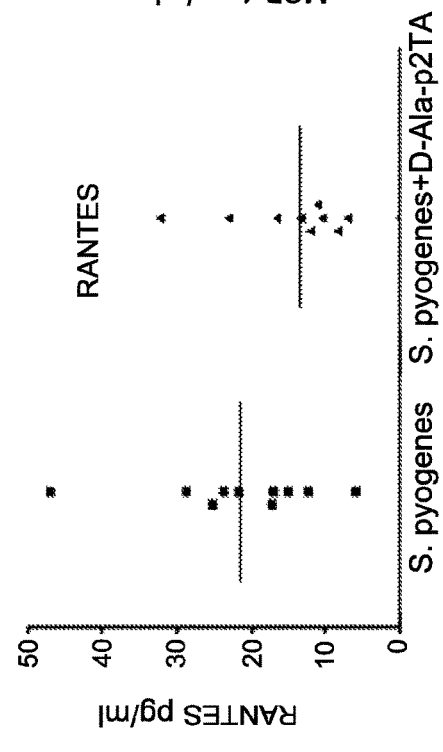
Figure 10C:
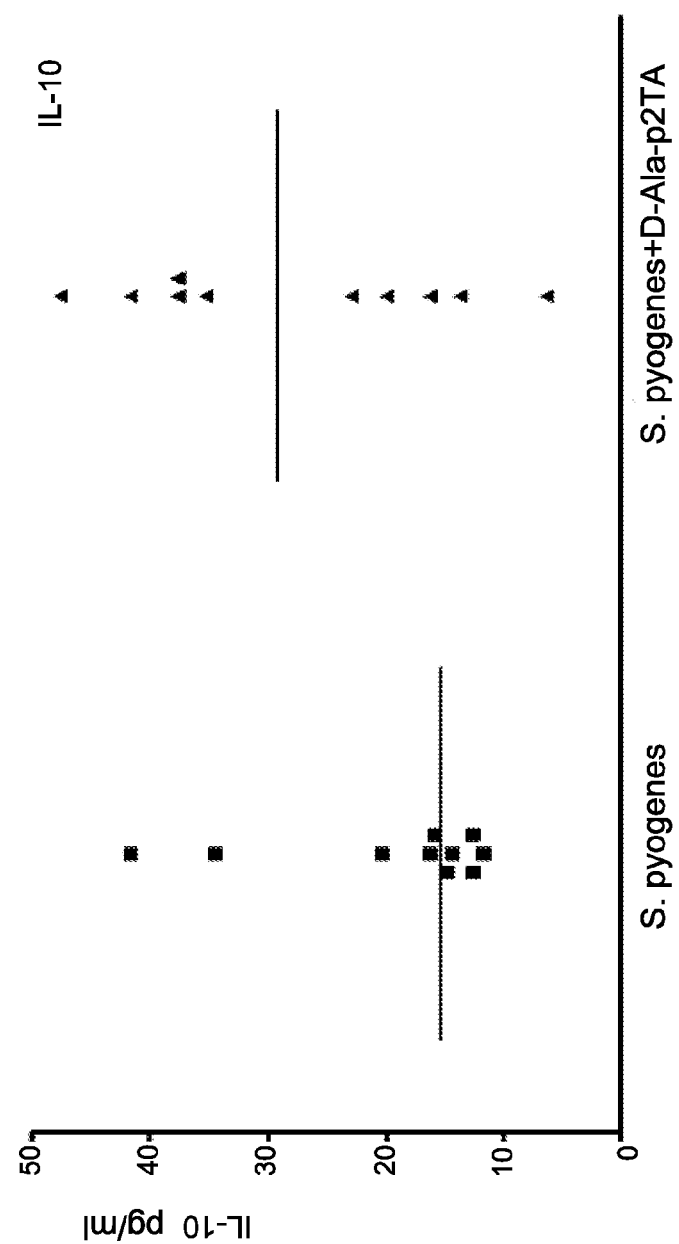
FIG. 10C is a graph demonstrating the effect on a plasma Th2 cytokine, IL-10, at 24 hours post infection.

Interestingly, the level of the Th2 cytokine IL-10 showed an increase, reaching a zenith (peak) at 24 hours post infection (shown in FIG. 10C). The augmented levels of IL-10 at a later time point of 24 hours suggest that the initial reduction in Th1 pro-inflammatory cytokines levels is subsequently followed by an increase in the anti-inflammatory Th2 cytokines, which may contribute to a better management of the bacterial infection.

Attenuation of Pro-Inflammatory Cytokine Production in Infected Mice is Extended by the Peptide D-Ala-p2TA Upon "bridging" the MHC II molecules on APCs and TCRs on T cells, superantigens (SAgs) activate >20% of T cells with a massive release of pro-inflammatory cytokines and a subsequent lethal shock.

Serum samples harvested at 12, 24, 48 and 72 h post infection were tested for cytokines (IFN-γ, TNF-α, IL-1β, IL-6 IL-17, and IL-10) and chemokines (KC, RANTES, MCP-1) in samples taken from mice infected with GAS either treated with the peptide D-Ala-p2TA or PBS (control) one hour post infection. Indeed, compared to untreated controls, in mice treated with D-Ala-p2TAa significant reduction in level of several pro-inflammatory cytokines was observed as early as 12 h post D-Ala-p2TA administration, which is consistent with the in-vitro data.

TABLE 2

Cytokines and chemokines levels at 48 and 72 hours in samples taken from mice infected with GAS treated with D-Ala-p2TA or PBS (control) one hour post infection

|  | *S. pyogenes* 48 hr (pg/ml) | D-Ala-p2TA peptide treatment 48 hr (pg/ml) | p Value |
|---|---|---|---|
| IL6 | 3707 +/− 1380 | 997 +/− 559 | 0.02* |
| IL1β | 31 +/− 3 | 21 +/− 5 | 0.13 |
| TNFα | 18 +/− 2 | 14 +/− 1 | 0.57 |
| IFNγ | 10 +/− 1 | 5 +/− 2 | 0.5 |
| IL17 | 0.8 +/− 0 | 0.4 +/− 0 | 0.8 |
| IL10 | 48 +/− 4 | 29 +/− 14 | 0.04* |
| KC | 4009 +/− 1936 | 2250 +/− 1481 | 0.75 |
| MCP1 | 278 +/− 27 | 140 +/− 21 | 0.025* |
| RANTES | 19 +/− 4 | 12 +/− 3 | 0.1 |

|  | *S. pyogenes* 72 hr (pg/ml) | D-Ala-p2TA peptide treatment 72 hr (pg/mi) | p Value |
|---|---|---|---|
| IL6 | 6895 +/− 468 | 889 +/− 681 | 0.009** |
| IL1β | 26 +/− 1 | 11 +/− 4 | 0.17 |
| TNFα | 27 +/− 5 | 13 +/− 2 | 0.04* |
| IFNγ | 9 +/− 1 | 3 +/− 2 | 0.35 |
| IL17 | 0 +/− 0 | 0 +/− 0 | 0.67 |
| IL10 | 113 +/− 31 | 54 +/− 13 | 0.01** |
| KC | 4103 +/− 648 | 2373 +/− 1193 | 0.88 |
| MCP1 | 265 +/− 6 | 192 +/− 34 | 0.1 |
| RANTES | 25 +/− 6 | 8 +/− 3 | 0.11 |

Compared to the untreated mice, levels of IFN-γ, IL1-β and IL-6 in the peptide-treated mice were attenuated significantly at all four time points. Cytokines/chemokine levels at 48 and 72 hours are shown in Table 2, above.

Concomitant survival analysis performed in this set of mice showed that only 5 out of 10 non-treated mice survived 48 hr post infection, and 2 out of 10 untreated mice survived for 72 hr, whereas 10 out 10 D-Ala-p2TA Peptide-treated mice survived the bacterial challenge for 72 hr.

Figures 1, 11B:
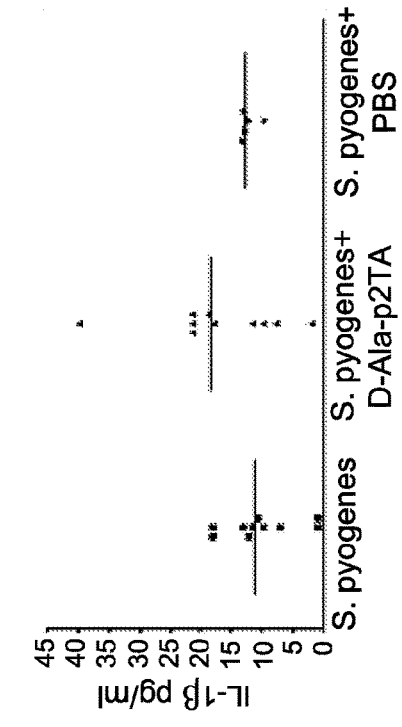
FIG. 11B includes graphs representing serum level of IL-1β in mice infected intramuscularly with S. pyogenes in the absence of any further treatment or where the mice where treated with the peptide D-Ala-p2TA at 12 (FIG. 11B-1), 24 (FIG. 11B-2), 48 (FIG. 11B-3) and 72 (FIG. 11B-4) hours post-infection.
Figures 2, 11B:
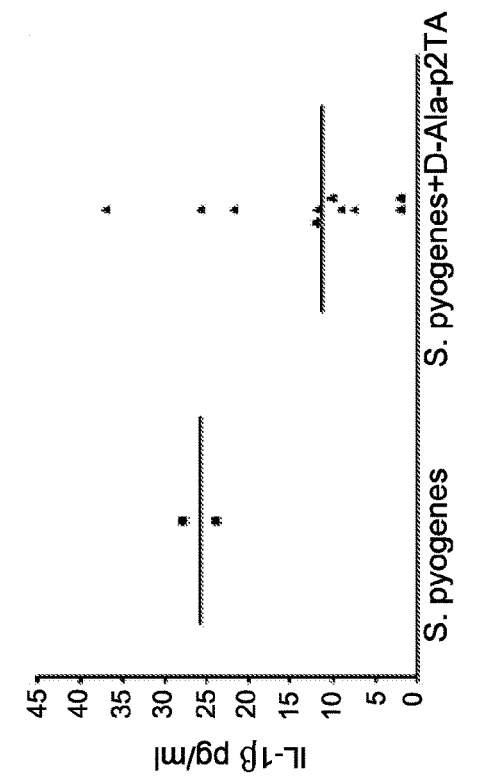
Figures 3, 11B:
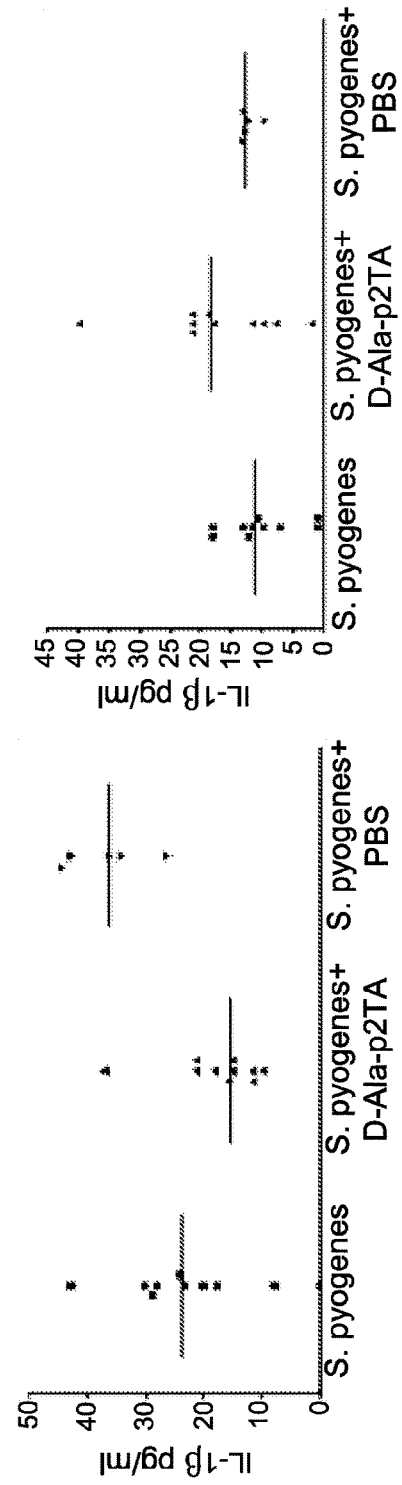
Figures 4, 11B:
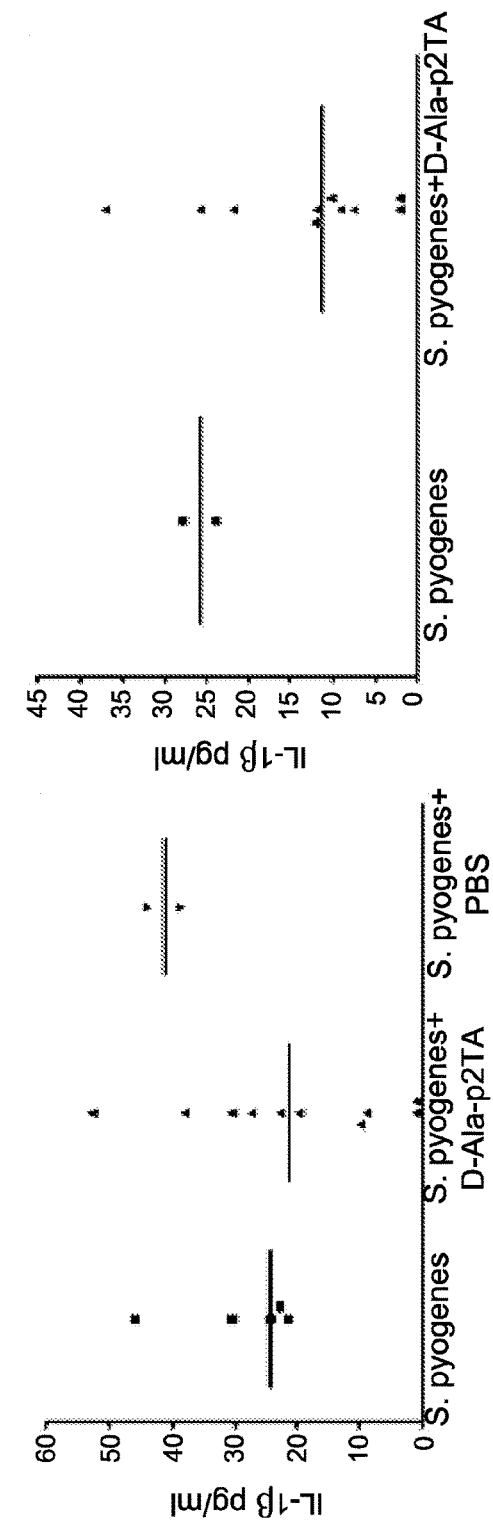
Figures 1, 11C:
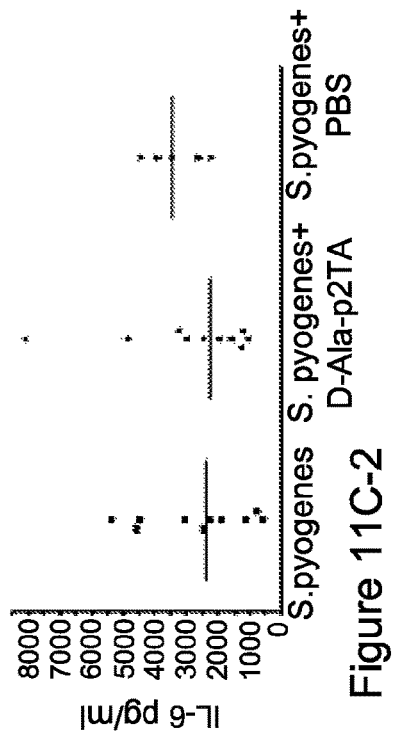
FIG. 11C includes graphs representing serum level of IL-6 in mice infected intramuscularly with S. pyogenes in the absence of any further treatment or where the mice where treated with the peptide D-Ala-p2TA at 12 (FIG. 11C-1), 24 (FIG. 11C-2), 48 (FIG. 11C-3) and 72 (FIG. 11C-4) hours post-infection.
Figures 2, 11C:
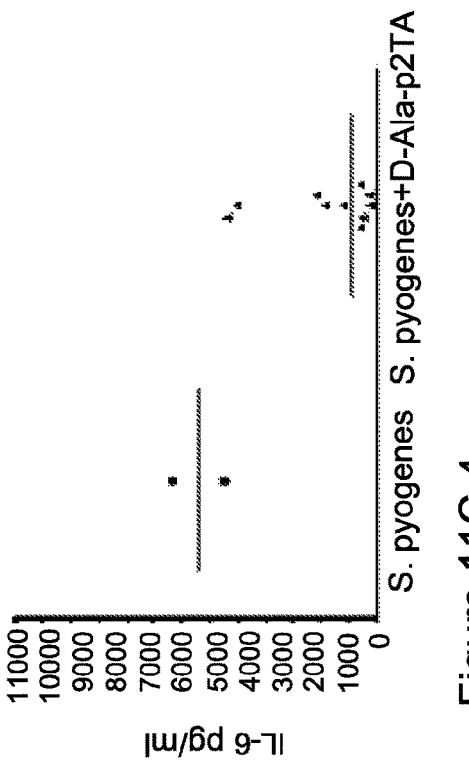
Figures 3, 11C:
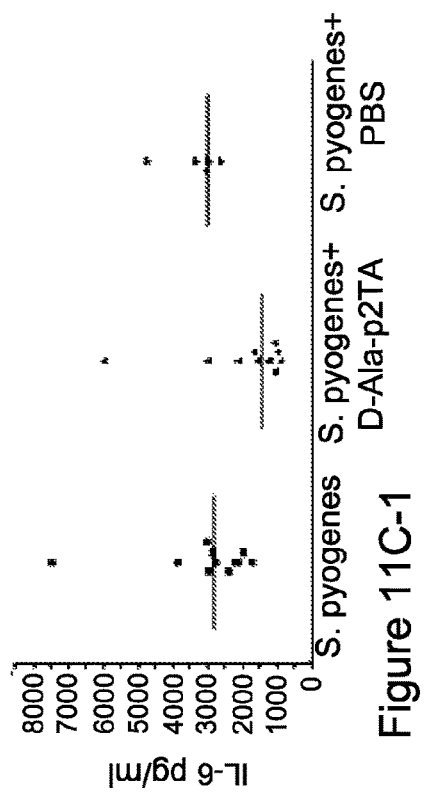
Figures 4, 11C:
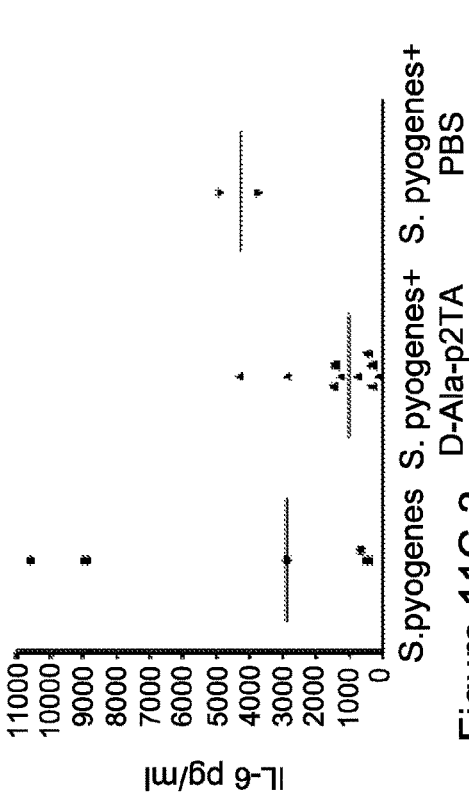
Figures 1, 11D:
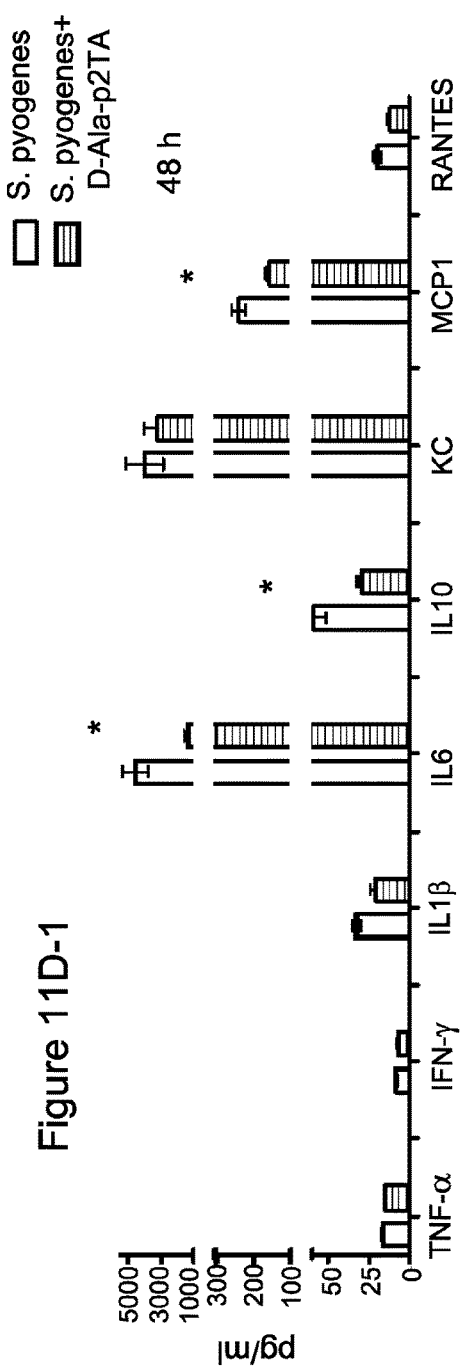
FIG. 11D includes graphs representing serum cytokine level averages in mice infected with S. pyogenes and treated with D-ala-p2TA.
Figures 2, 11D:
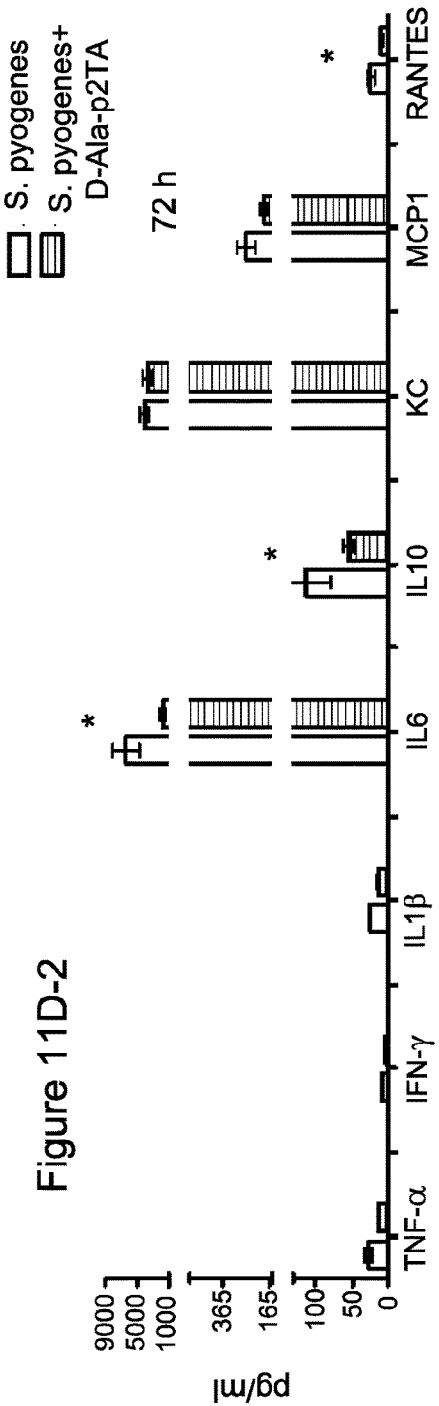

The median for each cytokine at all time points are presented in FIGS. 11A-D, as follows: FIG. 11A-1 shows the results obtained for IFN-γ at 12 hours post infection and the results obtained for IFN-γ at 24, 48 and 72 hours are shown in FIG. 11A-2, FIG. 11A-3 and FIG. 11A-4, respectively. FIG. 11B-1 shows the results obtained for IL-1β at 12 hours post infection and the results obtained for IL-1β at 24, 48 and 72 hours are shown in FIG. 11B-2, FIG. 11B-3 and FIG. 11B-4, respectively. Similarly, FIG. 11C-1 shows the results obtained for IL-6 at 12 hours post infection and the results obtained for IL-6 at 24, 48 and 72 hours are shown in FIG. 11C-2, FIG. 11C-3 and FIG. 11C-4, respectively. FIG. 11D shows a graphical representation of the results presented in table 2 for eight cytokines, i.e. TNF-α, IFN-γ, IL-1β, IL-6, IL-10, KC (mouse IL-8), MCP-1 and RANTES at 48 h (FIG. 11D-1) and 72 h (FIG. 11D-2) post infection.

2.7. Effect of the Peptide D-Ala-p2TA on Bacterial Load after Infection with *S. pyogenes*

After infection with bacteria, the bacteria spread from the local infection site to key organs such as spleen, liver and kidney, where they continue to secrete toxic components, thus contributing to organ damage. The mice infected with *S. pyogenes* were not treated with antibiotics, yet they survived the infection. It was therefore investigated whether the peptide D-Ala-p2TA, which has no anti-bacterial properties, may indirectly affect the bacterial load in the infections site or in key organs.

Groups of 5 Balb/c mice were infected with *S. pyogenes* and treated with either the peptide D-Ala-p2TA or PBS. Non-treated mice served as infection control. Mice were euthanized 24 and 48 hours post infection, and tissue samples from the infected thighs and the spleen were collected and homogenized. After serial dilution, the homogenate was plated to determine the level of CFU/mg of tissue for each group. Results are presented in FIG. 12, and indicate that in the absence of antibiotics and following the treatment with the peptide D-Ala-p2TA, a reduction in the level of bacteria disseminated both at the infection site and at a remote organ is evident already at 24 hours (see FIG. 12A, muscle and FIG. 12C, spleen), and is sustained until 48 hours (see FIG. 12B, muscle and FIG. 12D, spleen). Mice that have a reduced bacterial load may be able to develop antibodies against the bacterial toxin, thus neutralizing their harmful toxicity.

Figure 13A:
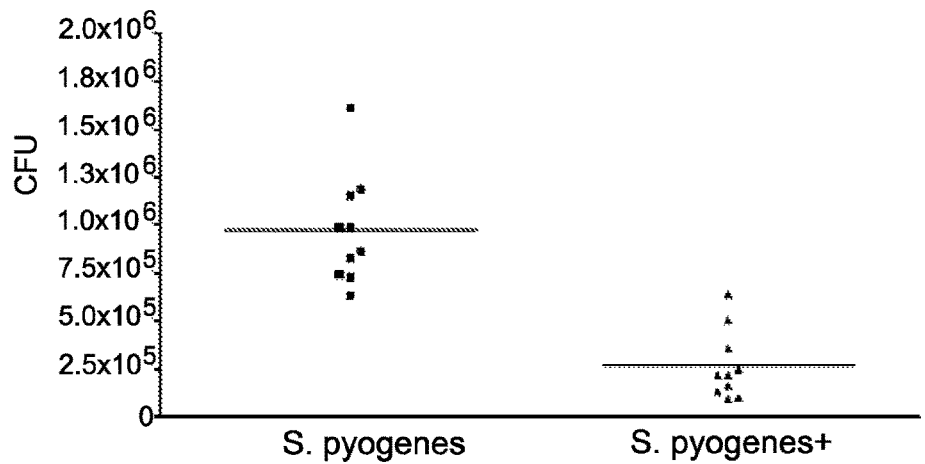
FIG. 13A is a graph representing bacterial burden of S. pyogenes at 72 hours in muscle of D-Ala-p2TA treated vs untreated mice.

The Peptide D-Ala-p2TA Attenuates the Bacterial Burden Up to 72 Hours Post Infection Remarkably, a significant difference in bacterial count was observed up to 72 hours post infection between the untreated and D-Ala-p2TA treated mice in muscle tissue (FIG. 13A).

Figure 13B:
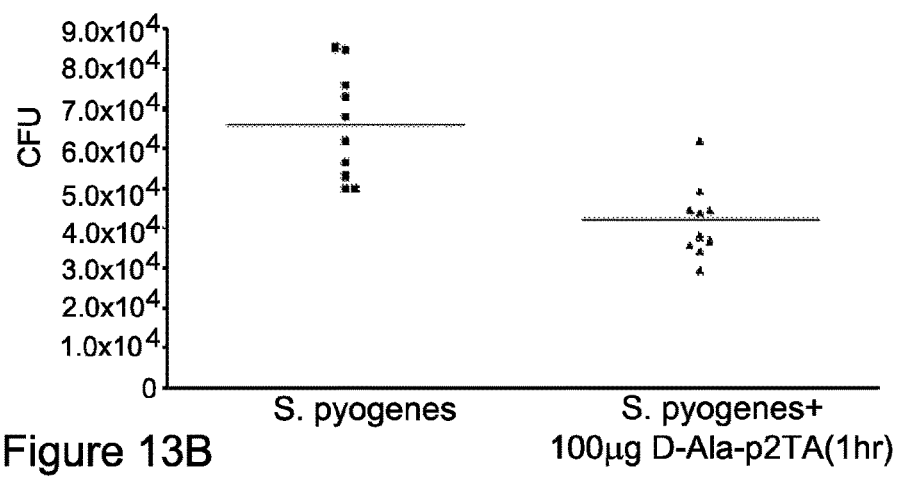
FIG. 13B is a graph representing bacterial burden of S. pyogenes at 72 hours in liver of D-Ala-p2TA treated vs untreated mice.
Figure 13C:
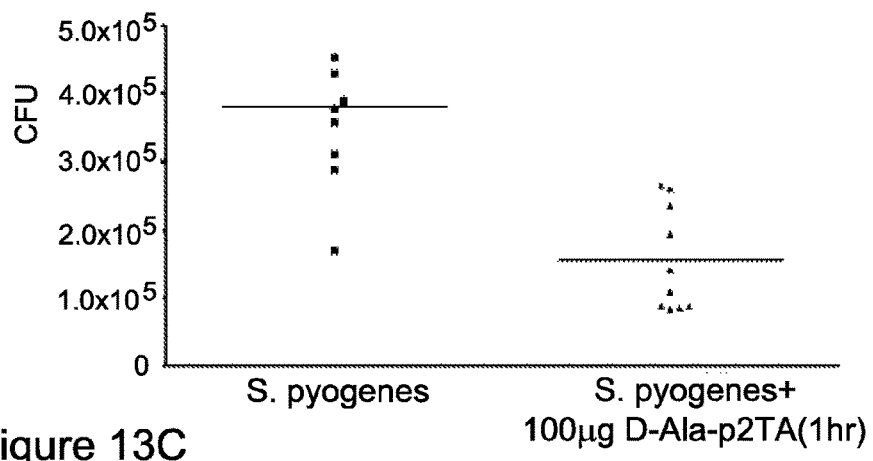
FIG. 13C is a graph representing bacterial burden of S. pyogenes at 72 hours in spleen of D-Ala-p2TA treated vs untreated mice.

At 3 days post infection, no massive dissemination of the pathogen into sites remote from the infection site, namely to the lungs, kidney, liver or systemic blood, was observed in infected animals. However, a low level of bacteria was detected in the spleen and liver, with a small difference between the treated and untreated groups (FIGS. 13B-C). These data suggest that during the course of infection of mice with GAS, the predominant effects leading to fatal outcome might result from bacterial virulence factors such as toxins and enzymes, as well as from the release of cytokines, acting remotely.

The Peptide Antagonist Effectively Attenuates Myositis in Muscle Tissue

Figure 14A:
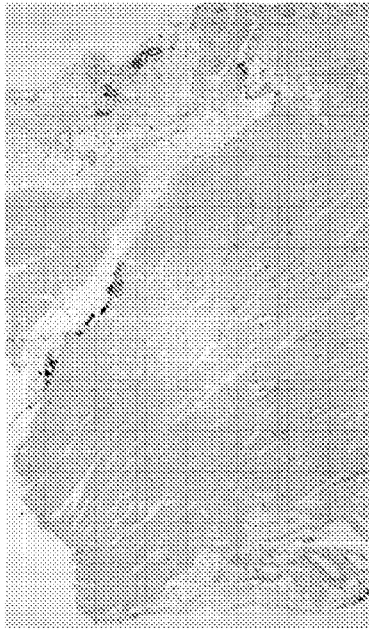
FIG. 14A and FIG. 14C are micrographs of mouse stained muscle sections post S. pyogenes infection treated with the peptide D-ala-p2TA
Figure 14B:
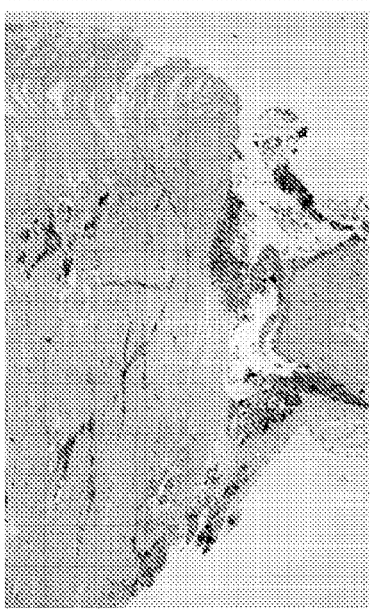
Figure 14C:
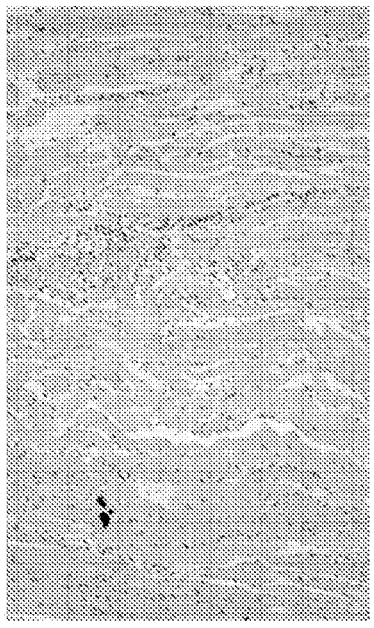
Figure 14D:
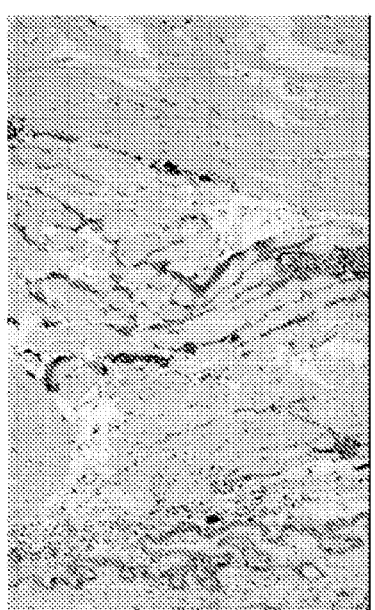
FIG. 14D), post S. pyogenes infection.

In untreated mice, the onset of necrotizing fasciitis was observed as early as 24 h post infection. In order to study tissue pathology, muscle sections were stained with H&E (Hematoxylin and Eosin) stain, a widely used stain in medical diagnosis. By 48 h post infection, muscle sections showed severe acute inflammatory infiltrate primarily in the fascia. Compared with the untreated controls, muscle sections from D-Ala-p2TA peptide-treated mice showed a milder infiltrate (FIG. 14A-B). In sections of muscle taken from untreated controls at 72 h, there was an apparent severe necrosis of muscle cells, composed primarily of neutrophils, whereas in D-Ala-p2TA-treated mice the necrosis was significantly milder (FIG. 14C-D).

The histology data presented above is consistent with the cytokine profile observed at these time points (as presented in Table 2, above) and with the reduced tissue damage (necrosis) presented in FIG. 5. The severe infiltration of inflammatory cells to the site of infection in untreated mice correlates with a significant increase in chemokine levels in infected untreated animals, and with the reduction in levels of chemokines (particularly in KC) following D-Ala-p2TA treatment.

In contrast to the pathological changes observed at the site of infection, no differences were observed in tissue pathology between the treated and untreated groups in remote organs such as liver and kidney. This is further supported by no observable differences or abnormalities in the kidney and liver functions between the two groups when the serum from these mice were tested for creatinine, ALT, AST, alkaline $PO_4$ and bilirubin (as shown in Table 3, below).

TABLE 3

Changes in lab biochemistry parameters in mice that were either subjected to infection or infected and treated with D-Ala-p2TA. The values indicated are for each individual mouse.

| | *S. pyogenes* infected mice | | | | | D-Ala-p2TA peptide treated mice post infection | | | | |
|---|---|---|---|---|---|---|---|---|---|---|
| | 1 | 2 | 3 | 4 | 5 | 1 | 2 | 3 | 4 | 5 |
| Creatnine (mg/dL) | 0.1 | 0.2 | 0.1 | 0.1 | 0.1 | 0.1 | 0.1 | 0.1 | 0.1 | 0.2 |
| AST (U/L) | 88 | 138 | 93 | 129 | 142 | 60 | 127 | 185 | 144 | 290 |
| ALT(U/L) | 17 | 22 | 18 | 19 | 27 | 17 | 22 | 31 | 17 | 32 |
| Alkaline P04 (U/L) | 28 | 30 | 30 | 28 | 44 | 34 | 33 | 44 | 28 | 26 |
| Bilirubin (mg/dL) | 0.1 | 0.2 | 0.1 | 0.1 | 0.1 | 0.1 | 0.1 | 0.1 | 0.1 | 0.2 |

The Peptide D-Ala-p2TA Attenuates Toxemia in Mice

We next examined whether mice treated with the peptide D-Ala-p2TA and challenged with group A *S. pyogenes* are able to produce antibodies against the streptococcal pyrogenic exotoxins A or C or streptococcal virulence factor B. Antibody titers were evaluated 5 days post infection (a time at which untreated mice were typically moribund), and 14 days post infection.

Figure 15A:
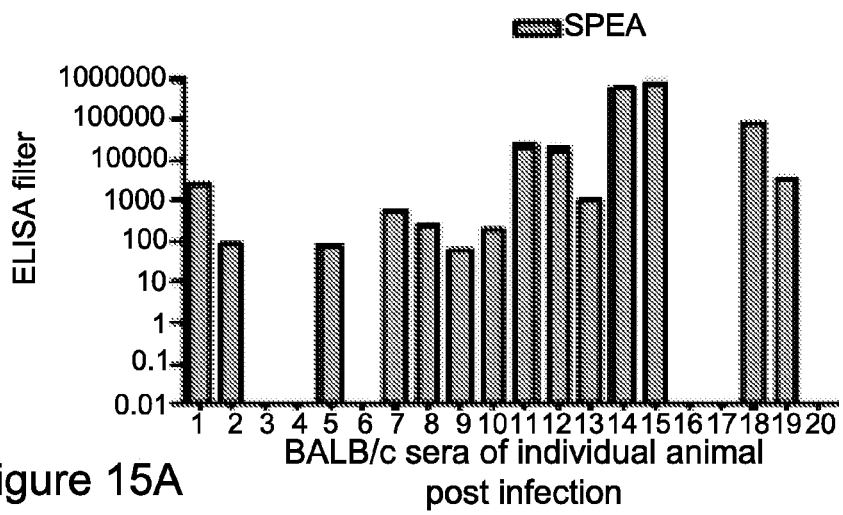
FIG. 15A is a graph demonstrating serum antibody titers against SPEA 5 days post infection.
Figure 15B:
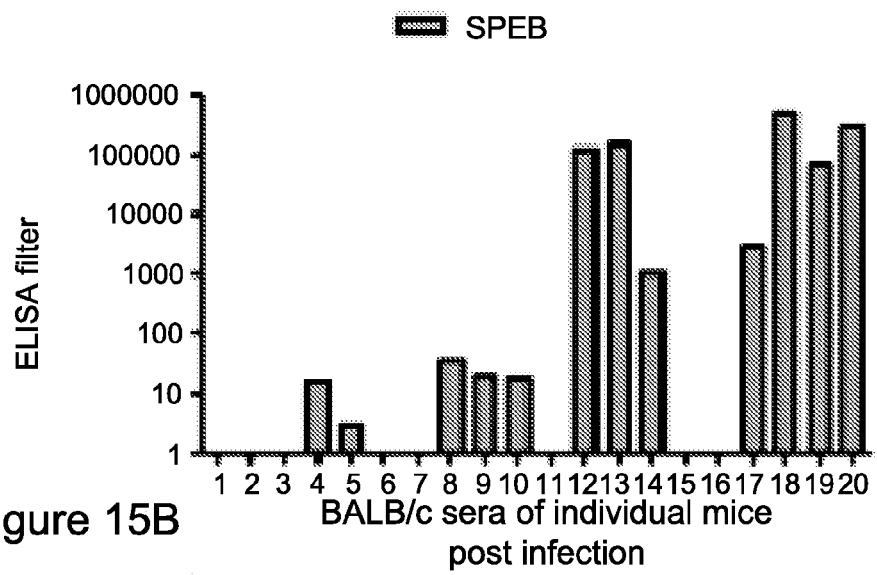
FIG. 15B is a graph demonstrating serum antibody titers against SPEB 5 days post infection.
Figure 15C:
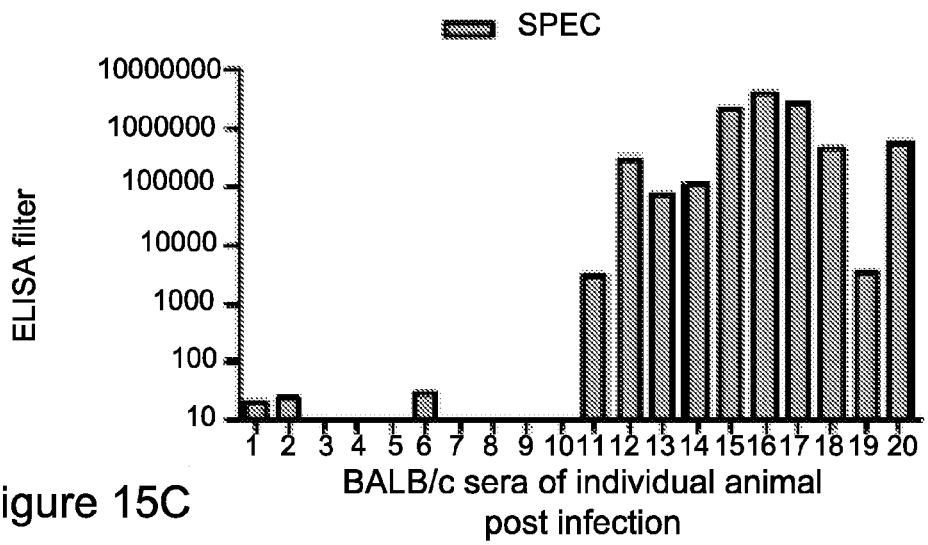
FIG. 15C is a graph demonstrating serum antibody titers against SPEC 5 days post infection.
Figure 15D:
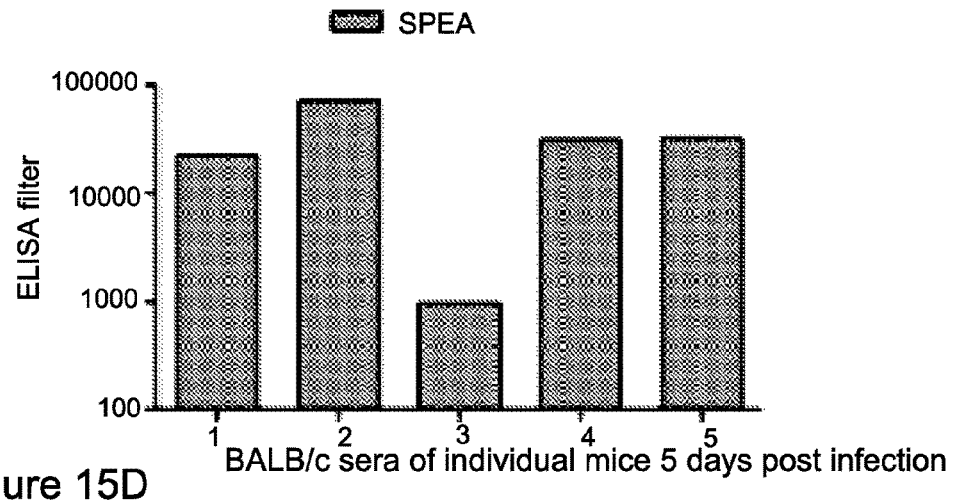
FIG. 15D is a graph demonstrating serum antibody titers against SPEA 14 days post infection.
Figure 15E:
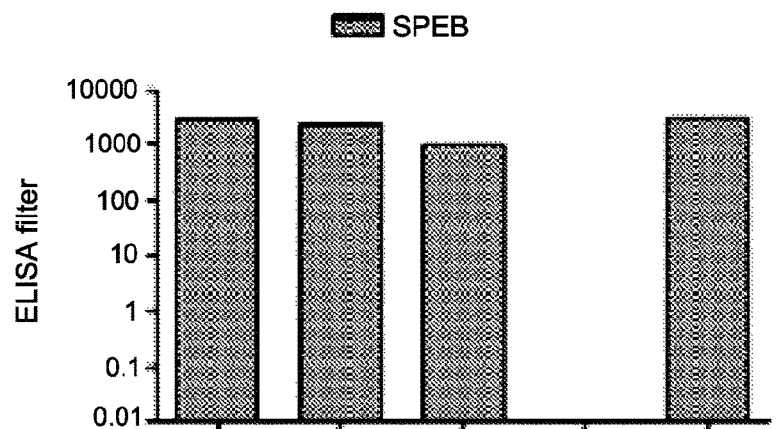
FIG. 15E is a graph demonstrating serum antibody titers against SPEB 14 days post infection.
Figure 15F:
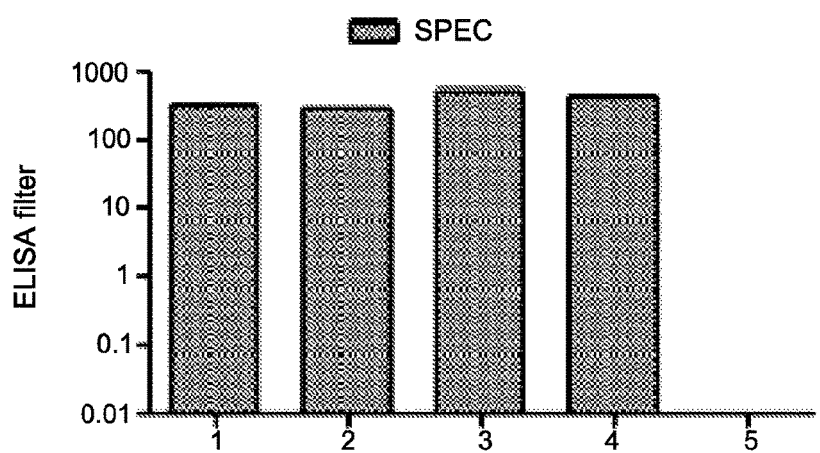
FIG. 15F is a graph demonstrating serum antibody titers against SPEC 14 days post infection.

As demonstrated in FIG. 15, titers against all three exotoxins were observed at the early time point of 5 days (FIGS. 15D, E and F). At two weeks post infection, most mice (17/20) still demonstrated antibody titers against at least one or two of the streptococcal superantigen/virulence factor molecules examined (FIGS. 15A, B and C), and the levels were higher as compared to titers at day 5.

Only three of the surviving mice did not develop antibodies against any of SPEA, SPEB and SPEC (FIG. 15A-C). It is possible that these mice either did not generate antibodies against GAS toxins, or that they developed antitoxin titers against other streptococcal toxins, such as streptococcal mitogenic exotoxin Z or streptococcal pyrogenic exotoxin J that were not assayed in this experiment. Cumulatively, these data suggest that the peptide D-Ala-p2TA protects mice against GAS challenge by attenuating toxemia rather than bacteremia.

Figure 16:
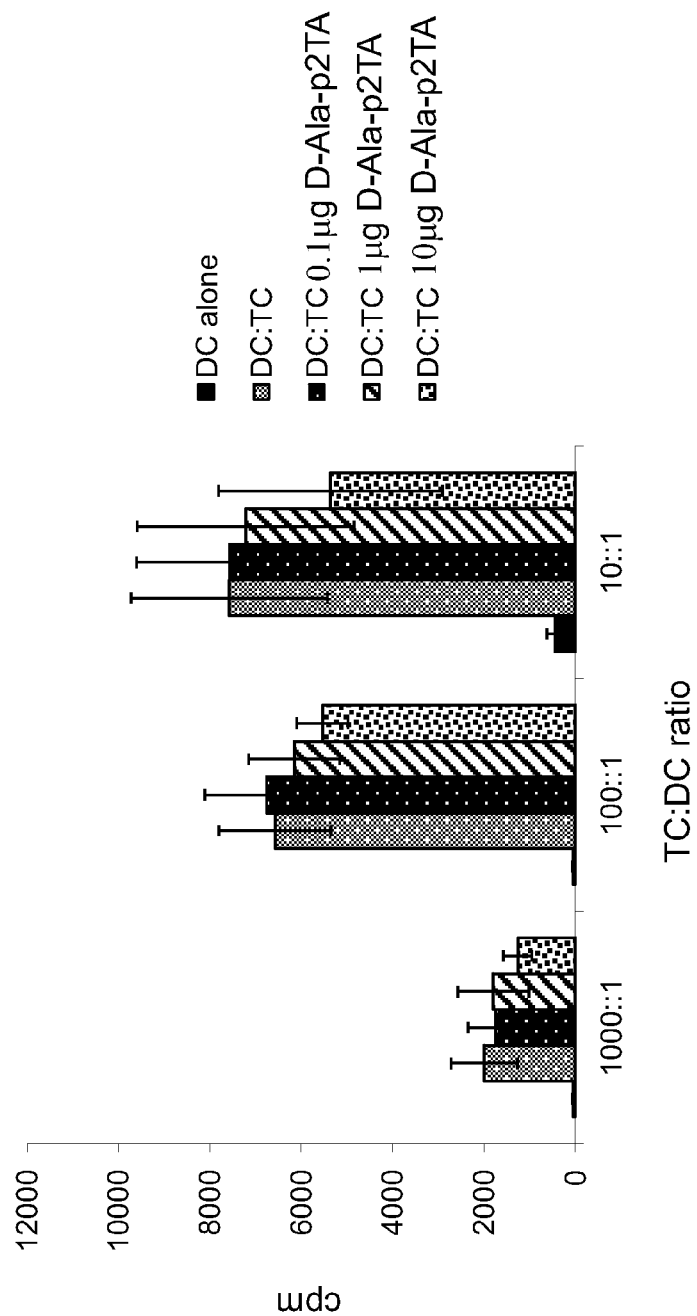
FIG. 16 is a graphical representation of a mixed lymphocyte reaction. Dendritic cells (DCs) from 3 different individuals were cultured with allogeneic peripheral blood mononuclear cells (PBMC) from 3 additional donors with increasing doses of D-Ala-p2TA for 3 days.

The Peptide D-Ala-p2TA does not Impede Induction of Antigen Presenting Cell (APC) Mediated Co-Stimulation of T-Cell Proliferation Since D-Ala-p2TA administered post-infection effectively promoted survival of mice following both superantigen and Strep. pyogenes challenge and since these challenges evoke a cytokine response (as shown in table 2, above), the potential effect of the peptide on cell proliferation was also tested. To this end, a mixed lymphocyte reaction (MLR) model was utilized, and the ability of Antigen Presenting Cells (APCs) to induce T-cell proliferation through co-stimulation of CD-28/TCR in the presence and absence of D-Ala-p2TA was measured. This model does not require an infective agent to stimulate T-cells and thus it was shown that using varying doses of the peptide D-Ala-p2TA, no inhibitory effect of the peptide (blocking the mixed lymphocyte reaction) was observed (FIG. 16).

Example 3

Model of Lung Infection

A lung infection model was established in BALB/c mice that were infected with the Gram-positive bacteria *Streptococcus pneumoniae* (at $10^7$ CFU/mice), under conditions that resulted in 100% mortality within 3-5 days. Treatment with the peptide D-Ala-p2TA was adjunct to antibiotic treatment, and was given at a delayed time point, when the infection was already established.

3.1 Protection from Lethal Lung Infection

Figure 17:
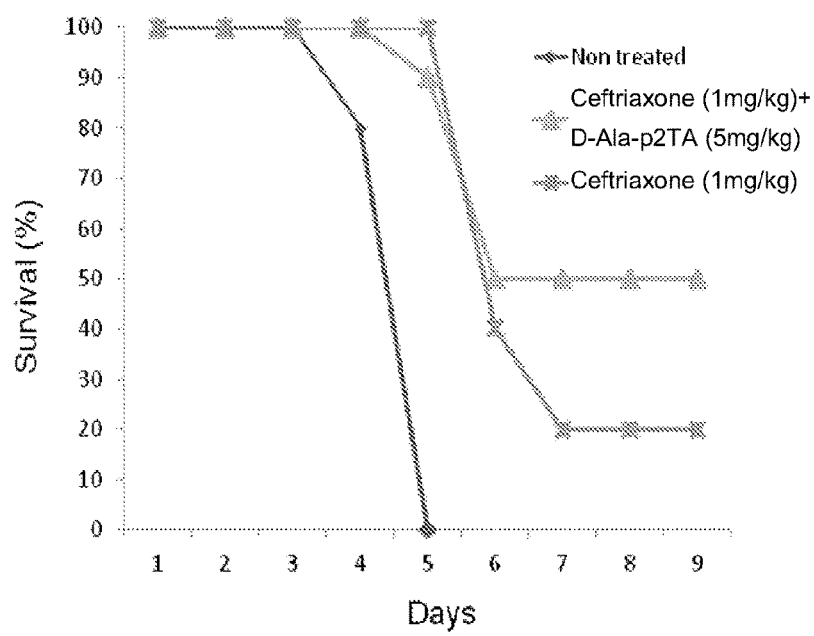
FIG. 17 is a survival graph demonstrating the effect of combined D-Ala-p2TA treatment and antibiotics following infection with *S. pneumoniae*, where treatment is administered at 24 hours post infection.

Mice infected with *S. pneumoniae* (using 10 animals per treatment group) that did not receive treatment, exhibited a death process, starting at 3 days post infection and progressing very quickly, such that after 2 more days (at day 5) all animals died. When the animals are treated with ceftriaxone alone, administered intraperitoneal (i.p.) at a suboptimal dose of $LD_{25}$ (1 mg/kg), given at 24 hours after the infection, survival rates increased to 20%. However, when the peptide D-Ala-p2TA (at 5 mg/kg) was given in combination with the antibiotics, 24 hours post infection, substantial increase in survival, to 50%, was detected (see FIG. 17).

3.2 Protection from Lethal Lung Infection: Dose Response

Figure 18:
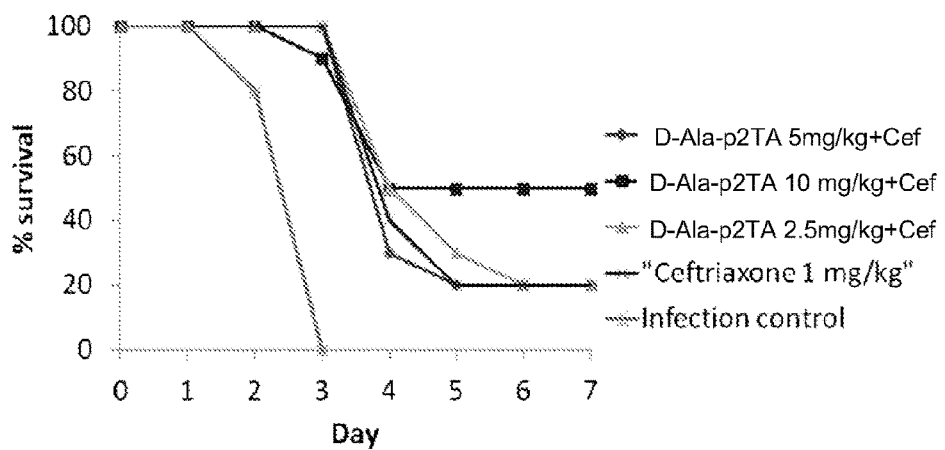
FIG. 18 is a survival graph demonstrating the efficacy of a single dose of D-Ala-p2TA (in combination with antibiotics) administered to mice, infected with *S. pneumoniae* at 24 hours post infection: A dose response.

The correlation between survival benefit and different doses of the peptide D-Ala-p2TA was investigated when the *S. pneumoniae* infected animals (n=10) received a combination of a fixed dose of antibiotics (ceftriaxone, at a suboptimal dose of 1 mg/kg, administered i.p.) and different doses of the peptide D-Ala-p2TA, given 2 minutes after antibiotic treatment at 24 hours post infection. Under these experimental conditions (see FIG. 18), non-treated mice died rapidly, starting at day 2, and by day 3, all animals were already dead. Antibiotic treatment alone did provide a minor change in survival, bringing it to 20%. Combined treatment with 5 mg/kg of the peptide D-Ala-p2TA conferred a substantial increase in survival (50%), and was found most efficacious, since doses of 2.5 or 10 mg/kg did not contribute to animal survival, beyond the effect of antibiotic alone.

Example 4

Models of Gramnegative Infections: Peritonitis *E. coli*

The ability of the peptide D-Ala-p2TA to increase overall survival in the presence of an invasive Gram-negative bacterial infection (*E. coli* peritonitis) was evaluated when administered with the antibiotic cefepime.

Acute bacterial peritonitis was induced by an i.p. challenge of BALB/c mice with the *E. coli* strain 018:K1, an invasive virulent isolate of *E. coli*. The challenge strain was grown to mid-log phase in TSB and then washed in normal saline, serially diluted, and administered to the animals. In preliminary experiments, a sub-inhibitory dose of the antibiotic cefepime (Elan) was established to be 5 mg/kg intra-muscular (i.m.), when given 4 hours after challenge (reflecting 25% of the usual effective dose).

In addition, preliminary experiments were performed to define the $LD_{50}$ of *E. coli* in BALB/c mice, following i.p. challenge, established to be $10^7$ colony forming units (CFU), and this $LD_{50}$ value was similar when repeated in the presence of sub-inhibitory concentrations of cefepime. The ability of the peptide D-Ala-p2TA (at 0.5-5.0 mg/kg, i.v.) to further protect animals following the induction of *E. coli* peritonitis in the presence of this suboptimal antimicrobial therapy was then tested, as follows.

Following the induction of *E. coli* peritonitis, peptide D-Ala-p2TA was administered to the mice i.v., at the time of infection, in combination with a suboptimal dose of cefepime. Survival of the animals was monitored over a period of 7 days. The survival rate of animals treated with a scrambled peptide (having the same amino acid composition, but at a different sequence) was comparable to the saline treated control.

Figure 19:
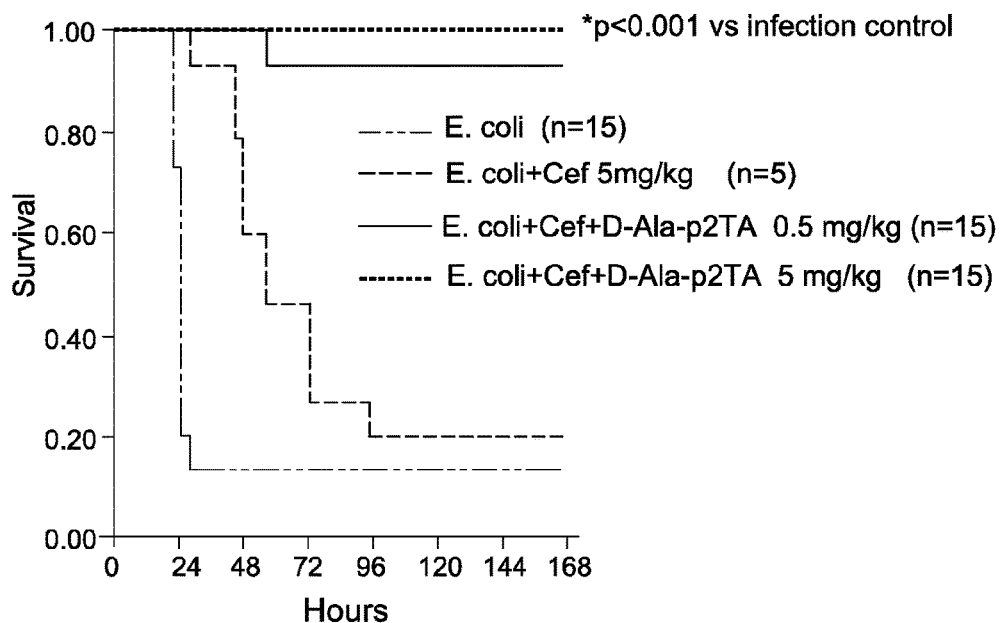
FIG. 19 is a graph demonstrating the protection of mice from bacterial peritonitis (induced by lethal infection with *E. coli*) by a combined treatment of antibiotic and D-Ala-p2TA (treatment with D-Ala-p2TA was initiated at the time of infection and antibiotics was given 4 hours post infection).

As shown in FIG. 19, in the absence of any treatment, the majority of the infected mice rapidly died (within 24 hrs), where only 15% of the mice survived. Treatment of mice with cefepime alone did not improve the final outcome, with 20% overall survival, however, the time up to death was slightly delayed. Mice infected with *E. coli* but treated with a combination of a suboptimal dose of cefepime and the peptide D-Ala-p2TA (at doses of 0.5 and 5 mg/kg), showed a statistically significant improvement in overall survival, 90 and 100%, respectively, when followed for 7 days. The survival rate of animals treated with a scrambled peptide (having same amino acid composition, but at a different sequence) was comparable to the saline treated control.

Figure 20:
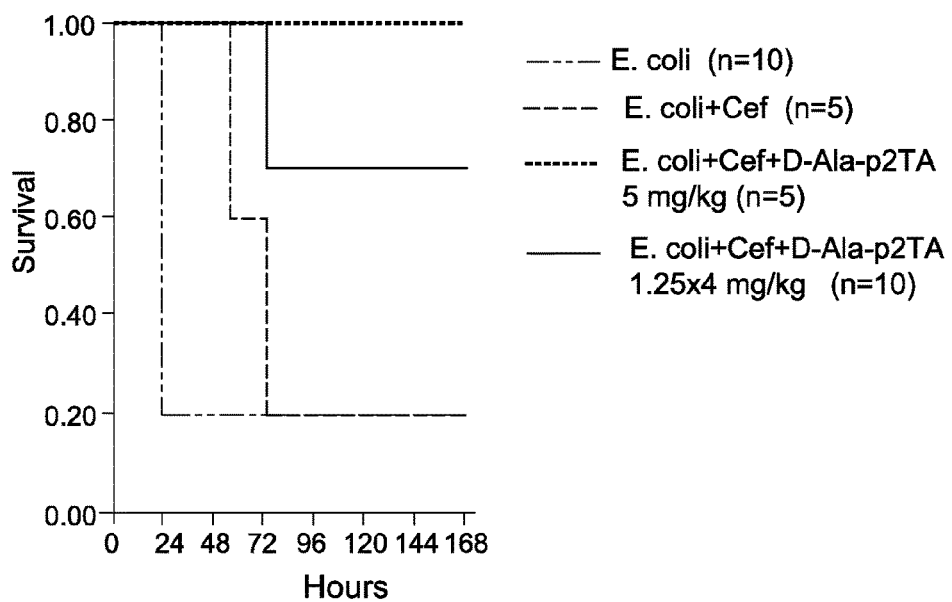
FIG. 20 is a graph demonstrating the effect of dose fractionation of D-Ala-p2TA (compared to a single full dose) on survival of mice infected with *E. coli*, where treatment with D-Ala-p2TA was initiated at the time of infection. Antibiotics were given at 4 hours post infection.

4.1. Effect of Dose Fractionation of the Peptide D-Ala-p2TA on Treatment Efficacy of Infected Animals Acute bacterial peritonitis was induced in BALB/c mice. The optimal dose of the peptide D-Ala-p2TA (given at the time of infection) found to portray 100% protection of mice from *E. coli* infection was 5 mg/kg. As compared to infection control, where animal survival declined rapidly within 24 hours to be 20%, addition of cefepime alone (at 4 hours post infection, at an $LD_{25}$), did not affect the fate of the animals, which still reached 20% survival, although at a slower rate. The treatment benefit of a single administration of the full effective dose of the peptide D-Ala-p2TA at 5 mg/kg was compared to dividing the dose into 4 equal portions of 1.25 mg/kg each, given at 12 hours intervals between doses, and indicated that dose fractionation is less efficacious, culminating in 70% survival, as shown in FIG. 20.

Example 5

Model of Polymicrobial Infection: Cecal Ligation and Puncture (CLP)

The murine cecal ligation and puncture (CLP) model is a clinically relevant model to investigate polymicrobial infections and follow the effects of therapeutic agents on intra-abdominal infections or sepsis. The animals were anesthetized (ketamine; 75 mg/kg and dexametonidine; 1 mg/kg)

with atipamezole hydrochloride 5 mg/kg as a reversal agent. The cecum was exteriorized through a 1.5 cm midline incision and ligated with a 5-0 nylon monofilament suture, at 90% of its length just distal to the ileocecal junction. The cecum was then punctured twice using a 23 gauge needle along the ante-mesenteric side of the cecum. Patency was assured by expressing a scant amount of laminal contents through puncture site. The organ was returned to the abdominal cavity, fascia and skin were closed, and topical lidocaine and bacitracin were applied at the surgical site. Each animal received 20 mg/kg intramuscular dose of moxifloxacin (representing suboptimal dose of $LD_{25}$) and 1 ml subcutaneous bolus of normal saline. The animals were allowed to be re-warmed until fully conscious and then returned to their cages.

The efficacy of the peptide D-Ala-p2TA when given intravenous (i.v.) was tested and animals were followed daily for a total of 7 days for overt signs of sepsis and survival. Moribund animals (defined as hypothermic <30° C. and unable to maintain normal body posture) were euthanized and scored as lethally-infected animals. At the end of day 7, survivors were euthanized. Animals were examined for quantitative microbiology of organ tissues (blood, peritoneum, liver, lung, and spleen).

Figure 21:
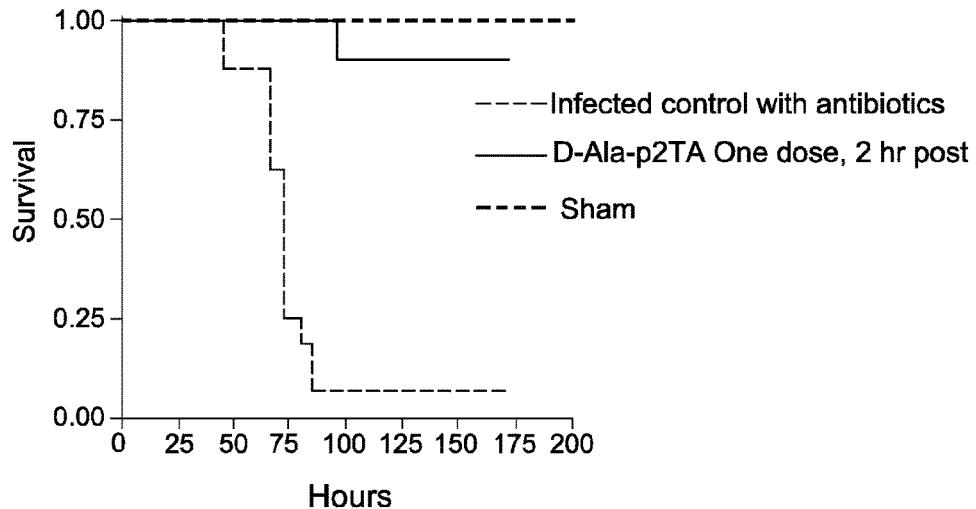
FIG. 21 is a Kaplan-Meier survival plot demonstrating the efficacy of one dose of peptide D-Ala-p2TA in reducing mortality after CLP. D-Ala-p2TA was given together with antibiotics, 2 hours after surgery.

5.1. Time Window of Administration of One Dose of the Peptide D-Ala-p2TA after CLP Since the peptide D-Ala-p2TA was shown to be most efficacious when administered as a single dose in cases of Gram-positive infections, its administration as a single dose was evaluated also in the polymicrobial infection model (FIG. 21). All animals received a suboptimal dose of moxifloxacin (at its $LD_{25}$) at the end of surgery, and such treatment did not contribute to the survival of animals, which was only 5%. However, when one dose of peptide D-Ala-p2TA (5 mg/kg) was given to mice at 2 hours post CLP, survival rate dramatically increased to 90% (p<0.001). These data suggest that one dose administered 2 hours after exposure of mice to polymicrobial infection is sufficient to provide a high level of protection.

Figure 22:
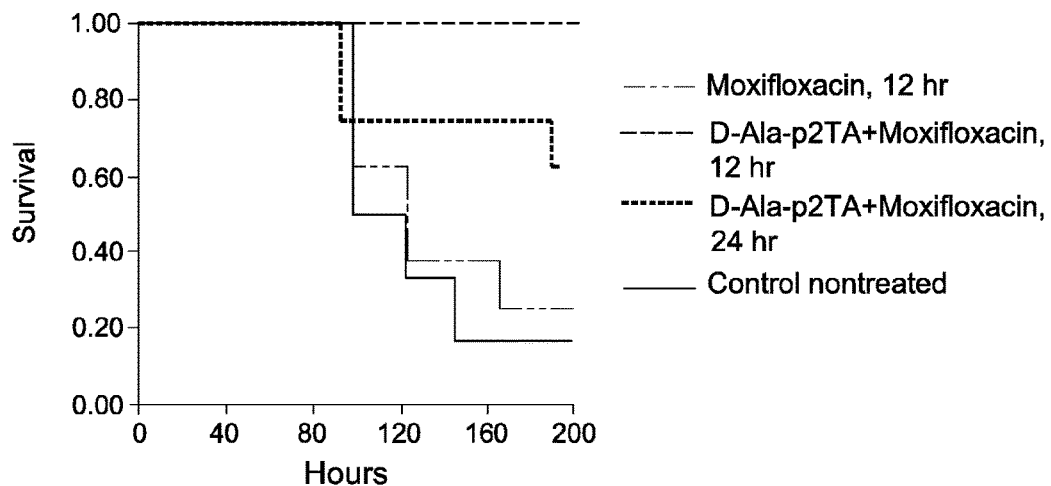
FIG. 22 is a Kaplan-Meier survival plot demonstrating the synergistic effect of D-Ala-p2TA and antibiotics, when administered at 12 or 24 hours post CLP.

5.2. Time Window of a Delayed Treatment by a Single Dose of the Peptide D-Ala-p2TA Obtaining good efficacy of a therapeutic agent, which is administered at a late (or delayed) time point after infection has already been established, is a challenge in clinical settings. Investigation of the potential time window of the peptide D-Ala-p2TA, during which the peptide D-Ala-p2TA may be administered as a single dose and yet rescue the animals from lethal infection, was performed (see FIG. 22). Most (85%) of the animals, which were subjected to CLP and left un-treated (85%) died within 3-6 days. When such animals were treated by a high efficacious dose of antibiotics (moxifloxacin; $LD_{90}$), which is administered at 12 hours post CLP, survival rates did not exhibit substantial change, and increased only to 22%, indicating that at this time point, addition of antibiotics alone, although used at its most efficacious dose, in not beneficial. In contrast, when animals were treated with a combination of antibiotics at a high dose together with a single dose of 5 mg/kg of the peptide D-Ala-p2TA, all administered at 12 hours post CLP, survival of 100% was gained. If the peptide D-Ala-p2TA treatment is given at a later time point, namely, at 24 hours post CLP (while antibiotics are given at 12 hours post CLP), survival rate of the animals was 65%, which is substantially higher compared to survival after treatment with antibiotics alone. These results indicate that under conditions that antibiotics treatment alone is not contributing to survival, addition of peptide D-Ala-p2TA dramatically improved survival.

5.3. Effect of One Versus Multiple Doses of Peptide D-Ala-p2TA

Figure 23:
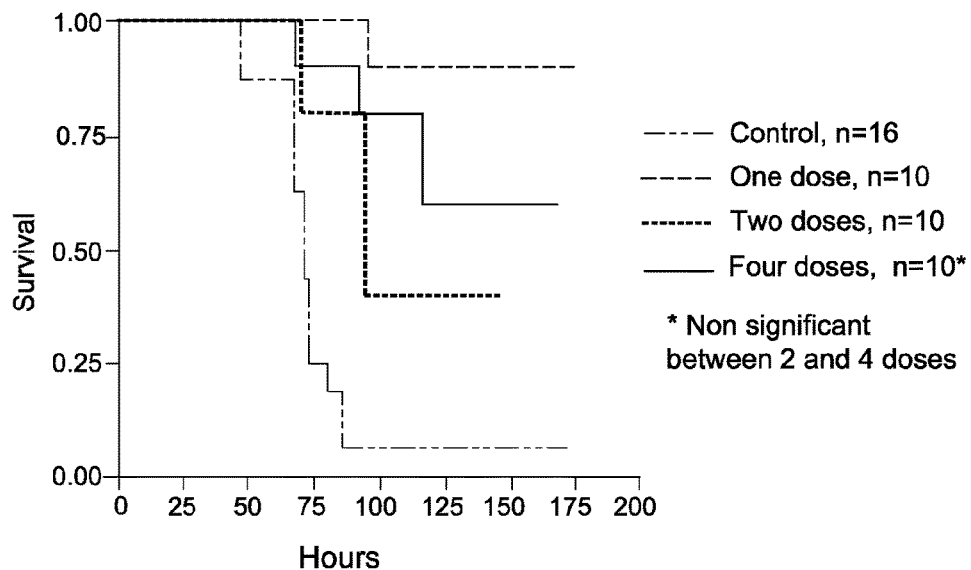
FIG. 23 is a Kaplan-Meier survival plot, demonstrating the efficacy in reducing mortality of one vs. multiple doses of D-Ala-p2TA in the CLP model.

Due to the apparent therapeutic advantage of administration of one dose as compared to 4 doses of the peptide D-Ala-p2TA, comparison between administrations of a single dose of the peptide D-Ala-p2TA to 2 and 3 doses was performed, when the first dose was given at 2 hours post CLP (FIG. 23). One dose of 5 mg/kg was found to be superior to either 2 or 4 doses, providing 90% protection (p=0.001 vs. control) as compared to 40 and 60% protection (with p value of 0.0002 and 0.0007 vs. control non-treated animal, respectively). Although the administration of 4 doses seemed more effective than administration of 2 doses, the difference in survival between the 2 and 4 doses was not statistically significant.

Figure 24:
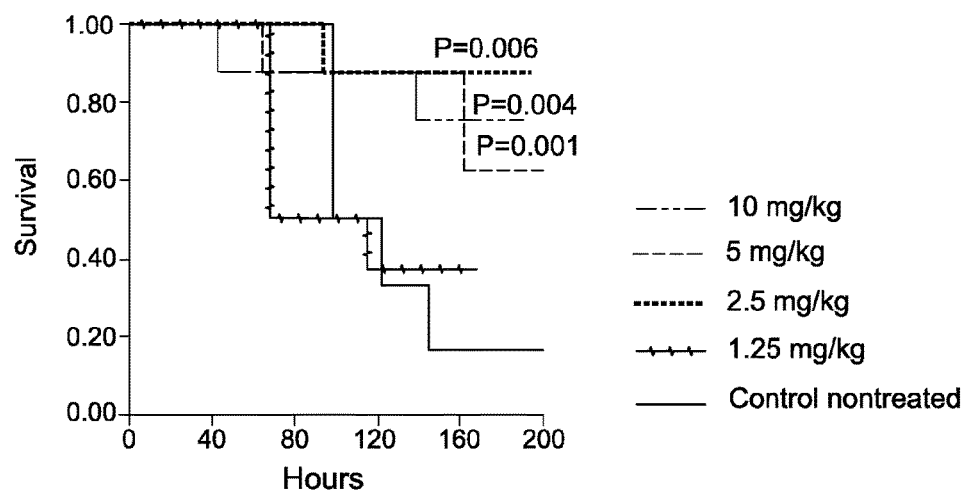
FIG. 24 is a Kaplan-Meier survival plot demonstrating the efficacy in reducing mortality of D-Ala-p2TA in CLP model, a dose response.
Figures 25A, 25B:
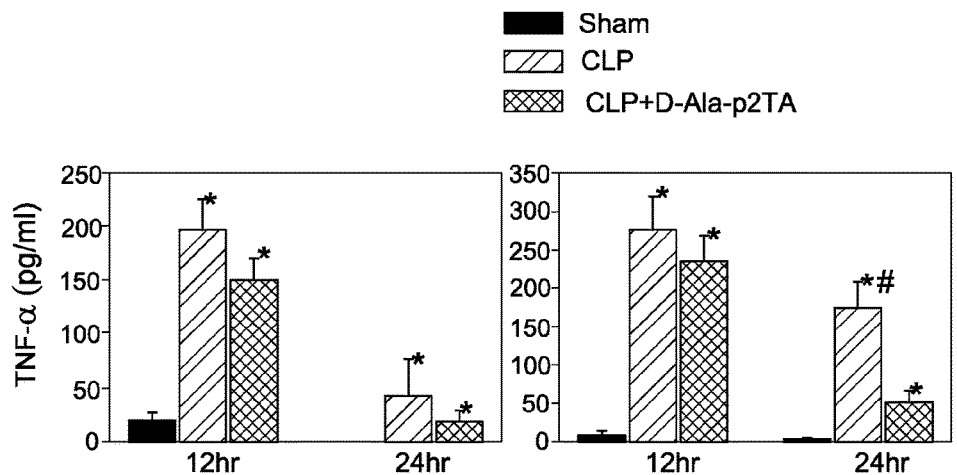
FIG. 25A is a graph demonstrating TNF-☐ levels in the blood at 12 and 24 hours post CLP.
FIG. 25B is a graph demonstrating TNF-☐ levels in the peritoneal fluid at 12 and 24 hours post CLP.
Figures 25C, 25D:
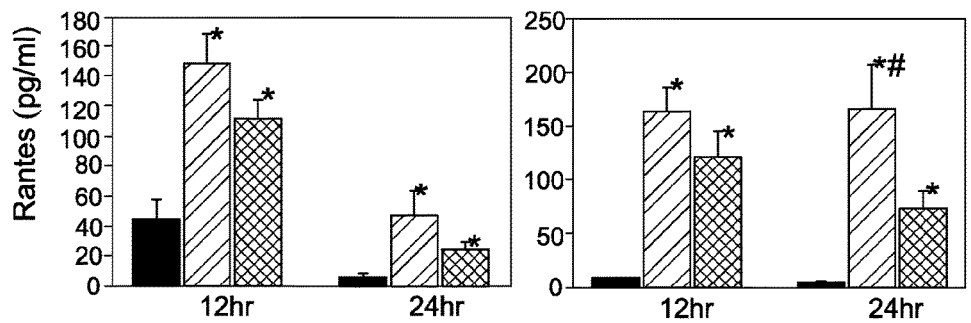
FIG. 25C is a graph demonstrating RANTES levels in the blood at 12 and 24 hours post CLP.
FIG. 25D is a graph demonstrating RANTES levels in the peritoneal fluid at 12 and 24 hours post CLP.
Figures 25E, 25F:
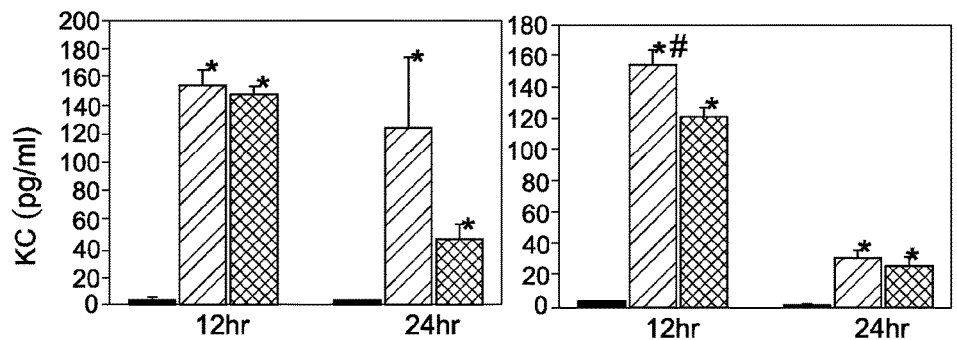
FIG. 25E is a graph demonstrating KC (IL-8) levels in the blood at 12 and 24 hours post CLP.
FIG. 25F is a graph demonstrating KC (IL-8) levels in the Peritoneal fluid at 12 and 24 hours post CLP.

5.4. Dose Response of a Single Administration of Peptide D-Ala-p2TA in CLP Model The dose response relationships of peptide D-Ala-p2TA, when administered as a single dose to animals subjected to CLP was examined. Animals were treated with a single dose of 1.25, 2.5, 5 or 10 mg/kg each of peptide D-Ala-p2TA (n=8 animals), 2 hours after the surgery. Suboptimal dose of moxifloxacin ($LD_{25}$) was given at time 0, and provided only 20% survival rate. The results are shown in FIG. 24. As shown in FIG. 24, a single dose of 2.5 mg/kg seemed to be superior, providing 90% survival (p=0.006 vs. control non-treated animals). Doses of 1.25, 5 and 10 mg/kg conferred 40%, 65% (p=0.01 vs. control) and 75% (p=0.054 vs. control) survival, respectively. No statistical significance was attained between doses of 2.5, 5, and 10 mg/kg. These data suggest that the optimal dose providing treatment benefit is 2.5 mg/kg, with a similar effect exhibited by the dose range of 2.5-10 mg/kg. However, a dose of 1.25 mg/kg was found to be less effective.

5.5. Cytokine Response after Treatment with the Peptide D-Ala-p2TA

The potential effect of the peptide D-Ala-p2TA on cytokine and chemokine production following CLP was further investigated.

Balb/c mice that were subjected to CLP were treated by one dose of the peptide D-Ala-p2TA (5 mg/kg) without any addition of antibiotics, initiated at 2 hours post surgery. Mice (6-8 treated and 6-8 control non-treated, as well as 2 sham-operated animals, which served as additional control) were euthanized at 12 and 24 hours after surgery, and blood was collected in heparinized syringes by cardiac puncture. Plasma was then obtained by centrifugation and stored at −70° C. until analyzed. Peritoneal fluids were obtained from mice by lavage, clarified by centrifugation and stored at −70° C. until analyzed. As a representative of Th1 cytokines, the levels of TNF-α were measured, and as representatives of chemokines that are associated with pro-inflammatory response, the levels of RANTES and KC were measured. A decrease was detected in both blood (plasma) and the local infection site (peritoneal fluid) of the D-Ala-p2TA peptide-treated animals (FIG. 25A-F). A maximal effect was observed at 24 hours for TNF-α (see FIGS. 25A and B) and RANTES (see FIGS. 25C and D) in both plasma and peritoneal fluid, and for KC in blood (see FIG. 25E). These results suggest that peptide D-Ala-p2TA treatment is associated with a reduced inflammatory cytokine/chemokine response and are consistent with the expected role of p2TA as a modulator of cytokine response. Statistical analysis was performed using 1-way ANOVA. The symbol * indicates P<0.05 vs. SHAM and the symbol # indicates P<0.06 vs. the peptide D-Ala-p2TA.

The levels of additional cytokine/chemokine in the peritoneum and blood following CLP were evaluated. Table 4 below summarized the levels of TNF-α, IL-6, IL-17A, IL-10, Rantes, MCP-1 and KC in the peritoneal fluid and plasma taken 12 or 24 hours after CLP. All cytokines/chemokines tested were increased after induction of sepsis. While treatment of the peptide D-Ala-p2TA showed a general reduction of TNF-α, Rantes, KC and IL-17A levels in the peritoneum and plasma at 12 and 24 hours post-CLP, the differences were only significant in the peritoneum for TNF-α and Rantes at 24 hours and KC at 12 hours as compared to vehicle-treated control mice. However, the peptide D-Ala-p2TA had no effect on CLP-induced IL-6, IL-10 and MCP-1 levels in either the peritoneal fluid of blood at any of the time points measured.

and tissue samples were obtained from the blood, peritoneal fluid, liver kidney and spleen of each animal. Levels of bacteria were measured by colony counts and compared between the treated and control groups.

As shown in FIG. 26A-E, the levels of bacteria grown from all tissues/organs were lower in the group that received the peptide D-Ala-p2TA, as compared to the PBS control group. In the blood sample (FIG. 26A), the substantial and statistical significant reduction was detected already at 12 hours. At the local infection site (peritoneal fluid), reduction was sustained also at 24 hours. In other key organs, the maximal reduction in bacterial count was detected at 24 hours post CLP. These results suggest that treatment with the peptide D-Ala-p2TA is associated with increased clearance of bacteria from the site of infection in the peritoneum and

TABLE 4

Cytokine/chemokine levels (pg/mL) in peritoneal fluid (P.F.) or plasma samples of mice subjected to sham, CLP + vehicle or CLP + D-Ala-p2TA peptide

| Cytokine/chemokine pg/mL | SHAM | CLP + vehicle | CLP + D-Ala-p2TA peptide |
|---|---|---|---|
| P.F. TNF-α 12 h | 9.2 ± 3.0 | 276.3 ± 43.3* | 235.5 ± 33.0* |
| Plasma TNF-α 12 h | 20.1 ± 7.4 | 197.2 ± 27.3* | 148.7 ± 20.3* |
| P.F. TNF-α 24 h | 1.6 ± 1.6 | 174.4 ± 33.9*# | 51.6 ± 13.6* |
| Plasma TNF-α 24 h | 0.0 ± 0.0 | 41.4 ± 34.4* | 18.2 ± 10.9* |
| P.F. Rantes 12 h | 8.7 ± 0.7 | 163.5 ± 22.7* | 121.2 ± 22.5* |
| Plasma Rantes 12 h | 44.9 ± 12.2 | 147.5 ± 20.0* | 121.3 ± 13.1* |
| P.F. Rantes 24 h | 4.6 ± 2.1 | 165.5 ± 41.8*# | 74.5 ± 15.8* |
| Plasma Rantes 24 h | 5.6 ± 2.3 | 46.8 ± 15.7* | 23.3 ± 5.3* |
| P.F. KC 12 h | 0.0 ± 0.0 | 154.2 ± 10.6*# | 120.6 ± 5.2* |
| Plasma KC 12 h | 2.6 ± 2.3 | 155.0 ± 8.9* | 148.1 ± 5.5* |
| P.F. KC 24 h | 1.1 ± 0.03 | 30.5 ± 4.3* | 25.3 ± 1.4* |
| Plasma KC 24 h | 1.5 ± 0.003 | 124.1 ± 50.4* | 45.9 ± 10.7* |
| P.F. IL-17A 12 h | 0.6 ± 0.6 | 144.0 ± 43.9* | 111.6 ± 58.7* |
| Plasma IL-17A 12 h | 3.2 ± 3.2 | 41.2 ± 20.7* | 34.7 ± 11.3* |
| P.F. IL-17A 24 h | 1.4 ± 1.4 | 214.0 ± 63.1* | 118.5 ± 38.1* |
| Plasma IL-17A 24 h | 1.2 ± 0.8 | 69.2 ± 26.2* | 70.6 ± 21.1* |
| P.F. MCP-1 12 h | 520.9 ± 117.9 | 6317.9 ± 1005.9* | 6684.2 ± 987.3* |
| Plasma MCP-1 12 h | 60.1 ± 31.6 | 403.3 ± 84.5* | 442.6 ± 52.6* |
| P.F. MCP-1 24 h | 91.0 ± 20.8 | 2344.4 ± 606.2* | 1265.7 ± 544.7* |
| Plasma MCP-1 24 h | 29.6 ± 21.3 | 653.5 ± 141.6* | 434.1 ± 85.7* |
| P.F. IL-10 12 h | 15.9 ± 5.2 | 440.1 ± 119.7* | 338.5 ± 119.1* |
| Plasma IL-10 12 h | 9.0 ± 3.7 | 51.9 ± 9.0* | 47.9 ± 10.2* |
| P.F. IL-10 24 h | 8.42 ± 3.6 | 165.5 ± 63.2* | 142.3 ± 71.1* |
| Plasma IL-10 24 h | 0.0 ± 0.0 | 42.7 ± 8.8* | 41.2 ± 9.7* |
| P.F. IL-6 12 h | 295.5 ± 59.4 | 8046.8 ± 919.5* | 7946.0 ± 1202.7* |
| Plasma IL-6 12 h | 17.9 ± 7.9 | 2427.4 ± 612.3* | 1797.3 ± 671.1* |
| P.F. IL-6 24 h | 30.1 ± 12.9 | 4294.5 ± 759.3* | 4040.2 ± 853.0* |
| Plasma IL-6 24 h | 2.1 ± 2.1 | 267.2 ± 43.1* | 198.5 ± 49.3* |

5.6. Effect of the Peptide D-Ala-p2TA on Bacterial Burden in Animals Subjected to CLP Animals subjected to CLP exhibit high load of bacteria in the blood and peritoneal fluid. Bacteria usually invade the blood from the peritoneal fluid, and are primarily killed by circulating polymorph nuclear cells (PMN) that recognize bacterial elements bound to macrophage surfaces and secondarily by the resident macrophages themselves. From the blood bacteria migrate to the liver and spleen (which are the primary sites for clearance of bacteria from the systemic circulation), where they are picked up by resident macrophages. To study the potential effect of the peptide D-Ala-p2TA on the bacterial load, the dissemination of bacteria in these tissues/organs was measured. Mice subjected to CLP were divided into 3 groups (n=6-8 in each group), that were either treated by the peptide D-Ala-p2TA (5 mg/kg) 2 hours post CLP, or injected with PBS and served as control, or sham-operated. None of the animals received antibiotics. Mice were euthanized after 12 and 24 hours from surgery, blood as well as in other organs enriched with macrophages. Statistical analysis was performed using 1-way ANOVA. The symbol * indicates P<0.05 vs. SHAM and the symbol # indicates P<0.06 vs. the peptide D-Ala-p2TA.

5.7. Effect of the Peptide D-Ala-p2TA on Leukocyte Infiltration into Key Organs The peptide D-Ala-p2TA was shown to trigger reduced levels of the Keratinocyte chemokine (KC), which is an important component responsible for recruitment and accumulation of polymorph nuclear cells (PMN) into target organs that have been implicated as key process in the development of systemic inflammation during sepsis, leading to organ dysfunction.

Figure 27A:
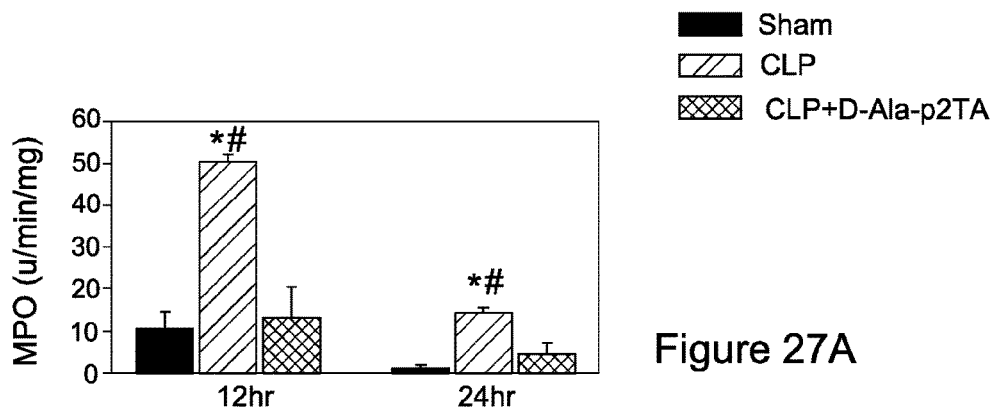
FIG. 27A is a graph demonstrating MPO activity in spleen, at 12 and 24 hours post CLP.
Figure 27B:
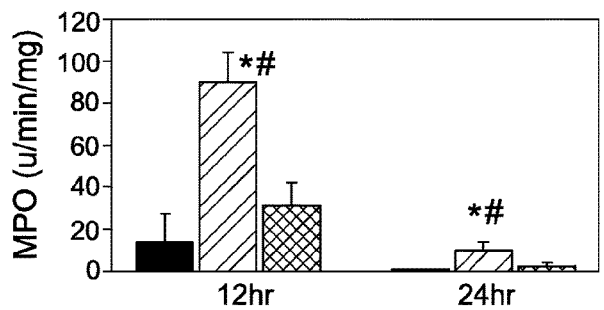
FIG. 27B is a graph demonstrating MPO activity in liver, at 12 and 24 hours post CLP.
Figure 27C:
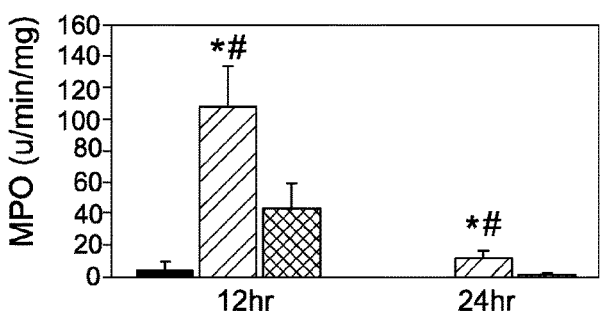
FIG. 27C is a graph demonstrating MPO activity in kidney, at 12 and 24 hours post CLP.

Therefore, the levels of PMN were evaluated in the spleen, liver and kidney of animals post CLP, and was measured by the activity of myeloperoxidase (MPO), which is a key enzyme associated with PMN activity, serving as an indirect marker for the presence of neutrophils. MPO activity was measured in homogenized tissues at 12 and 24 hours post CLP. Readout was performed spectrophotometrically at 460 nm, for 10 min, in one minute intervals. MPO activity is expressed as (Units/min/mg)=$A_{460} \times 13.5$/g, where $A_{460}$ equals the rate of change in absorbance. The results are shown in FIG. 27A-C, and demonstrate that after treatment with the peptide D-Ala-p2TA, substantial and statistical significant reduction in MPO activity can be detected at early time point after CLP (12 hours), and that a reduced activity is maintained at least until 24 hours later. Statistical analysis was performed using 1-way ANOVA. The symbol * indicates P<0.05 vs. SHAM and the symbol # indicates P<0.06 vs. peptide D-Ala-p2TA.

Further support for the reduced levels of PMN in key organs was exemplified by direct counting of PMN in histological slides, obtained from specific tissues of animals post CLP, after immunohistochemical staining, for assessment of neutrophil influx. Formalin-fixed paraffin sections obtained from CLP animals at 24 hours post CLP, were stained with Naphthol AS-D chloroacetate esterase (leukocyte-specific esterase), counter-stained with Gills hematoxylin solution and coverslipped. Numbers of neutrophils (esterase positively stained cells) present in the liver sections were randomly screened (5-7 fields/sample) microscopically, at ×400.

Figure 28:
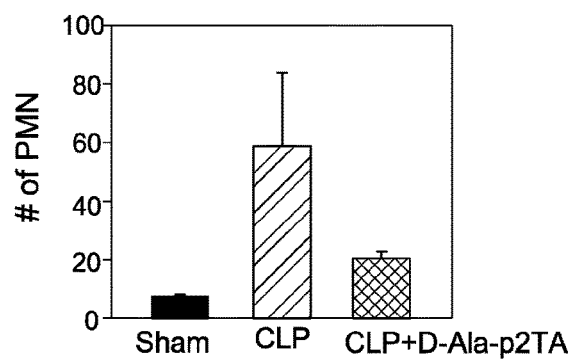
FIG. 28 is a graph demonstrating the effect of one dose of D-Ala-p2TA (administered without antibiotics at 2 hours post CLP) on PMN infiltration to the liver, measured by direct count at 24 hours post CLP. Numbers of neutrophils (esterase positively stained cells) present in the liver sections were randomly screened (5-7 fields/sample) microscopically at ×400. Units in the graph are in # of PMN.
Figure 32A:
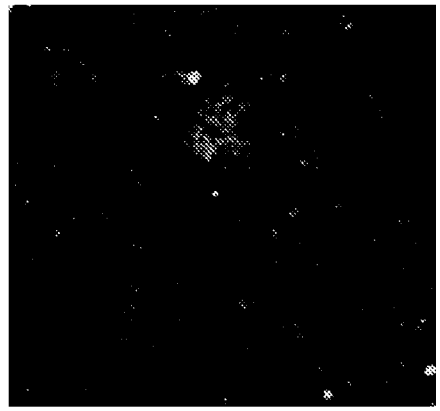
FIG. 32 includes representative immunohistochemical TUNEL staining micrographs in tissue sections. D-Ala-p2TA treatment reduced spleen and kidney tissue apoptosis 24 hours after CLP by TUNEL staining. Sham animals display no or slight staining of TUNEL in spleen (FIG. 32A) and kidney (FIG. 32B). While CLP mice exhibited extensive TUNEL staining (FIG. 32C, spleen.
FIG. 32D, kidney) when compared with sham-operated mice, D-Ala-p2TA-treated CLP mice showed significantly less TUNEL staining (FIG. 32E, spleen.
FIG. 32F, kidney). Original magnifications, ×100.
Figure 32B:
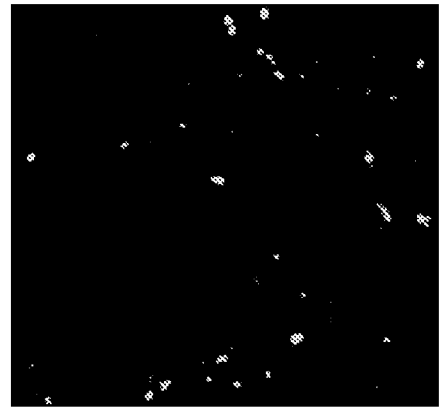
Figure 32C:
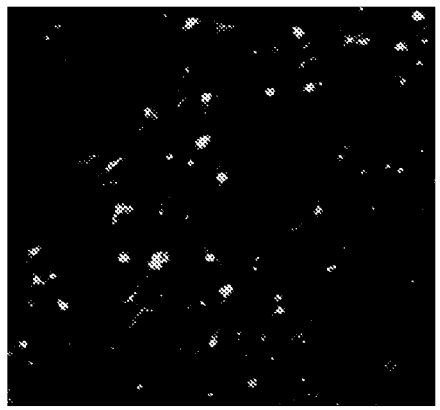
Figure 32D:
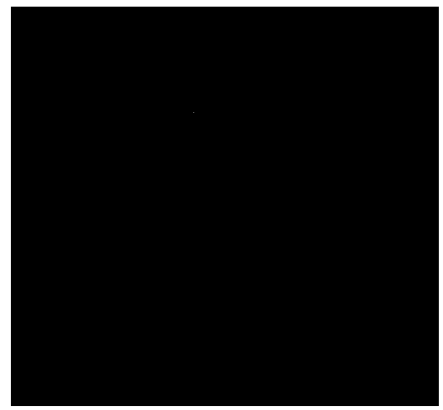
Figure 32E:
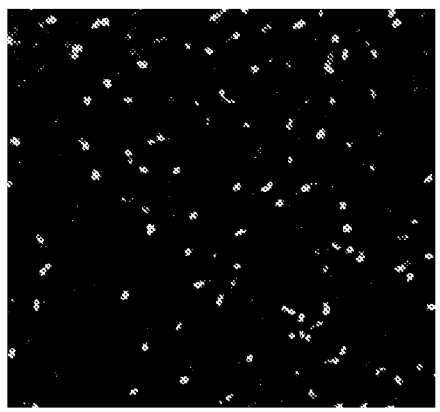
Figure 32F:
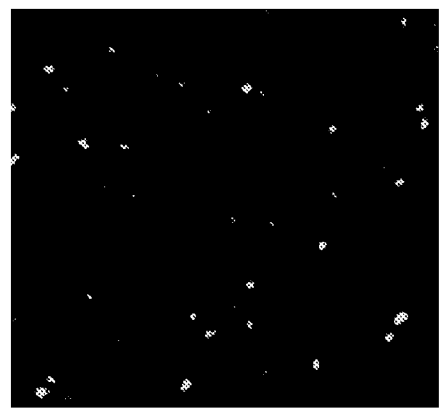

As an example, the reduced number of PMN in liver sections is shown in FIG. 28. Statistical analysis was performed using 1-way ANOVA. The symbol * indicates P<0.05 vs. SHAM and the symbol # indicates P<0.06 vs. the peptide D-Ala-p2TA.

The Peptide D-Ala-p2TA Had No Effects on CD28 Expression or Lymphocyte Proliferation Following CLP To determine if the peptide D-Ala-p2TA treatment affected the expression of CD28 on immune effector cells, the peripheral blood cells and splenocytes were examined 12 and 24 hours following surgery. The results indicated a modest down regulation of CD28 expression on CD3+ blood T lymphocytes and splenic T cells expressing either CD4 or CD8 cells. However, no significant changes were observed between D-Ala-p2TA treated and vehicle-treated groups for CD28 expression on all the cell populations tested (FIG. 29A-D): Surface expression of CD28 as assessed by flow cytometry showed significant reduction of levels on splenic (FIG. 29A) and blood (FIG. 29C) CD3+T lymphocytes at 12 and 24 hours post CLP with and without treatment by the D-Ala-p2TA peptide. While splenic (FIG. 29B) and blood (FIG. 29D) Gr1+ myeloid cells showed increased expression following CLP, no effect was observed by the D-Ala-p2TA peptide treatment.

To test the effect of the peptide D-Ala-p2TA on cell proliferation, ex vivo experiments were performed with isolated splenocytes taken from sham, CLP mice treated with or without the peptide D-Ala-p2TA, stimulated with anti-CD3 alone or anti-CD3+anti-CD28 antibodies and cultured for 72 hours. The splenocyte proliferation index was reduced after CLP at both 12 and 24 hours as compared to cells taken from sham animals. At 24 hours post-CLP, treatment with the peptide D-Ala-p2TA reduced the proliferation index as compared to non-treated group but these differences were not statistically significant.

5.8. Effect of the Peptide D-Ala-p2TA on Apoptosis in Key Organs (Kidney and Spleen)

Increased apoptotic processes in key organs such as kidney, liver and spleen, play a determining pathogenic role in the outcome of sepsis, contributing to organ failure. Therefore, the potential effect of the peptide D-Ala-p2TA treatment on renal and spleen apoptosis in animals subjected to CLP was studied (n=6-8 animals/group). Apoptosis was determined in histological slides taken from animals at 24 hours post CLP using TUNEL staining. Slides were examined under a fluorescent microscope for evidence of apoptosis, and the results are exhibited in FIG. 30. Reduction in the extent of apoptosis is indicated in both organs. Representative microscopy of TUNEL staining in histology sections of spleen at 24 h after CLP (200×) are shown in FIG. 31A-C in Sham (FIG. 31A), CLP (FIG. 31B) and CLP treated by D-Ala-p2TA. After CLP, a substantial apoptotic process is evident in the spleen, but a single treatment with peptide D-Ala-p2TA (at 2 hours post CLP) was capable of reducing this level substantially, and thus represents a reduced organ damage, which is consistent also with the low level of PMN recruitment to both kidney and spleen.

In order to compare the extent of sepsis-induced apoptosis following CLP between D-Ala-p2TA-treated and vehicle-treated mice, isolated splenocytes were also stained with an early apoptotic marker, Annexin V, combined with cell surface marker (CD3, CD4, CD8, B220, Gr-1) and analyzed by flow cytometry.

As shown in FIG. 32 (A-F), there was a slight increase in the frequency of apoptosis of isolated splenocytes after CLP when compared with shams at 12 and 24 hours post-CLP, but treatment with D-Ala-p2TA did not change the extent of CLP-induced apoptosis as assessed by Annexin V staining. Quantification of the images shown in FIGS. 32A-F was processed and analyzed using iVision software (and are shown in FIG. 30). Positive staining was defined through thresholding, the resulting images were analyzed, and data were expressed as percent area stained over total area (% area stained).

5.9. Summary of the Peptide D-Ala-p2TA Effects on Mice Subjected to CLP

Using the model of polymicrobial intra abdominal infection, it has been demonstrated that a single dose of peptide D-Ala-p2TA leads to improved survival when given as late as 12 and 24 hours after CLP. It was also shown that administration of the peptide D-Ala-p2TA is associated with significant effects, for example, as the following:

Decreased bacterial load in blood, infected site (peritoneum) and key organs (spleen, liver, kidney);
Reduction in cytokine/chemokine levels (TNF-α, Rantes, KC) in blood and peritoneal fluid;
Reduction in apoptosis in both Kidney and Spleen;
Reduction in neutrophil PMN activity in spleen, liver and kidney;
Reduction in neutrophil recruitment into liver (direct measure of PMN number).

Therefore, it is suggested that the peptide D-Ala-p2TA may be a viable therapeutic approach for the treatment of sepsis.

Example 6

Figure 33:
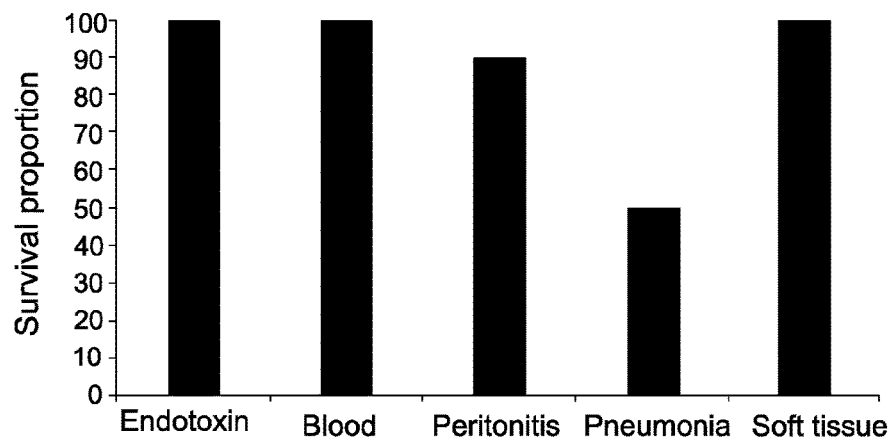
FIG. 33 is a bar graph showing a summary of the efficacy of D-Ala-p2TA in the various models of bacterial infection used herein.

Summary of Peptide D-Ala-p2TA Efficacy in Models of Bacterial Infections 6.1 Broad Spectrum of Activity Against Infections from Various Sources The efficacy of peptide D-Ala-p2TA given as a single dose was examined in several models of bacterial infections, including Gram positive infections (by *S. pyogenes* and *S. Pneumoniae*), Gram negative infections (*E. coli*) and mixed infections (intra-abdominal polymicrobial infection following CLP). It was tested either as a stand-alone treatment (in *S. pyogenes*) or as a combined treatment with sub-optimal doses of antibiotics, in all the infections. In all these cases, a substantial and high treatment benefit was detected (shown in FIG. 33), indicating that the peptide D-Ala-p2TA, as immunomodulator acting to attenuate the host immune response, is not specific to a particular type of infection and has a broad spectrum of activity against infections from various sources.

6.2. Summary of Effective Doses of the Peptide D-Ala-p2TA in the Various Models

Dose response studies were performed in various models of bacterial infections where the peptide D-Ala-p2TA was given at a single dose. Interestingly, the results indicated that in all the models used herein, whether peptide D-Ala-p2TA was given as a single therapy or in combination with antibiotics, the optimal doses that provided the highest efficacy were within the same range, of 2.5-5 mg/kg. Same doses were also efficacious when given (i) as treatment for infection due to a Gram negative or Gram positive or mixed infection (ii) with a sub-therapeutic or full therapeutic dose of antibiotics in the CLP model (iii) without antibiotics at all, such as in the S. pyogenes model (iv) at different time points relative to administration of antibiotics treatment (v) as a delayed treatment, at different time points post infection in the case of S. pyegenes, S. pneumoniae, E. coli, and the CLP model. Such uniformity of doses across all models suggests that indeed, the immunomodulatory effect of the peptide is targeting the host immune response, independently of the type and load of the bacterial infection. These studies are summarized in Table 5 below.

TABLE 5

Summary of efficacious doses of peptide D-Ala-p2TA

| Model | Doses range tested | Optimal dose |
|---|---|---|
| E. Coli | 0.05-5 mg/kg | 5 mg/kg |
| Polymicrobial | 1.25-10 mg/kg | 2.5-5 mg/kg |
| S. pyogenes | 1-10 mg/kg | 2.5-5 mg/kg |
| S. pneumoniae | 2.5-10 mg/kg | 5 mg/kg |

6.3. Summary of Dosing Regimen in Various Models

The dosing regimen (number of doses and interval between them) was investigated in the various infections models used herein. In all cases, a single dose (administered at different time points post infection) was compared to several doses (2, 3 and 4 doses), that were given at varying intervals between them, ranging from 4 to 24 hours. Importantly, it was found that in all models examined, administration of one dose (whether given at the time of infection or at a delayed time point post infection, and whether given as a monotherapy or together with antibiotics) was superior to multiple doses. However, interestingly, in all cases administration of multiple doses had an effect that was yet better than the control non-treated animals. A summary of these comparisons is shown in the Tables below. These results suggest that one dose of p2TA, administered within a time window that still supports the efficacy, is sufficient to protect animals from bacterial infection, and that additional doses may be even less favorable.

The reduced efficacy upon treatment with multiple doses was not due to toxic effects of peptide D-Ala-p2TA administration, as multiple doses that were administered to either healthy or sick animals were not associated with any signs of toxicity (shown in Table 6).

TABLE 6

Administration of multiple doses of the peptide D-Ala-p2TA

| Model | % Survival (One dose) | % Survival (Two doses) | Control | Comments |
|---|---|---|---|---|
| S. pyogenes | 60 | 0 (delayed death) | 0 | 5 mg/kg, 5 hr post |
| S. pyogenes | 90 | 40 | 20 | 2.5 mg/kg, 1 hr post |
| S. pneumoniae | 50 | 20 | 0 | 5 mg/kg, 24 hr post |
| CLP | 90 | 40 | 10 | 5 mg/kg, 2 hr post |

Toxicity studies conducted in mice and pigs and which included administration of 14 daily doses of 5 mg/kg of the peptide D-Ala-p2TA showed no toxic effects.

Example 7

Pharmacokinetics of Peptide D-Ala-p2TA in Animals and in Human Plasma

Upon systemic administration of the peptide D-Ala-p2TA into animals and human, the apparent elimination thereof from plasma is fast. The pharmacokinetics of peptide D-Ala-p2TA was studied in mice, pigs and human, using a dose of 5 mg/kg in both mice and pigs, and a human equivalent dose of 0.45 mg/kg. The results indicated that the pharmacokinetic parameters of peptide D-Ala-p2TA is consistent and predictable across species, and that in mouse, pig and man, the systemic clearance (CLs) values demonstrate that the clearance processes involved are of high capacity and rate (Table 7).

TABLE 7

PK parameters obtained for 3 species

| | Species | | |
|---|---|---|---|
| | Mice | Pigs | Human |
| Cmax (ng/ml) | 21679 | 1750 | 700 |
| AUC (ng-min/mL) | 82839 | 6030 | 7154 |
| VOD (mL/kg) | 231 | 1380 | 191 |
| CL (mL/min/kg) | 60.4 | 829 | 69 |
| $T_{1/2}$ (min) | 2.65 | 1.3 min | 1.83 |

The data concerning animal shown above (Table 7) were obtained following i.v. administration of the peptide D-Ala-p2TA (at 3 dose levels) to groups of mice and pigs, and plasma was collected at pre dose and at several time points post dose.

The data concerning humans shown above (Table 7) were elucidated in a clinical study performed in healthy volunteers entitled "Phase 1, Double Blind, Placebo-Controlled, Dose Escalation, Safety and Pharmacokinetic Clinical Trial of the peptide D-Ala-p2TA, a Peptide Antagonist in Healthy Volunteers".

In this trial, 25 healthy volunteers were administered with four different dose levels of the peptide D-Ala-p2TA, as shown in Table 8 below:

41

TABLE 8

Study design

| Cohort # | Peptide D-Ala-p2TA dose/ratio of active to placebo | |
|---|---|---|
| 1 | 7.5 µg/kg | 5:1 |
| 2 | 37.5 µg/kg | 5:1 |
| 3 | 150 µg/kg | 5:2 |
| 4 | 450 µg/kg | 5:1 |
| Total single dose subjects | | 20:5 |
| Total all subjects | | 25 |

Each subject received a single i.v. infusion of peptide D-Ala-p2TA or placebo control. Blood was collected for PK at different time points after infusion. peptide D-Ala-p2TA plasma concentrations in all cohorts peak near the end of the infusion and decline rapidly with a $T_{1/2}$ of a little over one minute. $T_{1/2}$ is very similar across the dose levels. Systemic exposure to peptide D-Ala-p2TA as measured by Cmax and AUC appears to be dose proportional. Consequently, plasma clearance (CL) which is derived from AUC and dose is similar for all doses.

A PK model of continuous infusion and one-compartment elimination was determined to be most appropriate for describing the data. PK parameters of peptide D-Ala-p2TA in humans (healthy volunteers) assayed by this model are shown in Table 7 for the highest dose given to human (0.45 mg/kg), which is the human equivalent dose of the efficacious dose given to mice. According to these data, the half-life of peptide D-Ala-p2TA in plasma is very short, and is not correlated with its biological long lasting effect observed when a single dose of the drug is administered to animals infected with bacteria. On the contrary, even when animals are administered with multiple doses of peptide D-Ala-p2TA, which may increase the plasma levels of the drug, efficacy is not improved, indicating that indeed plasma levels are not directly correlated to drug effect.

In addition, the apparent volume of distribution, approximately 200 mL/kg, is much larger than plasma volume which is consistent with potential distribution to sites outside the plasma compartment measured in the assay. Therefore, peptide D-Ala-p2TA may be eliminated from plasma by compartmentalization to other components that can stabilize it.

Example 8

Tissue Biodistribution of Peptide D-Ala-p2TA

To explore the fate of the peptide D-Ala-p2TA upon intravenous injection into animals, the peptide was radiolabeled with $^{14}C$ at one of its internal amino acids (valine). The product, [valine-$^{14}C$]-D-Ala-p2TA, namely H-D-Ala-Ser-Pro-Met-Leu-[U-$^{14}C$]Val-Ala-Tyr-Asp-D-Ala-OH) was purified by HPLC to 97.7% chemical purity and 98% radiochemical purity, had a specific activity of 260 mCi/mmol and was used for a set of biodistribution studies in male Balb/C mice. Mice were injected with a single intravenous dose of 5 mg base-eq./1000 µCi per Kg of body weight.

A group of 36 mice were injected with the radiolabeled peptide D-Ala-p2TA at the indicated dose, and at different time points (2, 4, 6, 8, 10, 20, and 30 min, 1, 2, 4, 8, and 24 h), groups of 3 mice were euthanized. Blood samples (1 mL taken from 3 mice per time point) were taken into syringe containing $K_3EDTA$ by cardiac puncture under $CO_2$-induced anesthesia. Both whole blood sample and the plasma sample were taken for radioactivity determination. After taking a terminal blood sample, the following tissues were collected: liver, kidney, spleen, heart, lung, brain, small intestine, large intestine, stomach wall, skeletal muscle, testes, pancreas, bone, thymus, thyroid, adrenals, bladder, gall bladder wall, lymph nodes, aorta and vena cava. Each tissue was weighted and stored at −20° C. prior to analysis.

Tissues were then processed as follows: Bone (minced and mixed), thymus (minced and mixed), thyroid, adrenals, bladder, gall bladder wall, spleen, kidney, heart, lung, testes, pancreas, lymph nodes, aorta and vena cava were directly placed onto combustion boats and placed in a hood to dry, and then combusted using a Harvey Biological Sample Oxidizer, followed by Liquid Scintillation Counter (LSC). Other tissues, such as liver, brain, small intestine, large intestine, stomach wall and skeletal muscle were homogenized and aliquots were taken and processed as above.

Figure 34A:
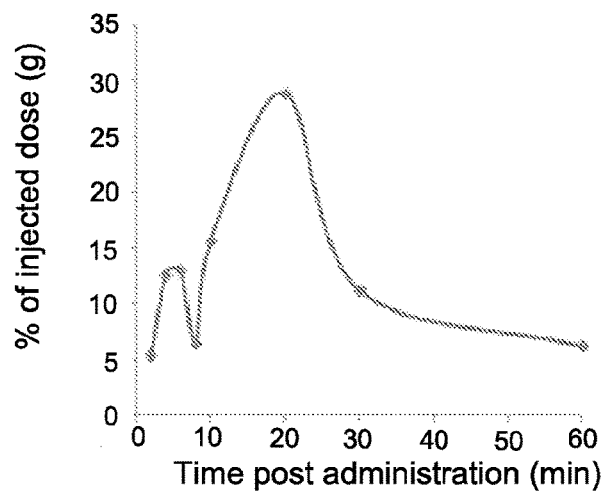
FIG. 34 includes graphs demonstrating tissue concentrations-time curves after a single i.v. administration of the peptide D-Ala-p2TA in which the valine residue is replaced by [valine-$^{14}$C] (5 mg/kg) to male Balb/c mice. The levels of the peptide D-Ala-p2TA are shown in lymph nodes (FIG. 34A) and plasma (FIG. 34B) over the first hour following its systemic administration.
Figure 34B:
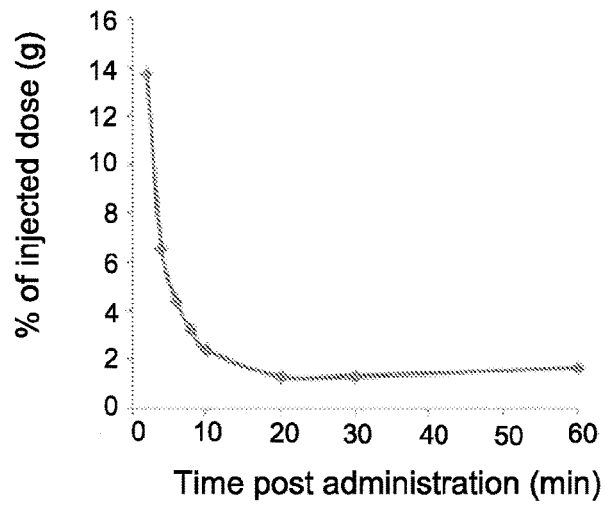

The distribution pattern at early time points is consistent with disposition of [$^{14}C$]-D-Ala-p2TA into multiple tissues, particularly into highly perfused tissues and organs. Interestingly, as shown in FIG. 34A-B, substantial accumulation over the early time points is evident in lymphatic organs such as the lymph nodes (FIG. 34A) and thymus (not shown), as compared to clearance from plasma (FIG. 34B). Accumulation starts at 4 minutes post injection, and reaches a peak at 20 minutes. Thereafter, the radioactivity level gradually decreases, yet it remains higher than in the plasma even few hours after injection.

The accumulation of [$^{14}C$]-D-Ala-p2TA in the lymphatic organs (lymph nodes and spleen) is best described as tissue to plasma ratio (shown in FIG. 35A-B). Already at 4 minutes post infusion, the ratio of lymph nodes to plasma [$^{14}C$]-D-Ala-p2TA is greater than 1, indicating the buildup of radioactivity in this organ. At 20 minutes, the levels in the lymph nodes is 22-fold higher than in the plasma, and remains more than 5-fold higher for 2 hours, and interestingly, even for 24 hours post dosing, this ratio is greater than 3-fold (FIG. 35A). In the spleen, similar accumulation process occurs, although to a lower extent: at 20 min after injection, the ratio of radioactivity in the spleen as compared to plasma is 6-fold higher, and at 24 hours post injection, the ratio is 3-fold higher (FIG. 35B).

Figure 36A:
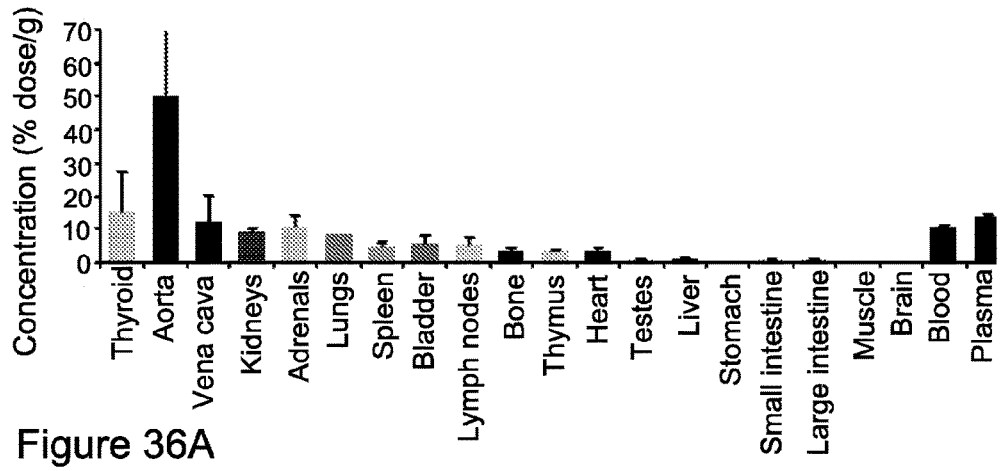
FIG. 36 includes graphs demonstrating the distribution of the peptide D-Ala-p2TA in which the valine residue is replaced by [valine-$^{14}$C] (5 mg/kg) in various tissues of mice at 2 minutes (FIG. 36A), 10 minutes (FIG. 36B) and 20 minutes (FIG. 36C) post injection into mice.
Figure 36B:
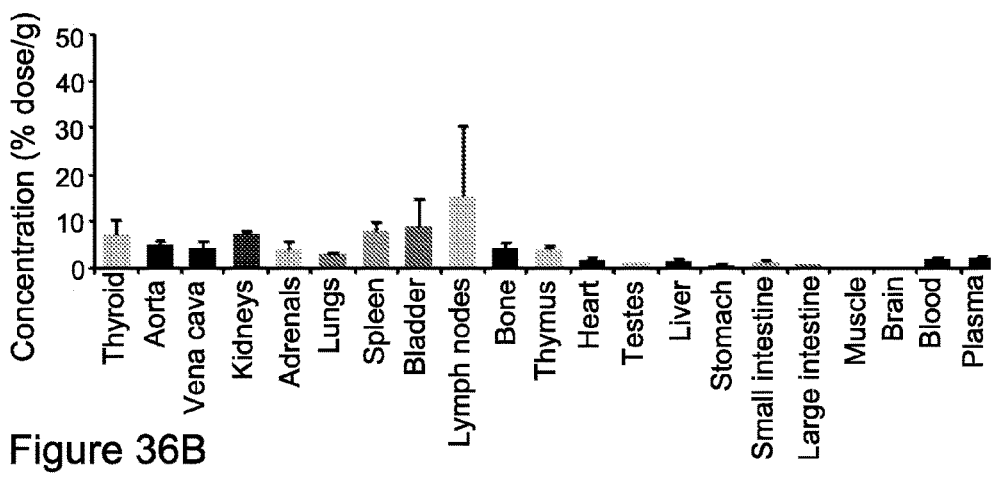
Figure 36C:
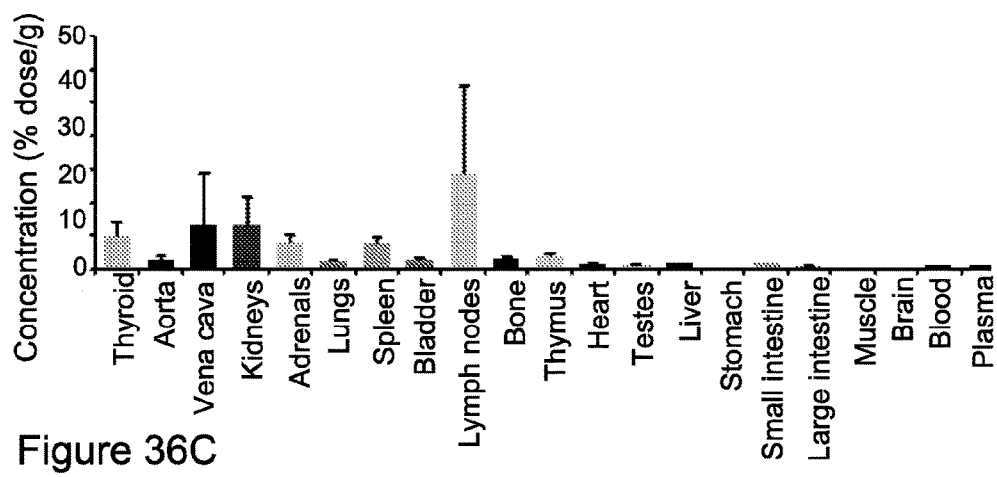

The relative high levels in the lymph nodes compared to other tissues and organs is presented in FIG. 36 A-C, demonstrating that already at 10 and 20 minutes post-injection (FIGS. 36 B and C respectively), the level in other organs, is gradually decreasing from the level found at 2 minutes (FIG. 36A) while the level in the lymph nodes is taking place.

Potentially, as T cells from the lymphatic organs are re-circulated, a bound drug could be re-distributed from the lymphatic organs to the systemic circulation, and thus its availability exceeds its plasma half life. As the drug is working systemically, it can exert its effect in cases of severe bacterial infections that are spread to the systemic circulation.

Example 9

Phase II Clinical Trial

In order to assess the safety and pharmacokinetics of the peptide D-Ala-p2TA, to demonstrate the clinical effect of this peptide and in order to guide dose selection, a phase II study in human patients suffering from Necrotizing Soft Tissue Infection (NSTI) was performed as follows.

Patients were selected predominantly based on their diagnosis as suffering from NSTI (of 343 patients pre-screened, 43 randomized patients were selected out of which 40 patients were included in the efficacy analysis). Of the above 40 randomized patients, 10 patients were administered with a placebo, 15 patients were treated once with 0.25 mg/kg of the D-Ala-p2TA peptide and 15 patients were treated once with 0.5 mg/kg of the D-Ala-p2TA peptide). Patients were administered with the peptide within 6 hours of the clinical diagnosis, at a single dose.

In addition, all patients were also treated with standard of care treatments, including a wide range of antibiotic treatment, debridement procedure and supportive care given in intensive care unit (ICU) with or without ventilation. A debridement procedure is a surgical intervention performed in the operating room to eliminate substantial amount of necrotic tissue. Bedside procedures such as dress change, minimal procedures to trim margins, etc. were not considered as a debridement procedure for the purpose of the present analysis. Patients were followed up for 28 days.

Bacteriological Analysis

Bacteriological analysis of the infections revealed that NSTI involved various bacterial pathogens, including, Gram negative (e.g. *Proteus* species, *E. coli*, etc.) and Gram positive (e.g. *Staphylococcus aureus, Streptococcus pyogenes* (Group A or B), *Strep viridans*, etc.). Pathogens were either aerobic or anaerobic, and infections were either by a single pathogen or mixed pathogens.

Stay in Intensive Care Unit (ICU)

Figure 37:
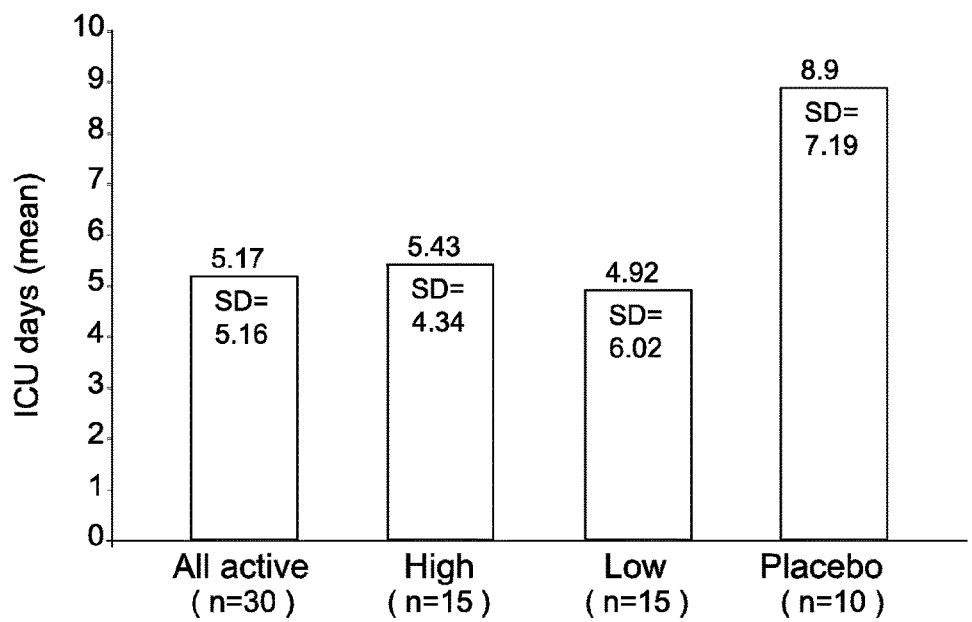
FIG. 37 Describes the mean length of stay (±SD) in the Intensive Care Units (ICU) of patients with Necrotizing Soft Tissue Infection (NSTI) treated by one single administration with either 0.5 mg/kg or 0.25 mg/kg of the D-Ala-p2TA peptide as compared to placebo. As another comparison, all active treatment groups were pooled together and compared together with placebo. Days in ICU were calculated based on a 24 hours clock, starting from drug administration time.

The results of the clinical study show a clear treatment benefit. For example, as demonstrated in FIG. 37, the length of stay in the intensive care unit (ICU) was reduced approximately two-fold upon one treatment with either low (0.25 mg/kg) or high (0.5 mg/kg) D-Ala-p2TA peptide dose. The days were calculated based on 24 hour clock starting at admission to ICU. Similarly, the number of days on ventilator, as well as the hospital duration of stay, were two-fold reduced.

Debridement Procedures Required

Figure 38A:
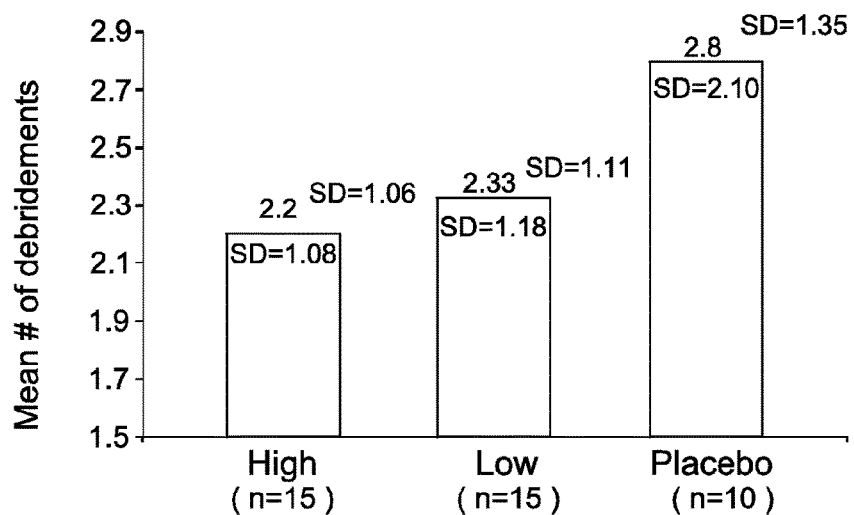
FIG. 38A Describes the total mean number of debridements (±SD) performed in each of the treatment groups (0.5 and 0.25 mg/kg) as compared with placebo.
Figure 38B:
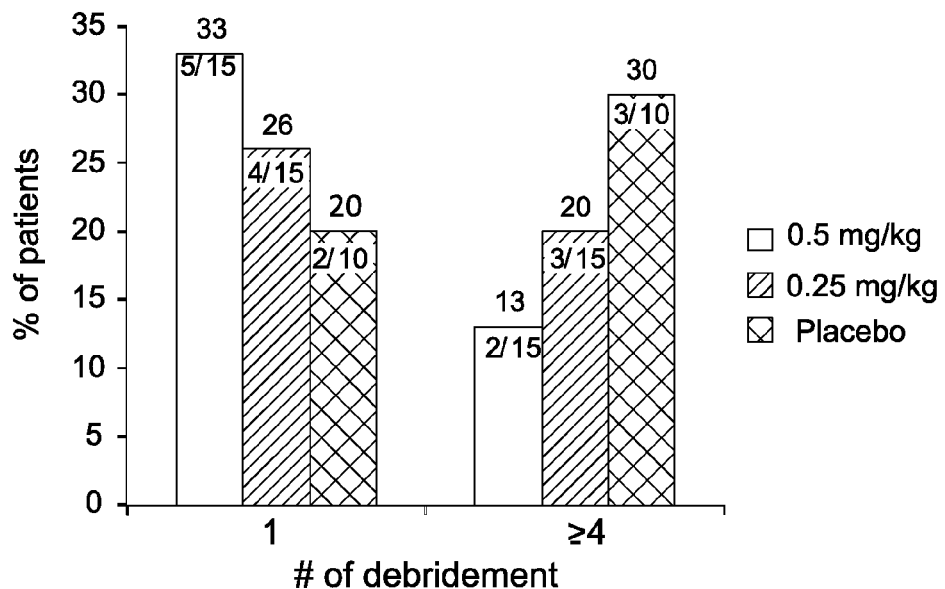
FIG. 38B Describes the proportion of patients needed only one debridement to recover from the infection (in each of the treatment groups) as well as the proportion of patients needed for 4 or more debridements to recover.

Interestingly, the number of debridement procedures (as defined above) which were required as standard of care treatment of patients within the time frame of the clinical study (28 days) was significantly reduced. As shown in FIG. 38A and FIG. 38B, patients administered with placebo required 2.8 debridement procedures while patients administered with the low or high dose of the peptide D-Ala-p2TA only required 2.3 or 2.2 debridement procedures (respectively).

Interestingly, a higher proportion of patients treated with the peptide were subjected to only one debridement, as compared with placebo (FIG. 38B). In patients administered with the 0.5 mg/kg dose, 33% needed only one debridement to heal, whereas 20% of the placebo underwent one debridement.

Consistently, the proportion of patients needing 4 or more debridements, was 30% higher in the placebo group as compared with the group receiving the 0.5 mg/kg dose (13%). These data suggest that a better local control of the infection is obtained due to treatment with the peptide.

Resolution Over Time of Organ Dysfunction (SOFA)

Figure 39:
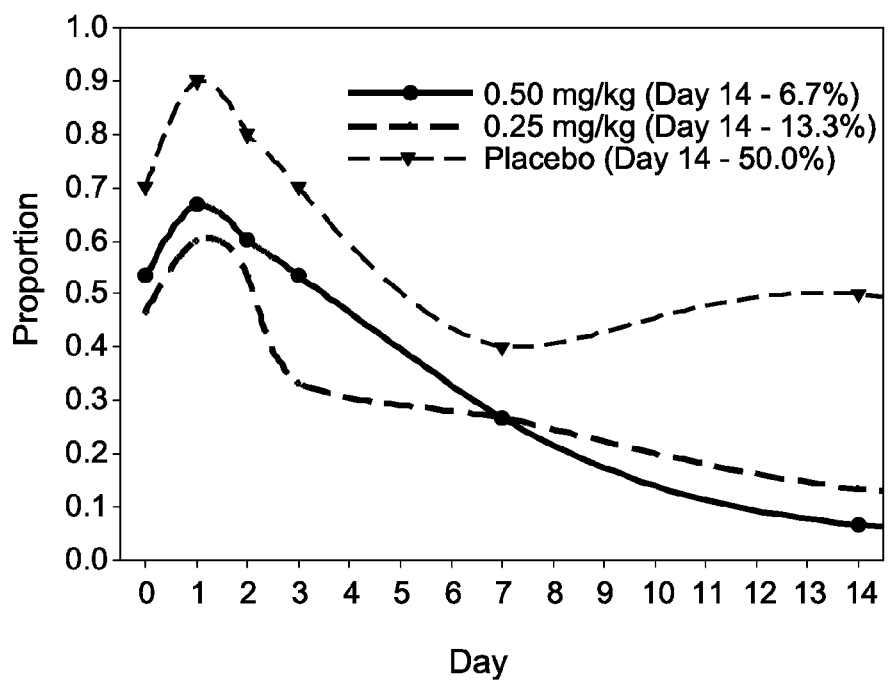
FIG. 39 Describes the proportion of patients having organ dysfunction (defined as having a SOFA score of ≥3), in each of the treatment groups over time (between days 1-14).

In addition to the above results and as demonstrated in FIG. 39, the proportion of patients with organ failure was lower for patients treated with the peptide (either 0.25 or 0.5 mg/kg dose) as compared with the patients treated with placebo. At day 14, 6.7% of patients had organ failure (Organ failure was defined as SOFA score≥3), when given 0.5 mg/kg as compared with 50% that belonged to the placebo group. The changes in SOFA score was evaluated between days 1-14, in which term the proportion of patients with organ resolution and failure over time as well as the time to resolution of organ dysfunction/failure were analyzed.

Analysis of Systemic Biomarkers

Changes in systemic biomarkers over time were also analyzed in patients treated with the peptide D-Ala-p2TA, as compared to patients administered with placebo.

Plasma for cytokine levels was collected before and after drug administration (up to 72 hours), 10 different cytokines were examined (pro-inflammatory, anti inflammatory and chemokines). Cytokine level was analyzed as the change from the baseline (immediately prior to drug administration) and up to 4, 24, 48 and 72 hours. The results of this analysis for 5 cytokines are presented in Table 9 below. These results indicate that the cytokine levels of patients treated with the 0.5 mg/kg dose are reduced as compared with the placebo group, and that such reduction occur earlier, already at 24 h post treatment, while reduction in the placebo group occurs later (48-72 h), if at all. Further, changes in cytokine levels were detected only in pro-inflammatory cytokines, such as IL-17, IFN-γ, IL1-β or IL3 and no change was observed in an anti-inflammatory cytokine, IL-10. This is consistent with the expected MOA as specified [9].

A summary of the patient's response to the treatment is presented in Table 10, below.

TABLE 9

Timing and effect size of treatment with D-Ala-p2TA on plasma cytokines of NSTI patients. The Average changes in blood cytokine was used to calculate the maximal effect size (with Wilcoxon Rank Sum Tests p value) in NSTI patients treated by the effective (0.5 mg/kg) dose of D-Ala-p2TA as compared to patients treated with placebo. The timing of maximal reduction in cytokine levels is specified for each individual cytokine

|  | Treatment | Time to change (hr) | Extent reduction | p value |
|---|---|---|---|---|
| Pro inflammatory |  |  |  |  |
| IL-17 | 0.5 mg/kg | 24 | 80% | 0.009 |
|  | Placebo | 48 |  |  |
| IFN-γ | 0.5 mg/kg | 24 | 81% | 0.11 |
|  | Placebo | 72 |  |  |
| IL-1β | 0.5 mg/kg | 24 | 71% | 0.10 |
|  | Placebo | No |  |  |
| IL-3 | 0.5 mg/kg | 24 | 64% | 0.25 |
|  | Placebo | No |  |  |
| Anti inflammatory |  |  |  |  |
| IL-10 | 0.5 mg/kg | 24 | No effect | 0.55 |
|  | Placebo | 24 |  |  |

TABLE 10

Summary of the response to treatment

| Treatment | 0.5 mg/kg | Placebo |
|---|---|---|
| % Change in SOFA score days 1-14 | 89 | 53 |
| % of patients with no organ dysfunction on day 14 | 40 | 25 |
| % patients with organ failure day 14 | 10 | 50 |
| Days in ICU | 5.4 | 8.9 |
| Days on Ventilator | 2.7 | 5.2 |
| % of patients with 1 debridement | 33 | 20 |
| % of patients with ≥4 debridement | 13 | 30 |

In conclusion, the peptide D-Ala-p2TA demonstrated a consistent treatment benefit across multiple end points, affecting clinically meaningful parameters related to the disease, with a higher proportion of patients treated with peptide D-Ala-p2TA that showed a clinical response compared to placebo. The superiority of the 0.5 mg/kg dose was confirmed, which is consistent with the findings in preclinical models, suggesting that an equivalent animal dose (of 0.5 mg/kg) is the optimal dose. In addition, the effects detailed above start immediately after drug administration and are sustained over time, although only administered once, consistent with the proposed mechanism of action of the peptide D-Ala-p2TA, as detailed herein above.

The invention claimed is:

1. A method for treating a bacterial infection in a human patient and any acute inflammation associated therewith, which bacterial infection is with at least one bacteria selected from the group consisting of Gram-positive bacteria or Gram-negative bacteria, said method comprising a single administration, within a seven day period from said single administration to said patient, at a suitable time following said infection, one single dose of a therapeutically effective amount of a peptide consisting of the amino acid sequence SPMLVAYD as denoted by SEQ ID NO:1, also denoted as p2TA, or a peptide consisting of the amino acid sequence (D-A)SPMLVAYD(D-A) as denoted by SEQ ID NO:2, also denoted as D-Ala p2TA, or a salt or ester of any of said

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: p2TA

<400> SEQUENCE: 1

Ser Pro Met Leu Val Ala Tyr Asp
1               5

<210> SEQ ID NO 2
<211> LENGTH: 10
<212> TYPE: PRT
<213> ORGANISM: Artificial Sequence
<220> FEATURE:
<223> OTHER INFORMATION: D-Ala-p2TA
<220> FEATURE:
<221> NAME/KEY: MISC_FEATURE
<222> LOCATION: (1)..(1)
<223> OTHER INFORMATION: X equals to D-Ala
<220> FEATURE:
<221> NAME/KEY: MISC_FEATURE
<222> LOCATION: (10)..(10)
<223> OTHER INFORMATION: X equal to D-Ala

<400> SEQUENCE: 2

Xaa Ser Pro Met Leu Val Ala Tyr Asp Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Scrambled peptide
<220> FEATURE:
<221> NAME/KEY: MISC_FEATURE
<222> LOCATION: (1)..(1)
<223> OTHER INFORMATION: X equals to D-Ala
<220> FEATURE:
<221> NAME/KEY: MISC_FEATURE
<222> LOCATION: (10)..(10)
<223> OTHER INFORMATION: X equal to D-Ala

<400> SEQUENCE: 3

Xaa Ala Ser Met Asp Tyr Pro Val Leu Xaa
1               5                   10
``` peptides, or a pharmaceutical composition comprising the same, wherein said therapeutically effective amount is from about 0.1 to about 1 mg peptide/kg body weight of the human patient.

2. The method according to claim 1, wherein said peptide is a peptide consisting of the amino acid sequence (D-A) SPMLVAYD(D-A) as denoted by SEQ ID NO:2, also denoted as D-Ala-p2TA, or a salt or ester thereof.

3. The method according to claim 1, wherein said bacterial infection and any acute inflammation associated therewith is selected from the group consisting of Necrotizing Soft Tissue Infection (NSTI), or polymicrobial intra-abdominal infection.

4. The method according to claim 1, wherein said therapeutically effective amount is from 0.25 mg to 0.5 mg peptide/kg body weight of said patient.

5. The method according to claim 1, wherein said peptide is administered to said patient by oral administration, intravenous administration, intramuscular administration, intraperitoneal administration, intrathecal or subcutaneous injection, intrarectal administration, intranasal administration, ocular administration or topical administration.

6. The method according to claim 1, wherein said therapeutically effective amount of said peptide is administered within about 7 days following said infection or the onset of clinical manifestation of said infection.

7. The method according to claim 1, wherein said method further comprises administering to said patient at least one of (i) a therapeutically effective amount of a therapeutically active agent selected from the group consisting of antimicrobial agents, antiviral agents and steroids, and (ii) supportive standard of care treatment being at least one treatment selected from the group consisting of ventilation, surgery, wound care, hyperbaric oxygen, intravenous immunoglobulins (IVIG), corticosteroids, plasmapheresis, negative pressure wound therapy and activated protein C.

8. The method according to claim 1, wherein said peptide is a peptide consisting of the amino acid sequence SPMLVAYD as denoted by SEQ ID NO:1, also denoted as p2TA, or a salt or ester thereof.

9. The method according to claim 1, wherein said therapeutically effective amount of said peptide is administered within about 72 hours following said bacterial infection or the onset of clinical manifestation of said bacterial infection.

10. The method according to claim 1, wherein said therapeutically effective amount of said peptide is administered immediately following initial diagnosis of said bacterial infection or the onset of clinical manifestation of said bacterial infection.

11. The method according to claim 1, wherein said single dose is administered after said bacterial infection and any acute inflammation associated therewith results in multi-organ failure, sepsis, severe sepsis, septic arthritis or septic shock.

12. A method according to claim 1, wherein said patient is suffering from inflammation associated with said bacterial infection, which inflammation is induced by at least one of said bacteria.

13. The method according to claim 3, wherein said bacterial infection is Necrotizing Soft Tissue Infection (NSTI).

14. A method in accordance with claim 7, wherein said at least one additional therapeutically active agent is an antimicrobial agent selected from the group consisting of an antibiotic agent, a bacteriostatic agent, a bactericidal agent, and an antifungal agent.

15. A method in accordance with claim 14, wherein said antimicrobial agent is an antibiotic agent.

16. The method according to claim 15, wherein said peptide and said antibiotic agent are administered at different time points, at a different interval between administrations, for different durations of time, or in a different order.

* * * * *